(12) United States Patent
Shamsheyeva et al.

(10) Patent No.: US 11,603,550 B2
(45) Date of Patent: Mar. 14, 2023

(54) RAPID DETERMINATION OF MICROBIAL GROWTH AND ANTIMICROBIAL SUSCEPTIBILITY

(71) Applicant: Accelerate Diagnostics, Inc., Tucson, AZ (US)

(72) Inventors: Alena Shamsheyeva, Tucson, AZ (US); David C. Howson, Denver, CO (US); Steven W. Metzger, Tucson, AZ (US)

(73) Assignee: Accelerate Diagnostics, Inc., Tucson, AZ (US)

( * ) Notice: Subject to any disclaimer, the term of this patent is extended or adjusted under 35 U.S.C. 154(b) by 818 days.

(21) Appl. No.: 15/484,250

(22) Filed: Apr. 11, 2017

(65) Prior Publication Data

US 2017/0218426 A1 Aug. 3, 2017

Related U.S. Application Data

(62) Division of application No. 14/209,917, filed on Mar. 13, 2014, now Pat. No. 9,677,109.

(60) Provisional application No. 61/798,105, filed on Mar. 15, 2013.

(51) Int. Cl.
| | |
|---|---|
| *C12Q 1/18* | (2006.01) |
| *C12Q 1/02* | (2006.01) |
| *B01L 3/00* | (2006.01) |
| *C12M 1/34* | (2006.01) |
| *G16B 5/00* | (2019.01) |

(52) U.S. Cl.
CPC .......... *C12Q 1/18* (2013.01); *B01L 3/502715* (2013.01); *C12M 41/36* (2013.01); *C12Q 1/02* (2013.01); *G16B 5/00* (2019.02); *B01L 2200/04* (2013.01); *B01L 2200/0647* (2013.01); *B01L 2300/024* (2013.01); *B01L 2300/0864* (2013.01); *B01L 2300/0867* (2013.01)

(58) Field of Classification Search
None
See application file for complete search history.

(56) References Cited

U.S. PATENT DOCUMENTS

| | | | |
|---|---|---|---|
| 2,666,355 | A | 1/1954 | Trurnit |
| 3,493,772 | A | 2/1970 | Daughters, II et al. |
| 3,532,790 | A | 10/1970 | Greenberg et al. |
| 3,637,313 | A | 1/1972 | Upatnieks |
| 3,792,081 | A | 2/1974 | Higuchi et al. |
| 3,811,036 | A | 5/1974 | Perry |

(Continued)

FOREIGN PATENT DOCUMENTS

| | | |
|---|---|---|
| AU | 772760 | 5/2004 |
| EP | 0498920 | 8/1992 |

(Continued)

OTHER PUBLICATIONS

Davies et al. Origins and Evolution of Antibiotic Resistance. Microbiology and Molecular Biology Reviews 2010, vol. 74, No. 3, pp. 417-433 (Year: 2010).*

(Continued)

*Primary Examiner* — Olivia M. Wise
(74) *Attorney, Agent, or Firm* — Wood Herron & Evans LLP

(57) ABSTRACT

Systems and methods for rapid determination of microorganism growth and antimicrobial agent susceptibility and/or resistance are disclosed.

16 Claims, 26 Drawing Sheets

(56) References Cited

U.S. PATENT DOCUMENTS

| | | |
|---|---|---|
| 3,832,532 A | 8/1974 | Praglin et al. |
| 3,854,480 A | 12/1974 | Zaffaroni |
| 3,904,293 A | 9/1975 | Gee |
| 3,926,564 A | 12/1975 | Giaever |
| 3,935,073 A | 1/1976 | Waters |
| 3,938,515 A | 2/1976 | Leeper et al. |
| 3,957,362 A | 5/1976 | Mancini et al. |
| 3,961,628 A | 6/1976 | Arnold |
| 4,069,307 A | 1/1978 | Higuchi et al. |
| 4,070,248 A | 1/1978 | Schmidt |
| 4,076,591 A | 2/1978 | Heden |
| 4,136,250 A | 1/1979 | Mueller et al. |
| 4,199,449 A | 4/1980 | Slejko |
| 4,199,499 A | 4/1980 | Smithwick, Jr. et al. |
| 4,200,493 A | 4/1980 | Wilkins et al. |
| 4,220,152 A | 9/1980 | Dresback |
| 4,224,439 A | 9/1980 | Ayers et al. |
| 4,233,847 A | 11/1980 | Walker |
| 4,246,343 A | 1/1981 | Wilkins et al. |
| 4,259,442 A | 3/1981 | Gayral |
| 4,282,287 A | 8/1981 | Giese |
| 4,288,543 A | 9/1981 | Sielaff et al. |
| 4,313,734 A | 2/1982 | Leuvering |
| 4,325,910 A | 4/1982 | Jordan |
| 4,330,440 A | 5/1982 | Ayers et al. |
| 4,332,476 A | 6/1982 | Stenberg et al. |
| 4,351,337 A | 9/1982 | Sidman |
| 4,357,142 A | 11/1982 | Schall, Jr. et al. |
| 4,363,634 A | 12/1982 | Schall, Jr. |
| 4,383,757 A | 5/1983 | Phillips |
| 4,390,343 A | 6/1983 | Walter |
| 4,423,099 A | 12/1983 | Mueller et al. |
| 4,450,150 A | 5/1984 | Sidman |
| RE31,712 E | 10/1984 | Giese |
| 4,478,822 A | 10/1984 | Haslam et al. |
| 4,478,914 A | 10/1984 | Giese |
| 4,481,137 A | 11/1984 | Ohnishi et al. |
| 4,487,839 A | 12/1984 | Kamentsky |
| 4,500,778 A | 2/1985 | Kusaka et al. |
| 4,508,832 A | 4/1985 | Carter et al. |
| 4,509,841 A | 4/1985 | Sakai et al. |
| 4,521,522 A | 6/1985 | Lundstrom et al. |
| 4,537,861 A | 8/1985 | Elings et al. |
| 4,540,881 A | 9/1985 | Hayashi et al. |
| 4,548,990 A | 10/1985 | Mueller et al. |
| 4,558,012 A | 12/1985 | Nygren et al. |
| 4,588,624 A | 5/1986 | Nygren et al. |
| 4,613,567 A | 9/1986 | Yasoshima et al. |
| 4,626,674 A | 12/1986 | Oinoue |
| 4,643,968 A | 2/1987 | Weaver |
| 4,655,595 A | 4/1987 | Bjork et al. |
| 4,657,543 A | 4/1987 | Langer et al. |
| 4,661,913 A | 4/1987 | Wu et al. |
| 4,663,296 A | 5/1987 | Revillet et al. |
| 4,693,884 A | 9/1987 | Kleiner et al. |
| 4,693,972 A | 9/1987 | Mansour et al. |
| 4,713,441 A | 12/1987 | Heller et al. |
| 4,716,123 A | 12/1987 | Wood |
| 4,752,567 A | 6/1988 | De Brabander et al. |
| 4,764,342 A | 8/1988 | Kelln et al. |
| 4,772,484 A | 9/1988 | Kitchell et al. |
| 4,778,758 A | 10/1988 | Ericsson et al. |
| 4,805,623 A | 2/1989 | Jobsis |
| 4,814,144 A | 3/1989 | Edelmann et al. |
| 4,857,313 A | 8/1989 | Song et al. |
| 4,876,208 A | 10/1989 | Gustafson et al. |
| 4,877,659 A | 10/1989 | Vince |
| 4,882,168 A | 11/1989 | Casey et al. |
| 4,885,077 A | 12/1989 | Karakelle et al. |
| 4,933,147 A | 6/1990 | Hollar et al. |
| 4,959,301 A | 9/1990 | Weaver et al. |
| 5,002,792 A | 3/1991 | Vegoe |
| RE33,581 E | 4/1991 | Nicoli et al. |
| 5,017,009 A | 5/1991 | Schutt et al. |
| 5,066,465 A | 11/1991 | Kano et al. |
| 5,079,144 A | 1/1992 | Carr et al. |
| 5,079,172 A | 1/1992 | Hari et al. |
| 5,082,630 A | 1/1992 | Partin et al. |
| 5,089,606 A | 2/1992 | Cole et al. |
| 5,149,543 A | 9/1992 | Cohen et al. |
| 5,173,164 A | 12/1992 | Egen et al. |
| 5,196,527 A | 3/1993 | Ookuma et al. |
| 5,208,037 A | 5/1993 | Wright et al. |
| 5,218,039 A | 6/1993 | Stoy et al. |
| 5,239,170 A | 8/1993 | Hughlett |
| 5,240,618 A | 8/1993 | Caldwell et al. |
| 5,288,611 A | 2/1994 | Kohne |
| 5,314,805 A | 5/1994 | Haugland et al. |
| 5,329,461 A | 7/1994 | Allen et al. |
| 5,350,697 A | 9/1994 | Swope et al. |
| 5,405,783 A | 4/1995 | Pirrung et al. |
| 5,466,416 A | 11/1995 | Ghaed et al. |
| 5,468,606 A | 11/1995 | Bogart et al. |
| 5,488,567 A | 1/1996 | Allen et al. |
| 5,491,097 A | 2/1996 | Ribi et al. |
| 5,494,829 A | 2/1996 | Sandstrom et al. |
| 5,496,701 A | 3/1996 | Pollard-Knight |
| 5,556,764 A | 9/1996 | Sizto et al. |
| 5,578,460 A | 11/1996 | Ebersole et al. |
| 5,599,668 A | 2/1997 | Stimpson et al. |
| 5,604,099 A | 2/1997 | Erlich et al. |
| 5,622,868 A | 4/1997 | Clarke et al. |
| 5,623,707 A | 4/1997 | Kusaka |
| 5,648,652 A | 7/1997 | Sekiya et al. |
| 5,656,432 A | 8/1997 | Claverys et al. |
| 5,789,173 A | 8/1998 | Peck et al. |
| 5,792,622 A | 8/1998 | Botsford |
| 5,824,494 A | 10/1998 | Feldberg |
| 5,828,716 A | 10/1998 | Bisconte de Saint Julien |
| 5,843,651 A | 12/1998 | Stimpson et al. |
| 5,849,486 A | 12/1998 | Heller et al. |
| 5,863,754 A | 1/1999 | Bajard |
| 5,866,345 A | 2/1999 | Wilding et al. |
| 5,872,013 A | 2/1999 | Leunissen et al. |
| 5,888,760 A | 3/1999 | Godsey et al. |
| 5,922,593 A | 7/1999 | Livingston |
| 5,939,291 A | 8/1999 | Loewy et al. |
| 5,958,704 A | 9/1999 | Starzl et al. |
| 5,976,821 A | 11/1999 | Huston et al. |
| 5,981,268 A | 11/1999 | Kovacs et al. |
| 5,993,634 A | 11/1999 | Simpson et al. |
| 6,017,696 A | 1/2000 | Heller |
| 6,043,048 A | 3/2000 | Johnston et al. |
| 6,051,380 A | 4/2000 | Sosnowski et al. |
| 6,054,270 A | 4/2000 | Southern |
| 6,086,824 A | 7/2000 | Fanning et al. |
| 6,096,272 A | 8/2000 | Clark et al. |
| 6,099,803 A | 8/2000 | Ackley et al. |
| 6,101,946 A | 8/2000 | Martinsky |
| 6,103,479 A | 8/2000 | Taylor |
| 6,107,054 A | 8/2000 | Gibbs |
| 6,122,599 A | 9/2000 | Mehta |
| 6,136,171 A | 10/2000 | Frazier et al. |
| 6,143,247 A | 11/2000 | Sheppard, Jr. et al. |
| 6,153,400 A | 11/2000 | Matsumura et al. |
| 6,153,416 A | 11/2000 | Yuan |
| 6,169,394 B1 | 1/2001 | Frazier et al. |
| 6,176,620 B1 | 1/2001 | Obara |
| 6,214,560 B1 | 4/2001 | Yguerabide et al. |
| 6,221,592 B1 | 4/2001 | Schwartz et al. |
| 6,241,894 B1 | 6/2001 | Briggs et al. |
| 6,242,188 B1 | 6/2001 | Dattagupta et al. |
| 6,245,508 B1 | 6/2001 | Heller et al. |
| 6,251,615 B1 | 6/2001 | Oberhardt |
| 6,251,616 B1 | 6/2001 | Barbera-Guillem et al. |
| 6,251,624 B1 | 6/2001 | Matsumura et al. |
| 6,264,825 B1 | 7/2001 | Blackburn et al. |
| 6,270,953 B1 | 8/2001 | Malcus-Vocanson et al. |
| 6,274,384 B1 | 8/2001 | Starzl et al. |
| 6,290,839 B1 | 9/2001 | Kayyem et al. |
| 6,372,895 B1 | 4/2002 | Bentsen et al. |
| 6,379,897 B1 | 4/2002 | Weidenhammer et al. |
| 6,391,264 B2 | 5/2002 | Hammer et al. |
| 6,391,546 B1 | 5/2002 | Karube et al. |

(56) References Cited

U.S. PATENT DOCUMENTS

| | | |
|---|---|---|
| 6,391,577 B1 | 5/2002 | Mikkelsen et al. |
| 6,391,937 B1 | 5/2002 | Beuhler et al. |
| 6,395,506 B1 | 5/2002 | Pitner et al. |
| 6,403,367 B1 | 6/2002 | Cheng et al. |
| 6,416,969 B2 | 7/2002 | Matsumura et al. |
| 6,432,694 B1 | 8/2002 | Malmqvist |
| 6,437,551 B1 | 8/2002 | Krulevitch et al. |
| 6,472,166 B1 | 10/2002 | Wardlaw et al. |
| 6,472,228 B2 | 10/2002 | Wang et al. |
| 6,548,263 B1 | 4/2003 | Kapur et al. |
| 6,551,841 B1 | 4/2003 | Wilding et al. |
| 6,565,727 B1 | 5/2003 | Shenderov |
| 6,573,088 B2 | 6/2003 | Gemmell et al. |
| 6,596,532 B1 | 7/2003 | Hyman et al. |
| 6,605,453 B2 | 8/2003 | Ozkan et al. |
| 6,607,888 B2 | 8/2003 | Schwartz et al. |
| 6,611,765 B2 | 8/2003 | Boeufgras et al. |
| 6,642,682 B1 | 11/2003 | Perkins et al. |
| 6,696,286 B1 | 2/2004 | Halverson et al. |
| 6,703,819 B2 | 3/2004 | Gascoyne |
| 6,716,620 B2 | 4/2004 | Bashir et al. |
| 6,809,862 B2 | 10/2004 | Behnsen et al. |
| 6,841,379 B2 | 1/2005 | Matson |
| 6,844,028 B2 | 1/2005 | Mao et al. |
| 6,872,545 B2 | 3/2005 | Griner et al. |
| 6,900,030 B2 | 5/2005 | Pitner et al. |
| 6,951,714 B2 | 10/2005 | Giovannoni et al. |
| 7,067,194 B2 | 6/2006 | Mao et al. |
| 7,108,775 B2 | 9/2006 | Bahatt et al. |
| 7,115,384 B2 | 10/2006 | Clark et al. |
| 7,123,345 B2 | 10/2006 | Sugihara et al. |
| 7,214,299 B2 | 5/2007 | Armstrong |
| 7,250,775 B1 | 7/2007 | Collins et al. |
| 7,258,837 B2 | 8/2007 | Yager et al. |
| 7,306,924 B2 | 12/2007 | Gomez et al. |
| 7,341,841 B2 | 3/2008 | Metzger et al. |
| 7,348,183 B2 | 3/2008 | Fritsch et al. |
| 7,397,540 B2 | 7/2008 | Lundgren et al. |
| 7,413,891 B2 | 8/2008 | Bashir et al. |
| 7,429,355 B2 | 9/2008 | Bishop et al. |
| 7,435,579 B2 | 10/2008 | Bashir et al. |
| 7,451,646 B2 | 11/2008 | Cleland et al. |
| 7,481,977 B2 | 1/2009 | Percival et al. |
| 7,510,637 B2 | 3/2009 | Barlow et al. |
| 7,561,789 B2 | 7/2009 | Border et al. |
| 7,564,245 B2 | 7/2009 | Lee |
| 7,576,307 B2 | 8/2009 | Yazdanfar et al. |
| 7,601,300 B2 | 10/2009 | Blanton et al. |
| 7,622,078 B2 | 11/2009 | Pinyol |
| 7,629,029 B2 | 12/2009 | Mao et al. |
| 7,642,068 B2 | 1/2010 | Steiner et al. |
| 7,651,837 B2 | 1/2010 | Ohno et al. |
| 7,670,793 B2 | 3/2010 | Glencross |
| 7,678,256 B2 | 3/2010 | Davalos et al. |
| 7,687,239 B2 | 3/2010 | Goldberg et al. |
| 7,689,022 B2 | 3/2010 | Weiner et al. |
| 7,723,095 B2 | 5/2010 | Cleuziat et al. |
| 7,754,148 B2 | 7/2010 | Yu et al. |
| 7,829,275 B2 | 11/2010 | Franzen et al. |
| 7,842,504 B2 | 11/2010 | Devlin, Sr. |
| 7,873,268 B2 | 1/2011 | Segawa et al. |
| 7,901,624 B2 | 3/2011 | Hansen et al. |
| 7,910,062 B2 | 3/2011 | Yu et al. |
| 7,955,555 B2 | 6/2011 | Blecka et al. |
| 8,014,583 B2 | 9/2011 | Zahniser |
| 8,029,746 B2 | 10/2011 | Yu et al. |
| 8,058,078 B2 | 11/2011 | Hansen et al. |
| 8,071,319 B2 | 12/2011 | Metzger et al. |
| 8,102,276 B2 | 1/2012 | Sugiura |
| 8,168,443 B2 | 5/2012 | Yu et al. |
| 8,178,602 B2 | 5/2012 | Mao et al. |
| 8,188,438 B2 | 5/2012 | Li |
| 8,304,245 B2 | 11/2012 | Kuypers et al. |
| 8,323,466 B2 | 12/2012 | Kim et al. |
| 8,329,437 B1 | 12/2012 | Ayliffe |
| 8,335,393 B2 | 12/2012 | Kotani |
| 8,354,307 B2 | 1/2013 | Lee |
| 8,361,298 B2 | 1/2013 | Sabin et al. |
| 8,361,299 B2 | 1/2013 | Sabin et al. |
| 8,364,409 B2 | 1/2013 | Rieder et al. |
| 8,368,964 B2 | 2/2013 | Xu et al. |
| 8,372,353 B2 | 2/2013 | Lee et al. |
| 8,372,600 B2 | 2/2013 | Sachs et al. |
| 8,391,582 B2 | 3/2013 | Weiner et al. |
| 8,421,484 B2 | 4/2013 | Prodan et al. |
| 8,460,887 B2 | 6/2013 | Goldberg et al. |
| 8,478,445 B2 | 7/2013 | Hansen et al. |
| 8,481,281 B2 | 7/2013 | Demirev et al. |
| 8,508,652 B2 | 8/2013 | Albu et al. |
| 8,512,636 B2 | 8/2013 | Blanton et al. |
| 8,513,001 B2 | 8/2013 | Weiss et al. |
| 8,563,298 B2 | 10/2013 | Lowery, Jr. et al. |
| 8,603,769 B2 | 12/2013 | Feng et al. |
| 8,614,056 B2 | 12/2013 | Davis et al. |
| 8,635,028 B2 | 1/2014 | Sengupta et al. |
| 8,647,835 B2 | 2/2014 | Walsh et al. |
| 8,652,800 B2 | 2/2014 | Walsh et al. |
| 8,703,061 B2 | 4/2014 | Guzman |
| 8,709,344 B2 | 4/2014 | Bishop et al. |
| 8,765,062 B2 | 7/2014 | Linder et al. |
| 8,779,779 B2 | 7/2014 | Wang et al. |
| 8,780,181 B2 | 7/2014 | Olesen et al. |
| 8,804,105 B2 | 8/2014 | Ayliffe |
| 8,821,814 B2 | 9/2014 | Cho et al. |
| 8,828,680 B2 | 9/2014 | Williams et al. |
| 8,841,118 B2 | 9/2014 | Robinson et al. |
| 8,895,255 B1 | 11/2014 | Goldberg et al. |
| 8,911,987 B2 | 12/2014 | Robinson et al. |
| 8,932,523 B2 | 1/2015 | Linder et al. |
| 8,943,588 B1 | 1/2015 | Speegle et al. |
| 8,969,072 B2 | 3/2015 | Robinson et al. |
| 8,970,826 B2 | 3/2015 | Liu et al. |
| 9,007,233 B2 | 4/2015 | Sugiura |
| 9,048,771 B2 | 6/2015 | Ohba et al. |
| 9,057,714 B2 | 6/2015 | Gomm et al. |
| 9,090,462 B2 | 7/2015 | Straus |
| 9,133,498 B2 | 9/2015 | Kwon et al. |
| 9,150,900 B2 | 10/2015 | Bishop et al. |
| 9,213,043 B2 | 12/2015 | Cook et al. |
| 9,248,422 B2 | 2/2016 | Ching et al. |
| 9,274,132 B2 | 3/2016 | Wilson et al. |
| 9,290,382 B2 | 3/2016 | Straus |
| 9,353,396 B2 | 5/2016 | Demirev et al. |
| 9,405,288 B2 | 8/2016 | Ogata |
| 9,434,937 B2 | 9/2016 | Metzger et al. |
| 9,567,621 B2 | 2/2017 | Robinson et al. |
| 9,657,327 B2 | 5/2017 | Metzger et al. |
| 9,677,109 B2 | 6/2017 | Shamsheyeva et al. |
| 9,714,420 B2 | 7/2017 | Metzger et al. |
| 9,841,422 B2 | 12/2017 | Goldberg et al. |
| 10,202,597 B2 | 2/2019 | Metzger et al. |
| 10,253,355 B2 | 4/2019 | Richards et al. |
| 10,254,204 B2 | 4/2019 | Prisbrey et al. |
| 10,273,521 B2 | 4/2019 | Ashby et al. |
| 2001/0009774 A1 | 7/2001 | Shin et al. |
| 2001/0053535 A1 | 12/2001 | Bashir et al. |
| 2002/0028489 A1 | 3/2002 | Ammann et al. |
| 2002/0028519 A1 | 3/2002 | Yguerabide et al. |
| 2002/0031795 A1 | 3/2002 | James et al. |
| 2002/0119455 A1 | 8/2002 | Chan |
| 2002/0127144 A1 | 9/2002 | Mehta |
| 2002/0148729 A1 | 10/2002 | Armstrong |
| 2002/0155490 A1 | 10/2002 | Skinner et al. |
| 2002/0155591 A1 | 10/2002 | Farina et al. |
| 2002/0164677 A1 | 11/2002 | Giovannoni et al. |
| 2002/0197709 A1 | 12/2002 | Van der Weide et al. |
| 2003/0023149 A1 | 1/2003 | Montemagno et al. |
| 2003/0032171 A1 | 2/2003 | Gemmell et al. |
| 2003/0032173 A1 | 2/2003 | Farina et al. |
| 2003/0036054 A1 | 2/2003 | Ladisch et al. |
| 2003/0119028 A1 | 6/2003 | Graves et al. |
| 2003/0124623 A1 | 7/2003 | Yager et al. |
| 2003/0134269 A1 | 7/2003 | Hairai et al. |
| 2003/0147132 A1 | 8/2003 | Behnsen et al. |

(56) References Cited

U.S. PATENT DOCUMENTS

| | | |
|---|---|---|
| 2003/0153023 A1 | 8/2003 | Starzl et al. |
| 2003/0157587 A1 | 8/2003 | Gomez et al. |
| 2003/0170613 A1 | 9/2003 | Straus |
| 2003/0186341 A1 | 10/2003 | Kuhn et al. |
| 2003/0211566 A1 | 11/2003 | Gazenko |
| 2003/0224436 A1 | 12/2003 | Nelson et al. |
| 2004/0052426 A1 | 3/2004 | Landesman |
| 2004/0089546 A1 | 5/2004 | Bahatt et al. |
| 2004/0168916 A1 | 9/2004 | Fuchs et al. |
| 2004/0189311 A1 | 9/2004 | Glezer et al. |
| 2005/0048599 A1 | 3/2005 | Goldberg et al. |
| 2005/0059105 A1 | 3/2005 | Alocija et al. |
| 2005/0112544 A1 | 5/2005 | Xu et al. |
| 2005/0114041 A1 | 5/2005 | Gawad et al. |
| 2005/0118705 A1 | 6/2005 | Rabbitt et al. |
| 2005/0121596 A1 | 6/2005 | Kam et al. |
| 2005/0202523 A1 | 9/2005 | Shaw et al. |
| 2005/0208592 A1 | 9/2005 | Caron et al. |
| 2005/0213374 A1 | 9/2005 | Xu et al. |
| 2005/0221403 A1 | 10/2005 | Gazenko |
| 2005/0238652 A1 | 10/2005 | Tsuji et al. |
| 2005/0255445 A1 | 11/2005 | Van Damme et al. |
| 2005/0287572 A1 | 12/2005 | Mathies et al. |
| 2006/0120916 A1 | 6/2006 | Kolari et al. |
| 2006/0141618 A1 | 6/2006 | Yasuda et al. |
| 2006/0166184 A1 | 7/2006 | Yasuda et al. |
| 2006/0194307 A1 | 8/2006 | Yasuda et al. |
| 2006/0243594 A1 | 11/2006 | Schnelle et al. |
| 2007/0037225 A1 | 2/2007 | Metzger et al. |
| 2007/0202538 A1 | 8/2007 | Glezer et al. |
| 2007/0238146 A1 | 10/2007 | Tyler et al. |
| 2007/0298513 A1 | 12/2007 | Starzl et al. |
| 2008/0014181 A1 | 1/2008 | Ariff et al. |
| 2008/0046286 A1 | 2/2008 | Halsted |
| 2008/0072664 A1 | 3/2008 | Hansen et al. |
| 2008/0138799 A1 | 6/2008 | Cheng et al. |
| 2008/0193965 A1 | 8/2008 | Zeng et al. |
| 2008/0221805 A1 | 9/2008 | Andrews |
| 2008/0241858 A1 | 10/2008 | Metzger et al. |
| 2009/0012723 A1 | 1/2009 | Treado et al. |
| 2009/0051372 A1 | 2/2009 | Sethu et al. |
| 2009/0104689 A1 | 4/2009 | Kim et al. |
| 2009/0203063 A1 | 8/2009 | Wheeler et al. |
| 2009/0208072 A1 | 8/2009 | Seibel et al. |
| 2010/0048428 A1 | 2/2010 | Coyer et al. |
| 2010/0075340 A1 | 3/2010 | Javanmard |
| 2010/0099139 A1 | 4/2010 | Ben-David et al. |
| 2010/0120016 A1 | 5/2010 | Li et al. |
| 2010/0129858 A1 | 5/2010 | Walsh et al. |
| 2010/0248281 A1 | 9/2010 | Straus |
| 2010/0267165 A1 | 10/2010 | Bruls et al. |
| 2011/0023690 A1 | 2/2011 | Wilson |
| 2011/0042582 A1 | 2/2011 | Ingber et al. |
| 2011/0117577 A1 | 5/2011 | Reboud et al. |
| 2011/0136165 A1 | 6/2011 | Vojnovic et al. |
| 2011/0183856 A1 | 7/2011 | Agan et al. |
| 2011/0237446 A1 | 9/2011 | Treado et al. |
| 2011/0242308 A1 | 10/2011 | Igarashi et al. |
| 2011/0256617 A1 | 10/2011 | Cocchi et al. |
| 2012/0028342 A1 | 2/2012 | Ismagilov et al. |
| 2012/0077206 A1 | 3/2012 | Metzger et al. |
| 2012/0103817 A1 | 5/2012 | Omori et al. |
| 2012/0105837 A1 | 5/2012 | Ingber |
| 2012/0142032 A1 | 6/2012 | Morgan |
| 2012/0149584 A1 | 6/2012 | Olle |
| 2012/0169863 A1 | 7/2012 | Bachelet et al. |
| 2012/0223217 A1 | 9/2012 | Zheng et al. |
| 2012/0244519 A1 | 9/2012 | Olesen et al. |
| 2012/0258874 A1 | 10/2012 | Narain et al. |
| 2013/0017534 A1 | 1/2013 | Nickel et al. |
| 2013/0045878 A1 | 2/2013 | McCue |
| 2013/0089886 A1 | 4/2013 | Feng et al. |
| 2013/0115607 A1 | 5/2013 | Nielsen et al. |
| 2013/0183694 A1 | 7/2013 | Janetzko et al. |
| 2013/0217063 A1 | 8/2013 | Metzger et al. |
| 2013/0271060 A1 | 10/2013 | Messersmith et al. |
| 2013/0295588 A1 | 11/2013 | Watkins et al. |
| 2013/0295597 A1 | 11/2013 | DeWitte et al. |
| 2013/0324437 A1 | 12/2013 | Pogliano et al. |
| 2013/0345525 A1 | 12/2013 | Kline |
| 2014/0038171 A1 | 2/2014 | Metzger et al. |
| 2014/0179726 A1 | 6/2014 | Bajaj et al. |
| 2014/0199719 A1 | 7/2014 | Shih et al. |
| 2014/0234949 A1 | 8/2014 | Wasson et al. |
| 2014/0278136 A1 | 9/2014 | Shamsheyeva et al. |
| 2014/0278143 A1 | 9/2014 | Garstecki et al. |
| 2014/0323340 A1 | 10/2014 | Goldberg et al. |
| 2014/0343868 A1 | 11/2014 | Colwell et al. |
| 2015/0168290 A1 | 6/2015 | Shachaf |
| 2015/0225762 A1 | 8/2015 | Metzger et al. |
| 2015/0293270 A1 | 10/2015 | Jarvius et al. |
| 2015/0301002 A1 | 10/2015 | DeWitte et al. |
| 2015/0337351 A1 | 11/2015 | Metzger |
| 2016/0010138 A1 | 1/2016 | Shamsheyeva et al. |
| 2016/0051985 A1 | 2/2016 | Knight et al. |
| 2016/0238826 A1 | 8/2016 | Shields et al. |
| 2016/0279633 A1 | 9/2016 | Bachelet et al. |
| 2016/0289729 A1 | 10/2016 | Richards et al. |
| 2016/0348091 A1 | 12/2016 | Metzger et al. |
| 2017/0023599 A1 | 1/2017 | Richards et al. |
| 2017/0029864 A1 | 2/2017 | Straus |
| 2017/0234781 A1 | 8/2017 | Prisbrey et al. |
| 2018/0080932 A1 | 3/2018 | Goldberg et al. |
| 2018/0135093 A1 | 5/2018 | Ashby et al. |

FOREIGN PATENT DOCUMENTS

| | | |
|---|---|---|
| EP | 1648286 | 4/2006 |
| EP | 2 645 108 A1 | 10/2013 |
| EP | 2 987 851 A1 | 2/2016 |
| EP | 2 507 663 B1 | 2/2017 |
| GB | 1520733 | 8/1978 |
| JP | 52102491 | 8/1977 |
| JP | 58198759 | 11/1983 |
| JP | H11505405 | 5/1999 |
| JP | 2001509008 | 7/2001 |
| JP | 2002500892 | 1/2002 |
| JP | 2002502597 | 1/2002 |
| JP | 2002330799 | 11/2002 |
| JP | 2003527601 | 9/2003 |
| JP | 200481019 | 3/2004 |
| JP | 2004513628 | 5/2004 |
| WO | WO 1989001162 | 2/1989 |
| WO | WO 8910566 A1 | 11/1989 |
| WO | WO 1990011525 | 10/1990 |
| WO | WO 1991004491 | 4/1991 |
| WO | WO 1993013197 | 7/1993 |
| WO | WO 1994002831 | 2/1994 |
| WO | WO 1994011728 | 5/1994 |
| WO | WO 1995008640 | 3/1995 |
| WO | WO 1995028641 | 10/1995 |
| WO | WO 1996014431 | 5/1996 |
| WO | WO 1998022618 | 5/1998 |
| WO | WO 1998022808 | 5/1998 |
| WO | WO 1998040741 | 9/1998 |
| WO | WO 1999020789 | 4/1999 |
| WO | WO 1999037799 | 7/1999 |
| WO | WO 1999040174 | 8/1999 |
| WO | WO 1999058948 | 11/1999 |
| WO | WO 2000024941 | 5/2000 |
| WO | WO 2001031332 | 5/2001 |
| WO | WO 2001069230 | 9/2001 |
| WO | WO 2001079529 A1 | 10/2001 |
| WO | WO 2002038724 | 5/2002 |
| WO | WO 2003012525 A1 | 2/2003 |
| WO | WO 2003022999 | 3/2003 |
| WO | WO 2003025208 | 3/2003 |
| WO | WO 2003048736 | 6/2003 |
| WO | WO 2003065009 | 8/2003 |
| WO | WO 2003073100 | 9/2003 |
| WO | WO 2005027714 | 3/2005 |
| WO | WO 2006015374 | 2/2006 |
| WO | WO 2006028601 A2 | 3/2006 |
| WO | WO 2006066216 | 6/2006 |

(56) References Cited

FOREIGN PATENT DOCUMENTS

| | | |
|---|---|---|
| WO | WO 2006113930 A2 | 10/2006 |
| WO | WO 2006135904 | 12/2006 |
| WO | WO 2009124068 | 10/2009 |
| WO | WO 2010062350 | 6/2010 |
| WO | WO 2010062352 | 6/2010 |
| WO | WO 2011/035304 A2 | 3/2011 |
| WO | WO 2012122314 | 9/2012 |
| WO | WO 2012162133 | 11/2012 |
| WO | WO 2013072069 A1 | 5/2013 |
| WO | WO 2013/130875 A1 | 9/2013 |
| WO | WO 2013/177277 A1 | 11/2013 |
| WO | WO 2014040088 | 3/2014 |
| WO | WO 2014100456 | 6/2014 |
| WO | WO 2014145899 | 9/2014 |
| WO | WO 2014153194 | 9/2014 |
| WO | WO 2014169921 A1 | 10/2014 |
| WO | WO 2016/037051 A1 | 3/2016 |
| WO | WO2016207065 A1 | 12/2016 |

OTHER PUBLICATIONS

Joux et al., "Use of fluorescent probes to assess physiological functions of bacteria at single-cell level," *Microb Infect.* 2:1523-1535, 2000.
Makinen et al., "Evaluation of a novel strip test, Geno Type Mycobacterium CM/AS, for species identification of mycobacterial cultures," *Clin Microbiol Infect.* 12: 481-483, 2006.
Makinen et al., "2, Comparison of Two Commercially Available DNA Line Probe Assays for Detection of Multidrug-Resistant *Mycobacterium tuberculosis,*" *J Clin Microbiol* 44:350-352, 2006.
Walz et al, Synthesis and studies of catechol-containing mycobactin S and T analogs, *Org Biomol Chem.* 5:1621-1628, 2007.
Bloem et al., "Fully Automatic Determination of Soil Bacterium Numbers, Cell Volumes, and Frequencies of Dividing Cells by Confocal Laser Scanning Microscopy and Image Analysis," *Appl Environ Microbiol.* 61:926-936, 1995.
EP 16200084.8 Extended European Search Report dated Aug. 1, 2017 (17 pages).
Pagola et al., "The structure of malaria pigment β-haematin," *Nature* 404:301-310, 2000.
Bello, M., "Electrolytic modification of a buffer during a capillary electrophoresis run," *J Chromatogr.* 744:81-91, 1996.
Jiang et al., "Human Adenoviruses and Coliphages in Urban Runoff-Impacted Coastal Waters of Southern California," *App Environ Micriobiol.* 67:179-184, 2001.
Alban et al., "A novel experimental design for comparative two-dimensional gel analysis: Two-dimensional difference gel electrophoresis incorporating a pooled internal standard," *Proteomics* 3:36-44, 2003.
Olsvik et al., "Magnetic Separation Techniques in Diagnostic Microbiology", *Clin Microbiol Rev.* 7:43-54, 1994.
Accelerate Diagnostics: "Accelerate ID/AST," Vimeo, May 18, 2015, pp. 1-6, XP054976621, Retrieved from the Internet: URL:https://vimeo.com/128112270 [retrieved on Jun. 22, 2016].
Accelerate Diagnostics: "Fast Phenotypic Antibiotic Susceptibility Testing: Connie Price, M.D.," YouTube, Aug. 28, 2015, pp. 1-6, XP054976622, Retrieved from the Internet: URL:https://www.youtube.com/watch?v=ln1GW54atXE&index=3&list=PLsmqpsknnk2_ENp8Xd3BhK0vu9nfU0p6y [retrieved on Jun. 22, 2016].
Alere, Inc., "Adult Isolator Tube Solution Material Safety Data Sheet," (2010).
Aminian et al., "A Conformal Bayesian Network for Classification of *Mycobacterium tuberculosis* Complex Lineages," BMC Bioinformatics, 11 (Suppl 3): S4 (2010).
Anzaldi et al., "Overcoming the Heme Paradox: Heme Toxicity and Tolerance in Bacterial Pathogens," Infect. Immun. 78(12): 4977-4989 (2010).
Ateya et al., "Volume Cytometry: Microfluidic Sensor for High-Throughput Screening in Real Time," Analytical Chem., 77:1290-1294, (2005).

Atlas and Snyder, Handbook of Media for Clinical Microbiology, 2006. CRC press.
Bae et al., "Immunosensor for Detection of Yersinia Enterocolitica Based on Imaging Ellipsometry," Analytical Chem., 76:1799-1803, (2004).
Baker et al., "The Bactericidal Action of Synthetic Detergents," J Exp Med. 74:611620, 1941.
Balaban et al., "Bacterial Persistence as a Phenotypic Switch," Science, 305, pp. 1622-1625, (2004).
Barton et al., "Measurement of Bacterial Growth Rates on Polymers," J. Biomed. Mater Res., 32, pp. 271-278, (1996).
Bayoudh et al., "Electrical Detection and Characterization of Bacterial Adhesion Using Electrochemical Impedance Spectroscopy-Based Flow Chamber," Colloids and Surfaces A: Physicochem. Eng. Aspects, 318:291-300, (2008).
Beaglehole, "Performance of a Microscopic Imaging Ellipsometer," Rev. Sci. Instrum., 59:12, pp. 2557-2559, (1988).
Belding et al., "Effect of Sodium Polyanetholesulfonate on Antimicrobial Systems in Blood," Appl. Microbiol. 24(5): 691-698 (1972).
Benecky et al., "Simultaneous Detection of Multiple Analytes Using Copalis Technology: A Reduction to Practice," Clin. Chem., 44:9, pp. 2052-2054, (1998).
Boehm et al., "On-Chip Microfluidic Biosensor for Bacterial Detection and Identification," Sensors and Actuators, 126:508-514, (2007).
Bridson, E.Y., and Gould, G.W., "Quantal Microbiology," Lett. Appl. Microbiology, 30:95-98, (2000).
Burnham C-1358: Poster—"Rapid Detection of *Klebsiella pneumoniae* Carbapenemase (KPC) Producing Isolates Using the BACcel™ Digital Microscopy System," Presented at ASM 2013 May 18, 2013, Denver, CO.
Burnham et al., "Rapid Ertapenem Susceptibility Testing and *Klebsiella pneumoniae* Carbapenemase (KPC) Phenotype Detection in *Klebsiella pneumoniae* Using Automated Microscopy of Immobilized Live Bacterial Cells," *J Clin Microbiol*. 52:982-986, 2014.
Cabrera et al., "Continuous Concentration of Bacteria in a Microfluidic Flow Cell Using Electrokinetic Techniques," *Electrophoresis* 22:355-362, 2001.
Chan et al., "Evaluation of Lysis Filtration as an Adjunct to Conventional Blood Culture," J. Clin. Pathol. 39: 89-92 (1986).
Cheung et al., "Microfluidic Impedance-Based Flow Cytometry," Cytometry A, 77A, pp. 648-666, (2010).
Choi et al., "Rapid antibiotic susceptibility testing by tracking single cell growth in a microfluidic agarose channel system," *Lab Chip* 13:280-287, 2013.
Cooper et al. D-4013: Poster—"Potential Impact of Rapid Phenotype Identification on Antimicrobial Prescribing," Presented at the 48th ICAAC and IDSA Oct. 28, 2008, Washington, DC.
Dai et al., "Electrokinetic Trapping and Concentration Enrichment of DNA in a Microfluidic Channel," J. Am. Chem. Soc., 125"13026-13027, (2003).
Daims et al., "Quantification of Uncultured Microorganisms by Fluorescence Microscopy and Digital Image Analysis," Appl. Microbiol. Biotechnol., 75"237-248, (2007).
De Brabander et al., "Detection of Gold Probes With Video-Enhanced Contrast Microscopy: Nanovid Microscopy," Amer. J., Anat. 185:282-295, (1989).
Delehanty, J.B., and Ligler, F.S., "A Microarray Immunoassay for Simultaneous Detection of Proteins and Bacteria," Anal. Chem., 74:5681-5687, (2002).
Desai, M.J., and Armstrong, D.W., "Separation, Identification, and Characterization of Microorganisms by Capillary Electrophoresis," Microbiology and Molecular Biology Reviews, 67, pp. 38-51, (2003).
Dorn et al., "Blood Culture Technique Based on Centrifugation: Developmental Phase," J. Clin. Micro. 3(3): 251-257 (1976).
Douglas et al. Poster—"Rapid Microbiological Identification and Major Drug Resistance Phenotyping with Novel Multiplexed Automated Digital Microscopy (MADM) for Ventilator-Associated Pneumonia (VAP) Surveillance," Presented at ATS May 16, 2011, 2011, Denver, CO.

(56) References Cited

OTHER PUBLICATIONS

Douglas et al., Rapid Automated Microscopy for Microbiological Surveillance of Ventilator-associated Pneumonia, Am J Respir Crit Care Med. 191:566-573, 2015.
Dwek et al., "Synchronization of Cell Division in Microorganisms by Percoll Gradients," J. Bacteriol. 144(1):17-21 (1980).
Elfwing et al., "Observing Growth and Division of Large Numbers of Individual Bacteria by Image Analysis," Appl. Environ. Micro., 70, pp. 675-678, (2004).
Elghanian et al., "Selective Colorimetric Detection of Polynucleotides Based on the Distance-Dependent Optical Properties of Gold Nanoparticles," Science, 277, pp. 1078-1081, (1997).
Ertl et al., "Electrochemical Biosensor Array for the Identification of Microorganisms Based on Lectin-Lipopolysaccharide Recognition," Analytical Chem., 73: 4241-4248, (2001).
Ertl et al., "Rapid Identification of Viable *Escherichia coli* Subspecies with Electrochemical Screen-Printed Biosensor Array," Biosensors Bioelectronics, 18, pp. 907-916, (2003).
Eun et al., "Encapsulating Bacteria in Agarose Microparticles Using Microfluidics for High-Throughput Cell Analysis and Isolation," ACS Chem. Biol., 18:260-266, (2011).
Fesenko et al., "Biosensing and Monitoring of Cell Populations Using the Hydrogel Bacterial Microchip," Biosens Bioelectron. 20:1860-1865, 2005.
Forero et al., "Automatic Identification Techniques of Tuberculosis Bacteria," Proc. SPIE 5203, Applications of Digital Image Processing XXVI. (Tescher, A.G., Ed.) SPIE Proceedings, 5203:71-81, (2003).
Friedman et al., "Precise Temporal Modulation in the Response of the SOS DNA Repair Network in Individual Bacteria," PLoS Bio. 3:1261-1268, (2005).
Gadkari, "Optimal Hydrogels for Fast and Safe Delivery of Bioactive Compounds," A Thesis Submitted to the Faculty of Drexel University, (2007).
Gamage et al. 2556: Poster—"Rapid Detection of Clinically Important *Staphylococcus aureus* Resistance Phenotypes Directly from Positive Blood Cultures Using Automated Microscopy," Presented at ASM2014 May 20, 2014, Boston, MA.
Gao et al., "Epipolarization Microscopic Immunogold Assay: A Combination of Immunogold Silver Stainins, ELISA and Epipolarization Microscopy," Biotech. & Histochem., 70:211-216, (1995).
Gast, R.K. et al., "Detection of *Salmonella entertidis* in Incubated Pools of Egg Contents by Fluorescence Polarization and Lateral Flow Immunodiffusion," Poultry Science, 82:687-690, (2003).
Gawad et al., "Micromachined Impedance Spectroscopy Flow Cytometer for Cell Analysis and Particle Sizing," Lab on a Chip, 1, pp. 76-82, (2001).
Geerts et al., "Nanovid Microscopy," Nature, 1991, 351:765-766, (1991).
Geesey, and White, "Determination of Bacterial Growth and Activity at Solid-Liquid Interfaces," Annu. Rev. Microbiol., 44:579-602, (1990).
Gomez et al., "Microfluidic Biochip for Impedance Spectroscopy of Biological Species," Biomedical Microdevices, 3:3, pp. 201-209, (2001).
Greef et al., "Identification and Growth Rate Quantitation of Individual Bacterial Clones Using a Novel Microfluidic Concentration Device," Accelr8 Technology Corporation (1 page), 2006.
Hach Company, "Heterotrophic Bacteria, Pour Plate Method," Edition 7 (10 pages), 2012.
Hance et al. C-065: Poster - "A Rapid Indirect Enzyme-Linked Immunosorbent Assay for Identification of *Acinetobacter* spp. from Cultured Isolates," Presented at the American Society for Microbiology 108th General Meeting Jun. 2, 2008.
Hance et al. K-392: Poster—"Rapid Identification of Live *Acinetobacter* spp. in Bronchoalveolar Lavage Specimens by Automated Immunofluorescence Microscopy," Presented at the 47th ICAAC Sep. 27, 2007.
Hance et al. P0539: Poster—"Pathogen Identification from Positive Blood Cultures Using Automated Sample Preparation and Automated Fluorescent in situ Hybridization (FISH)," Presented at ECCMID 2014, May 11, 2014, Barcelona, Spain.
Hance et al. Poster 2032: Poster—"Rapid Bacterial Identification Directly from Positive Blood Cultures Using Automated Sample Preparation and Multiplexed Fluorescence in situ Hybridization (FISH)," ASM2014, Boston, MA May 20, 2014.
Heileman et al., "Dielectric Spectroscopy as a Viable Biosensing Tool for Cell and Tissue Characterization and Analysis," Biosensors and Bioelectronics, 49, pp. 348-359, (2013).
Huang et al., "Electric Manipulation of Bioparticles and Macromolecules on Microfabricated Electrodes," Analytical Chem., 73, pp. 1549-1559, (2001).
Huang et al., "Lysozyme for Capture of Microorganisms on Protein Biochips," Enzyme and Microbial. Technol., 33:958-966, (2003).
Inverness Medical Group, "Wampole Isostat Microbial Tubes, Instructions for Use and Supplementary Application Notes," (2008).
Iregui et al., "Clinical Importance of Delays in the Initiation of Appropriate Antibiotic Treatment for Ventilator-Associated Pneumonia," *Chest* 122:262-268, 2002.
Isse et al., "Digital Transplantation Pathology: Combining Whole Slide Imaging, Multiplex Staining and Automated Image Analysis," *Am J Transplant.* 12:21-31, 2012.
Jampachaisri et al., "Classification of oligonucleotide fingerprints: application for microbial community and gene expression analyses," Bioinformatics 21: 3122-3130 (2005).
Ji et al., "Real-time Detection of Bacterial Contamination in Dynamic Aqueous Environments Using Optical Sensors." Analytical Chem., 76:1411-1418, (2004).
Jin et al., "A Biosensor Concept Based on Imaging Ellipsometry for Visualization of Biomolecular Interactions," Analytical Biochem., 232:69-72, (1995).
Kastenholz, B. "Comparison of the Electrochemical Behavior of the High Molecular Mass Cadmium Proteins in *Arabidopsis thaliana* and in Vegetable Plants on Using Preparative Native Continuous Polyacrylamide Gel Electrophoresis (PNC-PAGE)," Electroanalysis 18:103-106 (2006).
Kim and Soh, "Simultaneous Sorting of Multiple Bacterial Targets Using Integrated Dielectrophoretic-Magnetic Activated Cell Sorter," Lab Chip 9:2313-2318, 2009.
Kim et al., "Programmed Trapping of Individual Bacteria Using Micrometre-Size Sieves," Lab on a Chip, 11, pp. 1089-1095, (2011).
Koh et al., "Integrating Polymerase Chain Reaction, Valving, and Electrophoresis in a Plastic Device for Bacterial Detection," Analytical Chem., 75:4591-4598, (2003).
Kremser, et al., "Capillary Electrophoresis of Biological Particles: Viruses, Bacteria, and Eukaryotic Cells," Electrophoresis 25: 2282-2291 (2004).
Kubitschko et al., "Sensitivity Enhancement of Optical Immunosensors with Nanoparticles," Analytical Biochem., 253, pp. 112-122, (1997).
Kuehn et al., "Automated Confocal Laser Scanning Microscopy and Semiautomated Image Processing for Analysis of Biofilms," Appl. Environ. Microbio., 64:4115-4127, (1998).
Kumar et al., "Duration of Hypotension Before Initiation of Effective Antimicrobial Therapy is the Critical Determinant of Survival in Human Septic Shock," *Crit Care Med.* 34:1589-1596, 2006.
Lagally et al., "Integrated Portable Genetic Analysis Microsystem for Pathogen/Infectious Disease Detection," Analytical Chem., 76, pp. 3162-3170, (2004).
Lawrence et al., "Computer-Enhanced Darkfield Microscopy for the Quantitative Analysis of Bacterial Growth and Behavior on Surfaces," J. Microbial. Methods 10:123-138, (1989).
Lerner, "Bayesian Fluorescence In Situ Hybridisation Signal Classification," Artif. Intell. Med. 30: 301-316 (2004).
\ Levin-Reisman et al., "Automated Imagining With ScanLag Reveals Previously Undetectable Bacterial Growth Phenotypes," *Nature Methods* 7:737-739, 2010.
Lisby et al. EPoster "Performance of the new Accelerate ID/AST System in Highly Resistant *Acinetobacter baumannii* Bloodstream Infection Isolates, Compared to Routine Laboratory Testing," ECCMID Apr. 23, 2015, Copenhagen, Denmark.

(56) References Cited

OTHER PUBLICATIONS

Liu et al., "CMEIAS: A Computer-Aided System for the Image Analysis of Bacterial Morphotypes in Microbial Communities," Microb. Ecol., 41:173-194, (2001).
Lloyd, D., and Hayes, A.L, "Vigour, Vitality and Viability of Microorganisms," FEMS Microbio. Lett., 133:1-7, (1995).
Lochhead, "Microfluidic Devices that Capture Bacteria for Growth and Kill Analysis," Nov. 14, 2006, XP055207195, retrieved from the Internet: URL:http://acceleratediagnostics.com/docs/AVS_2006_Capture.pdf [retrieved on Aug. 11, 2015].
Luna et al., "Appropriateness and Delay to Initiate Therapy in Ventilator-Associated Pneumonia," *Eur Respir J.* 27:158-164, 2006.
Maeyama et al., "Confocal Imaging of Biofilm Formation Process Using Fluoroprobed *Escherichia coli* and Fluorostained Exopolysaccharide," J. Biomed. Mater Res., 70:274-282, (2004).
Magnusdottir, et al. "Collection of Capillary Electrophoresis Fractions on a Moving Membrane," From Methods in Molecular Biology, vol. 162: Capillary Electrophoresis of Nucleic Acids, vol. 1: Introduction to the Capillary Electrophoresis of Nucleic Acids. 22: 323-331 (2001).
Markx, G. H. et al., "Dielectrophoretic Separation of Cells: Continuous Separation," Biotechnol. Bioeng., 45:337-343, (1995).
Markx, G.H. et al., "Dielectrophoretic Characterization and Separation of Micro-Organisms" Microbiology, 140:585-591 (1994).
Meinders et al., "In Situ Enumeration of Bacterial Adhesion in a Parallel Plate Flow Chamber—Elimination or in Focus Flowing Bacteria From the Analysis," J. Microbiol. Methods, 16:119-124, (1992).
Metzger et al. C-163: Poster—"Direct Observation of Inducible Clindamycin Resistance in *Staphylococcus aureus* Using Single Live Cell Imaging," Presented at the American Society for Microbiology General Meeting May 23, 2006.
Metzger C-032: Poster—"Direct Identification of Methicillin Resistant *Staphylococcus aureus* (MRSA) Using Small Numbers of Immobilized Cells and Response to Oxacillin (OCA) by Automated Growth Analysis," Presented at the American Society for Microbiology 107th General Meeting, May 22, 2007.
Metzger et al. D-892: Poster—"Identification of mecA in *Staphylococcus aureus* Using Small Numbers of Immobilized Cells and the Response to Cefoxitin (FOX) by Automated Growth Analysis," Presented at the 47th ICAAC Sep. 28, 2007.
Metzger et al. C-005: Poster—"Direct Identification of MRSA and MLSB Phenotypes in *Staphylococcus aureus* Using Small Numbers of Immobilized Cells," Presented at the American Society for Microbiology 108th General Meeting Jun. 2, 2008.
Metzger et al. C-145: Poster—"Direct Detection and Enumeration of Viable Bacteria in Human Bronchoalveolar Lavage Specimens Using Automated Growth Rate Analysis," Presented at the American Society for Microbiology 108th General Meeting Jun. 2, 2008.
Metzger et al. D-282: Poster—"Direct Identification of the ESBL Phenotype in Enterobacteriaceae Isolates Using Small Numbers of Immobilized Cells," Presented at the 48th ICAAC and IDSA Oct. 25, 2008, Washington, DC.
Metzger et al. C-207: Poster—"Rapid Identification of Resistance Phenotypes in Gram-Negative Bacilli Using Automated Digital Microscopy," Presented at the 109th General Meeting of the ASM, Philadelphia, PA, May 23, 2009.
Metzger et al. C-1140: Poster—"Rapid Quantitation and Identification of *Pseudomonas aeruginosa, Staphylococcus aureus,* and *Acinetobacter baumannii* in Bronchoalveolar Lavage Fluid," Presented at the 110th General Meeting of the ASM May 24, 2010, San Diego, CA.
Metzger et al. Poster: "Same-Day ID and Resistance Phenotyping Directly from Respiratory Specimens by Automated Microscopy," Presented at ASM 2011, New Orleans, May 22, 2011.
Metzger et al. Poster—"Automated 4-Hour Detection of Heteroresistant Vancomycin-Intermediate *Staphylococcus aureus* (hVISA)," Presented at ASM May 22, 2011, 2011, New Orleans.
Metzger et al. D-791: Poster—"Direct-From-Remnant-Specimen Quantitative Identification Using Automated Microscopy," Presented at the 50th ICAAC, Sep. 13, 2010, Boston, MA.
Metzger and Dunne D-102: Poster—"Same-Shift ID Directly from Respiratory Specimens by Automated Microscopy," Presented at 51st ICAAC Sep. 17, 2011, Chicago, IL.
Metzger et al. C-157: Poster—"3-Hour ESBL Detection from Positive Blood Cultures Using Multiplexed Automated Digital Microscopy (MADM)," Presented at ASM 2012 Jun. 17, 2012, San Francisco, CA.
Metzger et al. C-751: Poster—"Rapid and Automated Specimen Preparation for Clinical Microbiology," Presented at ASM 2012 Jun. 17, 2012, San Francisco, CA.
Metzger D-1410: Poster—"Same-Day Blood Culture with Digital Microscopy," Presented at ICAAC 2012 Sep. 11, 2012, San Francisco, CA.
Metzger et al., "Rapid Simultaneous Identification and Quantitation of *Staphylococcus aureus* and *Pseudomonas aeruginosa* Directly from Bronchoalveolar Lavage Specimens Using Automated Microscopy," *Diagn Microbiol Infect Dis.* 79:160-165, 2014.
Miller et al., "SOS Response Induction by Beta-Lactams and Bacterial Defense Against Antibiotic Lethality," Science, 305:1629-1631, 2004.
Mishra et al., "On-Chip Micro-Biosensor for the Detection of Human CD4+ Cells Based on AC Impedance and Optical Analysis," Biosensors and Bioelectronics, 21:696-704, (2005).
Moffitt et al., "The Single-Cell Chemostat: An Agarose-Based, Microfluidic Device for High-Throughput, Single-Cell Studies of Bacteria and Bacterial Communities," Lab Chip 12:1487-1494, 2012.
Mohamad et al., "Bacteria Identification from Microscopic Morphology Using Naïve Bayes," IJCSEIT 4:1-9, 2014.
Molin et al., "Rapid Detection of Bacterial Growth in Blood Cultures by Bioluminescent Assay of Bacterial ATP," J. Clin. Microbiol. 18:521-525 (1983).
Mueller et al., "Issues in Pharmacokinetics and Pharmacodynamics of Anti-Infective Agents: Kill Curves Versus MIC," Antimicrob. Agents Chemother., 48:369-377, (2004).
Oheim, "High-Throughput Microscopy Must Re-Invent the Microscope Rather Than Speed up its Functions," Br. J. Pharmacol., 152:1-4, (2007).
Okano et al., "Using Microparticle Labeling and Counting for Attomole-Level Detection in Heterogeneous Immunoassay," Analytical Biochem., 202:120-125, (1992).
Orjih, "Heme Polymerase Activity and the Stage Specificity of Antimalarial Action of Chloroquine," J. Pharm. Exp. Ther. 282(1): 108-112 (1997).
Ozkan et al., "Electro-Optical Platform for the Manipulation of Live Cells," Langmuir, 19:1532-1538, (2003).
Plowman, "Planar Integrated Optical Methods for Examining Thin Films and Their Surface Adlayers," Biomaterials, 19:341-355, (1998).
Price et al. ePoster "Rapid Identification and Antimicrobial Susceptibility Testing of Bacteria in Bloodstream Infections Using the Accelerate ID/AST Technology," ECCMID Apr. 23, 2015, Copenhagen, Denmark.
Price et al., "Rapid Antibiotic Susceptibility Phenotypic Characterization of *Staphylococcus aureus* Using Automated Microscopy of Small Numbers of Cells," *J Microbiol Methods.* 98:50-58, 2014.
Probst et al., "Polydimethylsiloxane Sub-Micron Traps for Single-Cell Analysis of Bacteria," Micromachines, 4:357-369, (2013).
Rabinovitch et al., "Removal and Inactivation of *Staphylococcus epidermidis* Biofilms by Electrolysis," Applied and Environmental Microbiology, 72:6364-6366, (2006).
Rajagopal et al., "Eight Gram-Negative Bacteria are 10,000 Times More Sensitive to Cationic Detergents than to Anionic Detergents," *Can J Microbiol.* 49:775-779, 2003.
RMM Product Matrix, http://rapidmicromethods.com/files/matrix.php, accessed Jul. 27, 2016. (13 pages).
Rohner et al., "Advantage of Combining Resin with Lytic BACTEC Blood Culture Media," J. Clin. Micro. 35(10): 2634-2638 (1997).
Rohner et al., "Evaluation of the New Improved BHI-Lysis Blood Culture Medium for the BCB Roche System," Eur. J. Clin. Micro. Infect. Dis. 10: 620-624, 1991.

(56) References Cited

OTHER PUBLICATIONS

Rösch et al., "Chemotaxonomic Identification of Single Bacteria by Micro-Raman Spectroscopy: Application to Clean-Room-Relevant Biological Contaminations," Applied and Environmental Microbiology, 71: 1626-1637, (2005).
Rose et al., "Using the Membrane Filter in Clinical Microbiology," Med. Lab. 3: 22-23, 29, 43, 1969. Note: The numbered pages omitted from this article are advertisements.
Rowe et al., "Array Biosensor for Simultaneous Identification of Bacterial, Viral, and Protein Analytes," Analytical Chem., 71:3846-3652, (1999).
Salmon et al., "Video-Enhanced Differential Interference Contrast Light Microscopy," BioTechniques, 7:624-633, (1989).
Sapsford et al., "Detection of Campylobacter and Shigella Species in Food Samples Using an Array Biosensor," Analytical Chem., 76:433-440, (2004).
Schrot et al., "Method for Radiorespirometric Detection of Bacteria in Pure Cultures and in Blood," Appl. Micro. 26(2): 867-873 (1973).
Shamsheyeva et al. 2538: Poster—"Rapid Antimicrobial Susceptibility Testing of Non-Fermenting Gram-Negative Bacilli Directly from Positive Blood Cultures by Automated Microscopy," Presented at ASM2014, May 20, 2014, Boston, MA.
Shamsheyeva et al. 2555: Poster—"Evaluation of an Antimicrobial Susceptibility Testing Algorithm to Determine Minimum Inhibitory Concentration Using Growth of Immobilized Staphylococcal Cells Measured by Automated Microscopy," Presented at ASM2014, May 20, 2014, Boston, MA.
Shamsheyeva et al. D-873: Poster "Evaluation of an Antimicrobial Susceptibility Testing Algorithm for Gram-Positive Bacteria Directly from Positive Blood Culture Using Automated Microscopy Analysis of Susceptibility Patterns," Presented at ICAAC Sep. 7, 2014, Washington, DC.
Shamsheyeva et al. P0332: Poster—"Next Generation Automated Phenotypic Antibiotic Susceptibility Testing Utilizing Automated Microscopy Analysis of Bacterial Cells," Presented at ECCMID May 10, 2014, 2014, Barcelona, Spain.
Shamsheyeva et al. P0335: Poster—"5-Hour Antibiotic Susceptibility Testing of Enterococcus faecium and E. faecalis, and Acinetobacter baumannii Directly from Positive Blood Cultures Using Automated Microscopy," Presented at ECCMID 2014 May 10, 2014, Barcelona, Spain.
Sippy et al., "Rapid Electrochemical Detection and Identification of Catalase Positive Micro-Organisms", Biosensors & Bioelectronics, 18:741-749, (2003).
Stewart et al., "Aging and Death in an Organism that Reproduces by Morphologically Symmetric Division," PLoS Biology, 3:295-300 (2005).
Stimpson et al., "Real-Time Detection of DNA Hybridization and Melting on Oligonucleotide Arrays by Using Optical Wave Guides," Genetics, Proc. Natl. Acad. Sci. USA, 92:6379-6383, (1995).
Stuart, "The Value of Liquid for Blood Culture," J. Clin. Path. 1: 311-314 (1948).
Sun et al., "Single-Cell Microfluidic Impedance Cytometry: A Review," Microfluidics and Nanofluidics, 8: 423-443, (2010).
Suo et al., "Immunoimmobilization of Living Salmonella for Fundamental Studies and Biosensor Applications," in Salmonella —A Diversified Superbug, Chapter 25, pp. 497-522, (2012).
Taton et al., "Two-Color Labeling of Oligonucleotide Arrays via Size-Selective Scattering of Nanoparticle Probes," J. Am. Chem. Soc., 123:5164-5165, (2001).
Tison, D.L., "Culture Confirmation of Escherichia coli Serotype 0157:H7 by Direct Immunofluorescence," J. Clin. Microbio., 28, 612-613, (1990).
\ Tokuda et al., "Optical and Electric Multifunctional CMOS Image Sensors for On-Chip Biosensing Applications," Materials 4:84-102, 2011.
Tsang et al., "Characterization of Murine Monoclonal Antibodies Against Serogroup B Salmonellae and Application as Serotyping Reagents," J Clin Micro. 29:1899-1903, 1991.
Unknown, "Bacterial Counts—Quantitative Analysis of Microbes," Biology 251 General Microbiology Lab, Jul. 30, 2013, pp. 1-5, retrieved from internet: URL:http://biolabs.tmcc.edu/Micro%20Web/BacterialCounts.pdf [retrieved on Oct. 21, 2016].
Van der Borden et al., Electric Current-Induced Detachment of Staphylococcus epidermidis Biofilms from Surgical Stainless Steel, Appl. Environ. Microbiol., 70:6871-6874, (2004).
Van Soestbergen and Lee, "Pour Plates or Steak Plates?," Appl Microbiol. 18:1092-1093, 1969.
Varshney et al., "A Label-Free, Microfluidics and Interdigitated Array Microelectrode-Based Impedance Biosensor in Combination with Nanoparticles Immunoseparation for Detection of Escherichia coli O157:H7 in Food Samples," Sensors and Actuators, 128:99-107, (2007).
Vega, et al., "Effect of Ionic Strength and Porosity on Ion Diffusion in Agarose Gels," Summer Bioengineering Conference, Sonesta Beach Resort in Key Biscayne, Florida, 1-2 (2003).
Vener et al., "A Novel Approach to Nonradioactive Hybridization Assay of Nucleic Acids Using Stained Latex Particles," Analytical Biochem., 198, pp. 308-311, (1991).
Von Haebler et al., "The Action of Sodium Polyanethol Sulphonate ("Liquoid") on Blood Cultures," J. Pathol. Bacteriol. 46(2): 245-252 (1938).
Wallace et al. D-918; Poster—"Rapid Identification of Gram-negative Bacteria in Positive Blood Culture Broth Using a Multiplex Fluorescence in situ Hybridization (FISH) Assay and Automated Microscopy," Presented at ICAAC Sep. 7, 2014, Washington, DC.
Weeratna et al., "Gene Expression Profiling: From Microarrays to Medicine", J. Clin. Immunol, 24: 213-224, (2004).
Willaert, "Cell Immobilization and its Applications in Biotechnology: Current Trends and Future Prospects," in Fermentation Microbiology and Biotechnology, Chapter 12, p. 313-368, 2006.
Wit, P., and Busscher, H.J., "Application of an Artificial Neural Network in the Enumeration of Yeasts and Bacteria Adhering to Solid Substrata," J. Microbio. Methods, 32, pp. 281-290, (1998).
Wu, et al., "Microfluidic Continuous Particle / Cell Separation via Electroosmotic-Flow-Tuned Hydrodynamic Spreading," J. Micromech. Microeng., 17, pp. 1992-1999, (2007).
Yang, et al., "Electrical/ Electrochemical Impedance for Rapid Detection of Foodborne Pathogenic Bacteria," Biotechnology Advances, 26, pp. 135-150, (2008).
Yeung et al., "Bayesian Model Averaging: Development of an Improved Multi-Class, Gene Selection and Classification Tool for Microarray Data," Bioinformatics 21: 2394-2402 (2005).
Zhou, et al., "Automated Image Analysis for Quantitative Fluorescence In Situ Hybridization with Environmental Samples," App. Environ. Microbio. 73(9):2956-2962 (2007).
Zierdt et al., "Development of a Lysis-Filtration Blood Culture Technique," J. Clin. Micro. 5(1): 46-50 (1977).
Zierdt et al., "Lysis-Filtration Blood Culture Versus Conventional Blood Culture in a Bacteremic Rabbit Model," J Clin Microbiol. 15:74-77, 1982.
Zierdt, "Blood-Lysing Solution Nontoxic to Pathogenic Bacteria," J. Clin. Micro., 15(1): 172-174 (19825.
Zierdt, "Simplified Lysed-Blood Culture Technique," J. Clin. Micro. 23(3): 452-455 (1986).
CA 2,532,414 Office Action dated Jan. 27, 2014.
CA 2,532,414 Office Action dated Mar. 26, 2015.
EP 03716230.2, European Search Report dated Oct. 15, 2007.
EP 04809482.5, European Office Action dated Jul. 10, 2014.
EP 04809482.5, European Office Action dated Jun. 17, 2010.
EP 04809482.5, European Office Action dated Mar. 13, 2008.
EP 04809482.5, Supplementary European Search Report dated Oct. 19, 2007.
EP 05854636.7, European Office Action dated Mar. 3, 2014.
EP 05854636.7, European Search Report dated Feb. 13, 2013.
EP 12754797.4, Intention to Grant dated May 21, 2015.
EP 12754797.4, Supplementary European Search Report dated Sep. 24, 2014.
EP 13835702.5, European Partial Supplementary Search Report dated Feb. 25, 2016 (8 pages).

(56) References Cited

OTHER PUBLICATIONS

EP 13835702.5, European Supplementary Search Report dated Jun. 24, 2016 (12 pages).
EP 13835702.5, Rules 70(2) and 70a(2) EPC Communication dated Jul. 12, 2016 (1 page).
EP 14762411.8 Extended European Search Report dated Nov. 7, 2016 (11 pages).
EP 14762411.8 Partial Supplementary European Search Report dated Jul. 29, 2016 (10 pages).
EP 98911454, European Search Report dated Aug. 5, 2004.
\ EP16200084.8 Partial European Search Report dated Mar. 1, 2017.
PCT/US1998/04086, International Preliminary Examination Report dated Jun. 11, 1999.
PCT/US1998/04086, International Search Report dated Jul. 14, 1998.
PCT/US1999/010917, International Search Report dated Jul. 30, 2001.
PCT/US2003/006086, International Search Report dated Jun. 27, 2003.
PCT/US2004/022025, International Preliminary Report on Patentability dated Sep. 26, 2006.
PCT/US2004/022025, International Search Report dated Aug. 7, 2006.
PCT/US2004/022025, Written Opinion dated Aug. 7, 2006.
PCT/US2005/045961, International Preliminary Report on Patentability dated Oct. 30, 2007.
PCT/US2005/045961, International Search Report dated Oct. 15, 2007.
PCT/US2005/045961, Written Opinion dated Oct. 15, 2007.
PCT/US2009/038988, International Preliminary Report on Patentability dated Oct. 5, 2010.
PCT/US2009/038988, International Search Report and Written Opinion dated Jun. 8, 2009.
PCT/US2012/028139, International Preliminary Report on Patentability dated Sep. 19, 2013.
PCT/US2012/028139, International Search Report dated Sep. 28, 2012.
PCT/US2012/028139, Search Report and Written Opinion dated Sep. 28, 2012.
PCT/US2013/059104, International Preliminary Report on Patentability dated Mar. 10, 2015.
PCT/US2013/059104, International Search Report and Written Opinion dated Jan. 10, 2014.
PCT/US2014/030745, International Search Report and Written Opinion dated Aug. 27, 2014.
PCT/US2015/032290; International Search Report and Written Opinion dated Aug. 24, 2015 (13 pages).
PCT/US2016/025075 Invitation to Pay Additional Fees with Partial International Search dated Jul. 6, 2016.
PCT/US2016/025075, International Search Report and Written Opinion dated Nov. 15, 2016 (36 pages).
EP 16192372.7 Extended European Search Report and Written Opinion dated Feb. 28, 2018 (11 pages).
Inoue er al., "On-chip culture system for observation of isolated individual cells," *Lab on a Chip* 1:50-55, 2001.
Rodrigues and Kroll, "Rapid selective enumeration of bacteria in foods using a microcolony epifluorescence microscopy technique," *J Appl Bacterial.* 64:65-78, 1988.
Zhu et al., "Filter-based microfluidic device as a platform for immunofluorescent assay of microbial cells," *Lab Chip* 4:337-341, 2004.
Palarasah et al., "Sodium Polyanethole Sulfonate as an Inhibitor of Activation of Complement Function in Blood Culture Systems," *J Clin Microbiol.* 48:908-914, 2010.
EP 13835702.5 Office Action dated Oct. 16, 2017 (9 pages).

* cited by examiner

RAPID DETERMINATION OF MICROBIAL GROWTH AND ANTIMICROBIAL SUSCEPTIBILITY

CROSS REFERENCE TO RELATED APPLICATIONS

This application is a divisional of U.S. application Ser. No. 14/209,917 filed on Mar. 13, 2014, which claims priority to U.S. Provisional Application No. 61/798,105 filed on Mar. 15, 2013, the entire contents of which are herein incorporated by reference.

SUMMARY

In various embodiments, the systems, methods and computer readable mediums described may be capable of evaluating microorganisms. For example, a method may comprise: determining, by a computer-based system configured to analyze microorganism information and comprising a processor, a tangible, non-transitory memory, and an interface, a first value associated with an attribute of a microorganism, based on first information from a microorganism detection device; determining, by the computer-based system, a second value associated with the attribute of the microorganism, based on second information from the microorganism detection device; determining, by the computer-based system, a growth rate associated with the first value and the second value; and comparing, by the computer-based system, the growth rate to a control growth rate.

In various embodiments, the systems, methods and computer readable mediums described may be capable of determining a growth rate of one or more microorganisms. The method may comprise: determining, by a computer-based system configured to analyze microorganism information and comprising a processor, a tangible, non-transitory memory, and an interface, a first value corresponding to a growth rate of a microorganism, based on information from a microorganism detection device, in response to subjecting a microorganism to at least one of a first event and a first condition; obtaining, by the computer-based system, a second value corresponding to a growth rate of a reference microorganism; and determining, by the computer-based system, a proportional relationship between the first value to second value.

In various embodiments, the second value may be determined in response to an event.

In various embodiments, the microorganism may be an individuated microorganism.

In various embodiments, the microorganism may be subjected to a condition.

In various embodiments, the condition may be associated with the event.

In various embodiments, the control growth rate may be at least one of a predetermined growth rate and a dynamically determined growth rate.

In various embodiments, the event may be at least one of a predetermined time, a dynamically determined mass, a number of individuated microorganisms, and a number of clones.

In various embodiments, the condition may be at least one of a temperature, a growth medium condition, a carbon source, a nitrogen source, an amino acid, a nutrient, a salt, a metal ion, a cofactor, a pH, a trace element, a dissolved gas, an antimicrobial agent, an aerobic condition, and an anaerobic condition.

In various embodiments, the condition may be at least one of static and dynamic.

In various embodiments, the microorganism information may be a plurality of attributes evaluated simultaneously.

In various embodiments, the methods may further comprise determining, by the computer-based system, a clone signal intensity curve shape likelihood or other variant response function.

In various embodiments, the methods may further comprise determining, by the computer-based system, a tracking error likelihood.

In various embodiments, the methods may further comprise calculating, by the computer-based system, a growth likelihood value based on the clone signal intensity curve shape likelihood and tracking error likelihood.

In various embodiments, the methods may further comprise determining, by the computer-based system, microorganism susceptibility based on the comparison of the growth likelihood value to a range.

In various embodiments, the methods may further comprise rendering, by the computer-based system, a signal associated with the microorganism into a plurality of signal approximations.

In various embodiments, the plurality of signal approximations are planes comprising a plurality of point amplitudes corresponding to microorganism locations.

In various embodiments, the methods may further comprise combining, by the computer-based system, the signal approximations to create a microorganism model.

In various embodiments, the methods may further comprise analyzing, by the computer-based system, the point amplitudes associated with at least one of background information and noise information.

In various embodiments, the methods may further comprise filtering by the computer-based system, the signal approximations to eliminate at least one of background information and noise information.

In various embodiments, the methods may further comprise registering, by the computer-based system, locations associated with point amplitudes corresponding to microorganisms.

In various embodiments, the second value may be obtained from a reference growth curve associated with the reference microorganism.

In various embodiments, the event may be at least one of a predetermined time, a dynamically determined mass, a number of individuated microorganisms, and a number of clones.

In various embodiments, the condition may be at least one of a temperature, a growth medium condition, a carbon source, a nitrogen source, an amino acid, a nutrient, a salt, a metal ion, a cofactor, a pH, a trace element, a dissolved gas, an antimicrobial agent, an aerobic condition, and an anaerobic condition.

In various embodiments, the methods may further comprise evaluating by the computer-based system, the proportional relationship against a range.

In various embodiments, the methods may further comprise identifying, by the computer-based system, microorganism susceptibility to an antimicrobial agent in response to the proportional relationship being within the range.

In various embodiments, the methods may further comprise identifying, by the computer-based system, that the microorganism may be not susceptible to an antimicrobial agent in response to the proportional relationship being outside the range.

In various embodiments, the methods may further comprise identifying, by the computer-based system, that the microorganism may be resistant to an antimicrobial agent in response to the proportional relationship being outside the range.

In various embodiments, the methods may further comprise identifying, by the computer-based system, that the microorganism may be expressing a virulence factor in response to the proportional relationship being outside the range.

In various embodiments, the methods may further comprise identifying, by the computer-based system, that the microorganism may be hypervirulent in response to the proportional relationship being outside the range.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION OF THE ILLUSTRATED EMBODIMENTS

Figure 1:
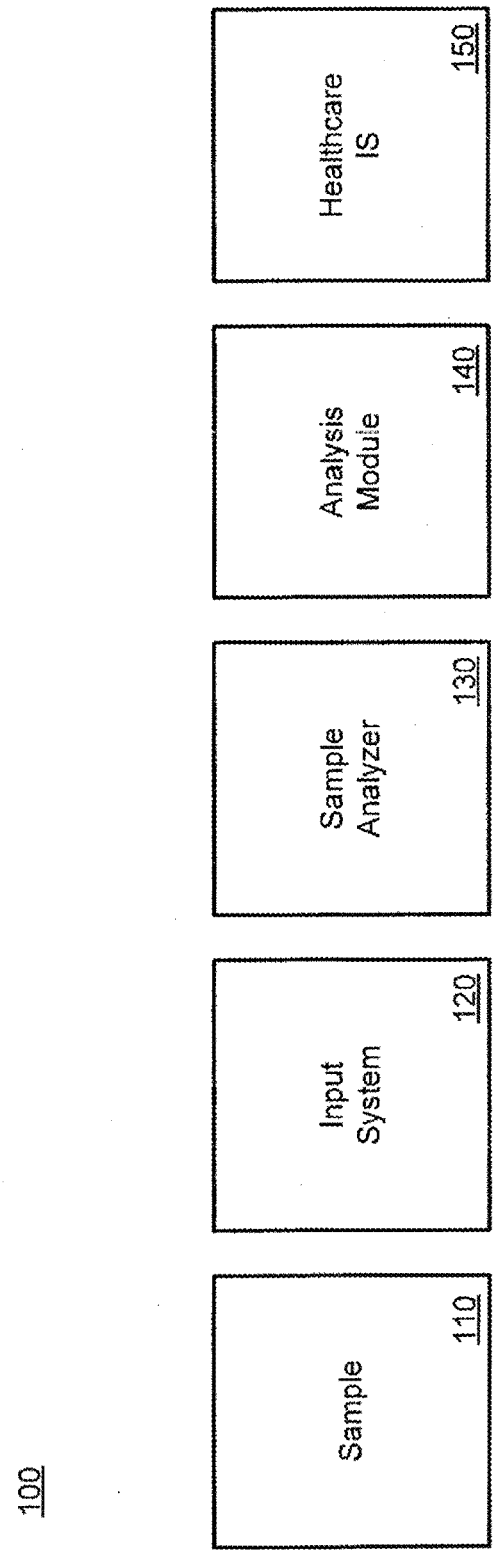
FIG. 1 illustrates a block diagram of an exemplary system capable of evaluating one or more microorganisms.

The detailed description of various embodiments herein makes reference to the accompanying drawing figures, which show various embodiments and implementations thereof by way of illustration and best mode, and not of limitation. While these embodiments are described in sufficient detail to enable those skilled in the art to practice the embodiments, it should be understood that other embodiments may be realized and that mechanical and other changes may be made without departing from the spirit and scope of the present disclosure. Furthermore, any reference to singular includes plural embodiments, and any reference to more than one component may include a singular embodiment. Likewise, any ordination of a device or of a component or portion of a device with designations such as "first" and "second" is for purposes of convenience and clarity and should not be construed as limiting or signifying more than an arbitrary distinction. Moreover, recitation of multiple embodiments having stated features is not intended to exclude other embodiments having additional features or other embodiments incorporating different combinations of the stated features.

Systems, methods and computer program products are provided in various embodiments of the present disclosure. References to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Various aspects of the present disclosure can be realized by any number of devices and methods configured to perform the intended functions. Stated differently, other devices and methods can be incorporated herein to perform the intended functions. It should also be noted that the accompanying drawing figures referred to herein are not drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

In various embodiments, the systems, methods and computer readable medium (collectively "systems") described herein are capable of determining microorganism information (e.g., data describing a microorganism attribute). More specifically, the systems described herein are capable of identifying and quantifying individuated microorganism characteristics (e.g., growth). The microorganism information may be used to recommend treatment options for a microorganism based on an event or the identity of the microorganism.

In various embodiments, the systems can identify individuated microorganisms and evaluate microorganism growth under or in response to various conditions. For example, the microorganism may be exposed to a first condition that stimulates growth (e.g., an increase in temperature) and/or a second condition that inhibits growth (e.g., an antimicrobial agent). As such, the system can be capable of determining microorganism identification, growth, antimicrobial susceptibility and/or resistance, and/ or providing a variety of analytical outputs based on a multi-variable or multi-factorial analysis.

In various embodiments, the systems described herein may be implemented as hardware, hardware-software, or software elements. These systems may comprise one or more modules, analyzers, hardware components, software components, and/or the like.

Definitions

Definition of Microorganism

As used herein, the terms "microorganism" and "organism" mean a member of one of following classes: bacteria, fungi, algae, and protozoa, and can also include, for purposes of the present disclosure, viruses, prions, or other pathogens. In various embodiments, bacteria, and in particular, human and animal pathogens, are evaluated. Suitable microorganisms include any of those well established in the medical art and those novel pathogens and variants that emerge from time to time. Examples of currently known bacterial pathogens, for example, include, but are not limited to genera such as *Bacillus, Vibrio, Escherichia, Shigella, Salmonella, Mycobacterium, Clostridium, Cornyebacterium, Streptococcus, Staphylococcus, Haemophilus, Neissena, Yersinia, Pseudomonas, Chlamydia, Bordetella, Treponema, Stenotrophomonas, Acinetobacter, Enterobacter, Klebsiella, Proteus, Serratia, Citrobacter, Enterococcus, Legionella, Mycoplasma, Chlamydophila, Moraxella, Morganella*, and other human pathogens encountered in medical practice. Similarly, microorganisms may comprise fungi selected from a set of genera such as *Candida, Aspergillus*, and other human pathogens encountered in medical practice. Still other microorganisms may comprise pathogenic viruses (sometimes human pathogens) encountered in medical practice, including, but not limited to, orthomyxoviruses, (e.g., influenza virus), paramyxoviruses (e.g., respiratory syncytial virus, mumps virus, measles virus), adenoviruses, rhinoviruses, coronaviruses, reoviruses, togaviruses (e.g., rubella virus), parvoviruses, poxviruses (e.g., variola virus, vaccinia virus), enteroviruses (e.g., poliovirus, coxsackievirus), hepatitis viruses (including A, B and C), herpes viruses (e.g., Herpes simplex virus, varicella-zoster virus, cytomegalovirus, Epstein-Barr virus), rotaviruses, Norwalk viruses, hantavirus, arenavirus, rhabdovirus (e.g., rabies virus), retroviruses (including HIV, HTLVI, and II), papovaviruses (e.g., papillomavirus), polyomaviruses, picornaviruses, and the like. With respect to viruses, in general, the methods and compositions of the disclosure may be used to identify host cells harboring viruses.

As used herein, the term "microorganism" can be used to refer to a single cell, such as a single or individual bacterial cell. The term "microorganism" may also be used to refer to a clone comprising more than one cell, such as a group of cells or organisms produced asexually from a single progenitor cell or ancestor. In various embodiments and as used herein, the term "microorganism" may also refer to a group of cells that may be genetically distinct (i.e., arising from more than one progenitor cell or ancestor) but may be physically associated and evaluated as a single "microorganism."

Definition of Samples

The present disclosure provides systems of detecting microorganisms within samples (e.g., sample 110 discussed herein). Samples, including, for example, samples in solution, may comprise any number of sources, including, but not limited to, bodily fluids (including, but not limited to, blood, urine, serum, lymph, saliva, anal and vaginal secretions, perspiration, peritoneal fluid, pleural fluid, effusions, ascites, purulent secretions, lavage fluids, drained fluids, brush cytology specimens, biopsy tissue, explanted medical devices, infected catheters, pus, biofilms, and semen) of virtually any organism, with mammalian samples, particularly human samples, and environmental samples (including, but not limited to, air, agricultural, water, and soil samples) finding use in the system of the present disclosure. In addition, samples can be taken from food processing, which can include both input samples (e.g., grains, milk, or animal carcasses), samples in intermediate steps of processing, as well as finished food ready for the consumer. The value of system of the present disclosure for veterinary applications should be appreciated as well, for example, with respect to its use for the analysis of milk in the diagnosis and treatment of mastitis, or the analysis of respiratory samples for the diagnosis of bovine respiratory disease.

Samples can range from less than a milliliter up to a liter for certain respiratory lavage fluids, and can further range in bacterial concentration from less than one bacterium to greater than $10^9$ bacteria per milliliter. Furthermore, the sample can be present in blood, urine, sputum, lavage fluid or other medium. Sample concentration may be used to concentrate the sample so that bacteria that are present in small numbers can be effectively introduced into the system, as well as so the background liquid medium can be normalized, or in some cases eliminated or reduced, to provide consistent sample properties upon introduction to a system. It should be noted, however, that various samples may be used without concentration or other modification within the scope of the present disclosure.

Definition of Growth

As used herein, the term "growth" may include any measurable change attributable to or occurring within the life history of an organism, whether that change occurs under static external conditions or in response to a change in an internal or external event or condition. The term "growth" can be used to describe any change, regardless of whether the change is positive or negative. "Growth" can also be used to describe a lack of growth, or neutral growth, where there may be no measurable change, or no net change, in a measured value of an attribute of a microorganism. "Growth" can be used to refer to one or more changes associated with a single microorganism, or growth can be used to refer to a net or collective change in a group, collection, or population of organisms, whether derived from a single parental cell or from multiple parental cells. "Positive growth" in the case of microorganisms that are cells (e.g., bacteria, protozoa, and fungi) can refer to an increase in an attribute of a microorganism, including such attributes as, mass, cell divisions (e.g., binary fission events or cell doubling resulting in the production of daughter cells), cell number, cell metabolism products, or any other experimentally observable attribute of a microorganism.

In accordance with various embodiments, microorganism size, (whether in one, two, or three dimensions), need not be used to evaluate growth with respect to microorganisms that are individual cells or individuated, multicellular clones; in such circumstances, size may not be a useful or informative metric of growth, and in fact may be misleading. However, in various embodiments and in accordance with a definition of "microorganism" wherein a microorganism may comprises a group or population of cells originating from a plurality of unrelated progenitor cells, the size of the microorganism may be evaluated as an attribute that may be measured with respect to a determination of growth, insofar as the size of the microorganism may serve to represent the mass or number of the cells of which the microorganism is comprised.

In the case of viruses, "positive growth" can refer to the reproduction of viruses, generally within a host cell, and can include host cell lysis, in the case of lytic viruses. Thus, "positive growth" of a virus may sometimes be detected as a loss of the discrete host cell.

Various methods of detection of an attribute of a microorganism are described in greater detail below (see, for example, U.S. Pat. Nos. 7,687,239 and 7,341,841, the entire contents of which are incorporated by reference herein). By way of example and with reference to various optically-based methods that may be used to detect growth, detecting positive growth of a microorganism can include detecting either an increase in the mass of the microorganism and/or detecting the occurrence of one or more cell divisions as evidenced by the production of daughter cells. In various embodiments and as described in greater detail herein, detection of a change in the mass of a microorganism may be performed using any of a variety of methods that may directly or indirectly measure a change in the quantity of mass of a microorganism.

As used herein, the term "mass" may be used in various senses with respect to the measurement or detection of microorganism growth. For example, the term "mass" may be used in a formal sense to describe a quantity of matter, such as the mass of a microorganism or the change in the mass of a microorganism as might be determined using a microbalance. In general, however, as used herein, the term "mass" may also be used to describe a measure that may be indirectly or directly related to, or serve as a proxy for, a measurement of a quantity of matter. For example, a measurement of an increase in the size or number of microorganisms may be described as an increase in the "mass" of the microorganism(s) (i.e., the "biomass" of the microorganisms, such as may be determined by various measurement techniques that assess, directly or indirectly, changes in an apparent "mass" of a microorganism, clone, or population, where the measured change may or may not correlate exactly with a change in the "mass" as an actual quantity of matter). Any method that may be used to evaluate the "mass" of a microorganism, whether by a direct determination of a quantity of matter, or by a measure of a quantity that may be directly or indirectly related to the quantity of matter of a microorganism, can be used to detect growth for purposes of the systems and methods of the present disclosure.

As mentioned herein, "detecting growth" can also refer to detecting a lack of positive growth and/or to detecting negative growth. For example, a microorganism life cycle can include one or more phases wherein "growth" may not be ascertainable using certain measurement techniques, such as during periods traditionally referred to as a "lag phase" or "death phase." Likewise, some antimicrobial agents act by retarding positive growth, while failing to produce cell mortality. In such cases, detecting little or no change in the size or mass of a microorganism, for example, may be included within the evaluation of "growth." Explained differently, in the absence of an antimicrobial agent, a microorganism may exhibit positive growth, but in the presence of the agent, a lack of growth may be significant, even if the microorganism does not die. Thus, in some cases, such as the forgoing example, small (or decreased) changes may be measured in a period of time relative to the mass, increase in number, or any other attribute of microorganism that may be observed; however, these changes may be meaningfully distinguishable from positive growth.

In addition, processes such as bacterial programmed cell death (e.g., apoptosis and/or autophagic cell death) may be considered negative growth. In general, detection of negative growth relies on changes, usually but not always decreases, in microorganism mass, number, or any other attribute that can be measured. In various embodiments, detection of cell death may further include the use of an indicator of a condition associated with cell death or a lack of cell viability, such as a mortal stain or a change in intrinsic fluorescence.

As used herein, "detecting growth" can also refer to detecting changes in an attribute of a microorganism that may be in a growth phase other than that associated with logarithmic or exponential phase growth. In other words, "detecting growth" can comprise detection of changes in an attribute of a microorganism in a phase of growth that might traditionally be referred to as lag phase, stationary phase, or death phase, for example. Changes associated with such phases may be neutral or negative with respect to changes in the size, "mass," or "biomass." As described above, the lack of measurable changes in number, "mass," or "biomass" may be significant and serves as a measure of "growth." However, in various embodiments, other attributes that may nonetheless be measured and exhibit measurable changes may also be used to derive a measure of growth, as used herein. Thus, detection of growth can relate to measurement of attributes associated with, for example, homeostasis, catabolism, cell death, or necrosis. These attributes can include, for example, measurement of metabolite production, protein production, cell membrane integrity, ion channel activity, gene transcription, and the like. Various attributes of a microorganism that may be measured with respect to a determination of a growth rate, along with various methods that may be used to detect and measure those attributes, are described in greater detail below.

Thus, "detecting growth" can refer to detecting positive growth, detecting a lack of growth, e.g., detecting cells that are not actively dividing but are not growing positively, and detecting negative growth, for example, cell death.

In various embodiments, detecting growth may be performed at the individual or discrete microorganism level, rather than at a gross colony or population level. Thus, "detecting growth of a discrete microorganism" may be performed as an evaluation of growth of an individual cell or clone, for example, in a period of time such that a small population of daughter cells can be formed, but prior to the ability to visually see a colony with the naked eye. This aspect of various embodiments has been described as "quantum microbiology," wherein individuated microorganisms (i.e., discretely and/or repeatably identifiable microorganisms, whether individual cells or clones comprising more than one cell, or microorganisms comprising more than clone in close physical approximate and treated as an individual microorganism, as defined above) can be analyzed as described herein. In various embodiments, the ability to analyze or measure changes in the attributes of individuated microorganisms may, for example, enable growth to be detected in a very short time frame in comparison to traditional microbiological methods. For example, growth may be detected within an absolute time frame of only a few cell doubling events of a microorganism, rather than the tens or hundreds of doubling events that may be required to assess growth and/or susceptibility with traditional methods. Furthermore, certain embodiments of the present disclosure do not require an initial growth of microorganisms (either liquid or solid) prior to an evaluation of growth; rather, some methods are sufficiently sensitive to enable starting with direct-from-specimen biological samples with no growth or culturing prior to the assay. In general, the methods of the disclosure can be performed within and rely on measures of growth that may be made within an absolute timeframe within which a microorganism present in the sample may undergo from 1 to about 10 doubling events, with from about 1 to about 4 being particularly useful, and 1 to 2 being ideal in situations where the "time to answer" is being minimized.

In various embodiments, "detecting growth" may be performed using a computer-based system, as described in greater detail below. In various embodiments, a computer-based system can comprise a processor, a tangible, non-transitory memory, and an interface. The computer-based system may be configured to perform method steps and/or execute instructions on a computer readable medium. In these embodiments, a determination of a growth rate may be made by integrating information associated with the detection and/or measurement of one or more attributes of a microorganism over a period of time. In various embodiments, a determination of a growth rate, or a lack thereof, for a microorganism may be based not solely on a direct or absolute assessment of cell viability, change in size or mass, performance of metabolic processes (i.e., homeostasis, anabolic, or catabolic processes), reproduction, or the like, but instead may be based on a probabilistic assessment that a measured change in one or more attributes is likely to correspond to growth. Thus, in various embodiments, a growth rate may be determined based on measurement of a change in one or more attributes over time and a determination of a statistical probability of whether the measured change corresponds to growth, as compared to a control or reference.

As explained in more detail herein, the determination of a statistical probability of whether a measured change corresponds to growth may comprise a product of a plurality of factors or likelihoods derived from an assessment of various factors. In various embodiments, a control against which an identification of growth (i.e., the statistical probability that a process interpreted as growth is occurring) is made may be an internal control, such as a control run contemporaneously with the sample for which a determination of growth is being made. In other embodiments, a control may be a predetermined standard. For example, a sample for which a growth rate is to be determined may be measured in an under a set of standardized conditions for which one or more reference growth rates (for example, a library of reference or standard growth curves) are available, and a determination of a growth rate may be made for the sample based on comparison of the experimentally determined growth rate against one or more reference growth rates. In various embodiments, such reference growth rates may be empirically determined by a user at a time that is separate from the experimental determined growth rate for a sample. In other embodiments, reference growth rates under standard conditions for a growth determination system may be determined by a third party, and the reference growth rates may be obtained from the third party by a user for experimental determination of a growth rate of a sample.

In various embodiments, a determination of a growth rate, or a determination that a probability that a measured change of an attribute of a microorganism in a sample comprises growth in a statistically or clinically meaningful sense, may be made for a sample based not only on comparison of a sample growth rate against one or more reference growth rates, but may also comprise consideration of additional factors that may modify the calculation of the probability of growth based on comparison of the measured attribute to a reference growth rate. For example, measurements of an increase in cell volume may be used to determine a growth rate, but those same measurements of cell volume may also be fit to models or references relative to models of cell shape that may or may not be integrated into the reference growth rates used for comparison. In this manner, conformity (or lack thereof) of attributes of cell size and/or shape changes relative to various expected models of cell morphology may modify the probability that the measured microorganism attribute change corresponds to a reference growth rate. Similarly, other factors, such as the number of cell divisions and the probability that the observed cell or group of cells in a measurement made at a first time corresponds to the observed cell or group of cells in measurement made at a second or subsequent times may also modify to determination of the probability that a sample or microorganism therein is demonstrating growth.

In various embodiments, a determination of a growth rate of a microorganism in response to a condition may provide clinically meaningful or useful information, for example, where the microorganism originates from a patient sample and the condition comprises an antimicrobial agent. The growth rate determined for a microorganism, compared against a reference growth rate, in accordance with various embodiments of the present disclosure, may facilitate identifying whether the microorganism is susceptible to the antimicrobial agent and/or whether the microorganism is resistant to the antimicrobial agent. For example, susceptibility of a microorganism to an antimicrobial agent may be identified by determining a rate of growth in response to a condition comprising a concentration of the antimicrobial agent and comparing the growth rate of the microorganism to a reference growth rate. If a proportional relationship of the growth rates is determined to be outside of a range or below a threshold criterion, for example, the microorganism may be identified as susceptible to the antimicrobial agent.

As used herein, "susceptibility" means that an antimicrobial agent will have an inhibitory effect on the growth of a microorganism or a lethal effect on the microorganism. "Susceptibility" further includes the concept of a minimum inhibitory concentration ("MIC") of an antimicrobial agent, defined as a concentration of an antimicrobial agent that will arrest growth of a microorganism. Identification of "susceptibility," for example, using the system and method described herein, may provide information that may be useful to a clinician in making a decision regarding antimicrobial agent therapy for a patient.

In various embodiments, for example, if a proportional relationship of growth rates is determined to be outside of a range or above a threshold criterion, a microorganism may be identified as resistant.

As used herein "resistant" is means that a microorganism is not substantially affected by an antimicrobial agent. For example, resistance may be identified by determining that a microorganism's growth is not substantially affected by a MIC of an antimicrobial agent. It is important to note that identification of resistance provides no information as to susceptibility or identification of clinically therapeutic treatment options, with the exception that the antimicrobial agent to which a microorganism is identified as resistant may be ruled out as a viable clinical therapeutic agent, assuming that the resistant microorganism is a pathogenic microorganism responsible for an infection in a patient. In various embodiments, "resistance" may be related to known mechanisms associated with a particular microorganism genotype, wherein the mechanism providing antimicrobial agent resistance to the microorganism is genetically encoded and expressed to confer a resistant phenotype.

In various embodiments, determination of a growth rate may also facilitate identifying whether a microorganism demonstrates intermediate susceptibility to an antimicrobial agent. Traditional clinical AST testing procedures often report information related to the identity of a pathogen in a sample and a table of antimicrobial agents to which a pathogen or other microorganism is susceptible, intermediate, or resistant ("SIR"). In accordance with various embodiments, the system and methods disclosed herein may be used to rapidly provide similar information, including empirically determined resistance and susceptibility data based on subjecting a microorganism to a condition comprising an antimicrobial agent, rather than data that may simply rely on performing microorganism identification alone.

In various embodiments, determination of the growth rate of a microorganism may further be used to identify that the microorganism is, for example, expressing a virulence factor or hypervirulent. For example, a microorganism may demonstrate an altered growth rate due to expression of one or more virulence factors that may be associated with enhanced pathogenicity. In various embodiments, a growth rate of a microorganism expressing a virulence factor (or a hypervirulent microorganism) may exhibit a growth rate that is higher than a reference organism, or a growth rate that is lower than a reference organism.

Definition of an Attribute of a Microorganism

As used herein, an "attribute of a microorganism" can be any detectable or measurable feature or characteristic of a microorganism. An attribute can be directly associated with a microorganism, for example, a feature or characteristic that is physically located on or within or otherwise directly physically associated with a microorganism. Such a directly associated attribute can include, for example, the size, shape, mass, intrinsic fluorescence, cell surface features, membrane integrity, genomic DNA, ribosomal RNA subunits, etc. A directly associated attribute can also include, for example, both directly and indirectly bound markers such as may be used in indirect immunofluorescence microscopy. As used herein, an attribute can also include a feature that is indirectly associated with a microorganism, such as proteins or metabolites that are secreted into a medium or colorimetric indicators used as substrates in enzyme-linked immunosorbent assays, for example. Furthermore, an attribute can be a feature or characteristic of a microorganism, regardless of whether the microorganism is viable or dead, intact or disrupted. Any value related to the presence of a microorganism that may be observed, detected, or measured, using any technique, whether presently available or yet to be developed, is within the scope of an attribute of a microorganism as used in the present disclosure.

Growth Conditions

Figure 4A:
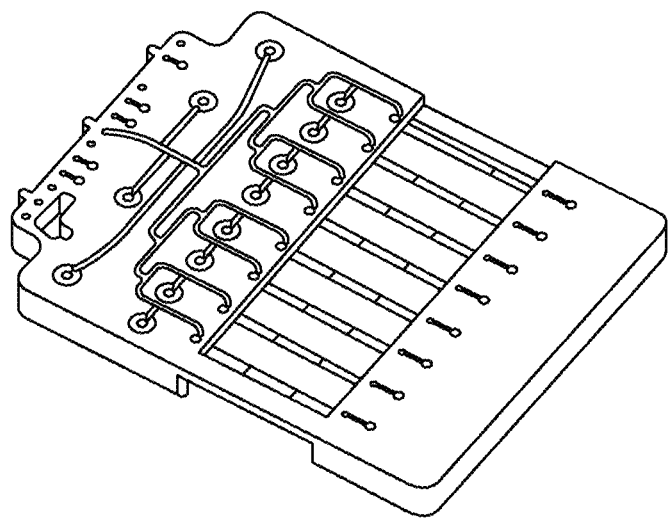
FIGS. 4A-4B illustrate an exemplary (A) cassette and (B) flowcell channel, respectively, of a microorganism evaluation device.
Figure 4B:
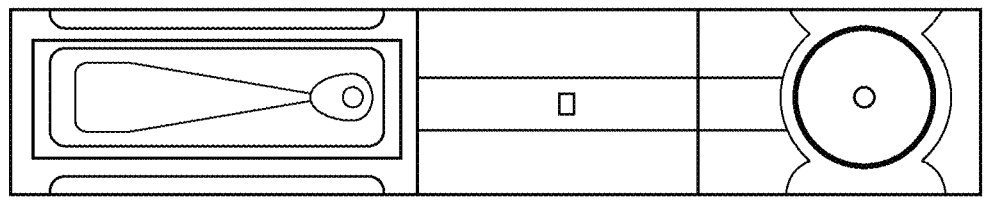

In various embodiments, microorganisms to be analyzed may be maintained in or subjected to one or more conditions suitable for growth. For example, the sample handling and detection systems described herein may include one or more sample vessels in which microorganism samples are placed for detection and analysis. In various embodiments and as illustrated in FIGS. 4A and 4B, a sample vessel may comprise a disposable microfluidic flowcell cassette having a plurality of separate cells (flowcells) or chambers into which microorganisms may be placed. The cassette and the flowcells may be configured, for example, as described in U.S. Pat. No. 7,341,841 (the entire contents of which are incorporated by reference herein), in a manner whereby it may be possible to regulate the media composition (including antibiotic presence and concentration), flow rate, temperature, pH, gas mixture, pressure, and any other environmental parameter that may be regulated in relation to microorganism growth. Likewise, the remainder of the system outside of the cassette may also be configured to provide for regulation and/or manipulation of any of a variety of environmental or external parameters.

In various embodiments and as used herein, a "condition" can be any parameter related to or having an influence on microorganism growth. For example, a "condition" can include parameters required for or beneficial to microorganism growth, and a "condition" can include parameters that may inhibit microorganism growth. Likewise, a "condition" can refer to a single parameter or variable that may influence microorganism growth, or a "condition" may collectively refer to a set of parameters or variables. A "condition" can include any traditional microbiological culture medium that may be known to a person of ordinary skill in the art, and a "condition" can further include any growth (or selective) medium comprising any combination of medium components, whether defined or undefined (complex). Examples of medium components and classes of components include carbon sources, nitrogen sources, amino acids, extracts, salts, metal ions, cofactors, vitamins, dissolved gasses, and the like. Similarly, a "condition" can include various components that might be added to a medium to influence the growth of a microorganism, such as selective and non-selective antimicrobial agents that may inhibit or arrest microorganism growth, modulating agents (i.e., agents that may alter microorganism growth but are not considered antimicrobial agents), or enrichment agents (e.g., substances that may be required for auxotrophic microorganisms, such as hemin, or substances that may be required by fastidious organisms) or other components that may encourage microorganism growth. A "condition" can also include other environmental parameters separate from the composition of a culture medium, such as light, pressure, temperature, and the like. Similarly, a condition can include any of a variety of other parameters that might occur or be imposed, such as: a host organism defensive material or cell (e.g., human, defensin proteins, complement, antibody, macrophage cell, etc.), a surface adherent material (i.e., surfaces intended to inhibit growth, kill cells, etc.), a physiological, metabolic, or gene expression modulating agent (e.g., host defense activation with co-cultured host cells), a physiological salt, metabolite, or metabolic waste materials (such as may be produced by living microorganisms or used to simulate late-stage culture growth conditions (i.e., stationary phase conditions)), a reduction in nutrient media (simulating, for example, stationary phase conditions), or a bacteriophage infection (actual or simulated). Furthermore, a "condition" may be static (e.g. a fixed concentration or temperature) or dynamic (e.g. time-varying antimicrobial concentration to simulate pharmacokinetic behavior of intermittent infusions; or to simulate any endogenous or exogenous process affecting microbe response). These definitions of "condition" are intended to be illustrative, rather than exhaustive, and, as used herein, a "condition" can include any endogenous or exogenous parameter that may influence a microorganism.

In various embodiments, a system may include a temperature regulated incubation chamber in which the sample cassette may be maintained during microorganism detection and analysis. In various embodiments, a system may include ability to provide for temperature regulation of the cassette or sample chambers such as by using Peltier elements, resistive heating elements, or temperature regulation of circulating liquid medium for growth during or between evaluations. Temperature regulation may comprise maintaining a microorganism at a fixed temperature during an analysis period, or may comprise providing changing temperatures according to a predetermined temperature profile. A temperature regimen comprising changing temperature can include temperature changes at predetermined temperature change slopes or ramps. In various embodiments, temperature regulation may comprise simultaneously providing different temperatures or temperature profiles for individual chambers or flowcells in a cassette during an analysis period.

In some variations the system may be further configured to accelerate microorganism (and particularly bacterial) growth relative to standard clinical microbiological culturing conditions. Microorganism growth may be accelerated while evaluating growth by changing, for example, the temperature, composition, and/or oxygen content of the media. For example, increasing the temperature may provide an increased rate of microorganism growth and enable a determination of a rate of growth using the system and method disclosed herein in a shortened time frame relative to incubation at a temperature used in standard AST methods.

Microorganism Detection

Once the microorganisms present in the sample have been individuated in the biosensor, individual microorganisms can be interrogated (e.g., optically or spectroscopically) to characterize and/or identify the microorganisms in the sample. The interrogation or detection of an attribute of a microorganism can take place in a non-invasive manner that does not interfere with the integrity or viability of the microorganism, that is, attributes of a microorganism present in a sample can be detected and measured while the microorganism remains in the sample cassette. The ability to identify the microorganisms in a non-invasive manner, optionally coupled with keeping the sample contained (e.g., sealed within a sample cassette or equivalent device) throughout the analysis process, along with automation of the procedure, may contribute to reduced handling of potentially pathogenic samples and may increase the safety of an identification or AST process relative to traditional clinical microbiological methods. Furthermore, the ability to characterize and/or identify microorganisms, for example, by direct interrogation of a direct-from-specimen sample without further processing of the sample (e.g., resuspension, plating, and growth of colonies) can greatly increase the rapidity with which identification/characterization can be made.

Any of a number of methods that may provide an ability to detect an attribute of a microorganism may be used in various embodiments. Examples of methods that may provide real-time or near real-time detection can include brightfield imaging, darkfield imaging, phase contrast imaging, fluorescence imaging, upconverting phosphor imaging, chemiluminescence imaging, evanescent imaging, near infra-red detection, confocal microscopy in conjunction with scattering, surface plasmon resonance ("SPR"), atomic force microscopy, and the like. Likewise, various combinations of detection methods may be used in parallel or in complementary fashion to detect one or more attributes of a microorganism in accordance with the present disclosure.

In various embodiments, spectroscopic methods can be used to detect one or more attributes of the microorganisms. These may include intrinsic properties, such as a property present within the microorganism in the absence of additional, exogenously provided agents, such as stains, dyes, binding agents, etc. In various embodiments, optical spectroscopic methods can be used to analyze one or more extrinsic attributes of a microorganism, for example, a property that can only be detected with the aid of additional agents. In various embodiments, a variety of types of spectroscopy can be used, including, for example, fluorescence spectroscopy, diffuse reflectance spectroscopy, infrared spectroscopy, terahertz spectroscopy, transmission and absorbance spectroscopy, Raman spectroscopy, including Surface Enhanced Raman Spectroscopy ("SERS"), Spatially Offset Raman spectroscopy ("SORS"), transmission Raman spectroscopy, and/or resonance Raman spectroscopy or any combination thereof.

Spectroscopic detection can be carried out by any technique known to those of skill in the art to be effective for detecting and/or identifying one or more intrinsic or extrinsic attributes of a microorganism. For example, front face fluorescence (where the excitation and emitted light enters and leaves the same optical surface, and if the sample is generally optically thick, the excitation light penetrates a very short distance into the sample and can be used for identification of microorganisms. Other forms of measurement, such as epifluorescence, reflectance, absorbance, and/or scatter measurements, can also be employed.

Typically, the light source, or excitation source, results in the excitation of the sample, followed by measurement of the emission of fluorescence of the sample at predetermined time points or continuously. Similarly, the reflected light from interaction of the excitation source with the sample may be measured to provide pertinent data for identification and/or characterization. The emission from the sample may be measured by any suitable means of spectral discrimination, such as by employing a spectrometer.

A sample illumination source, or excitation source, may be selected from any number of suitable light sources as known to those skilled in the art. Any portion of the electromagnetic spectrum that produces usable data can be used.

In various embodiments, detection methods may be used that rely on fluorescence signal (e.g., intrinsic fluorescence or fluorescence due to the presence of added indicator dyes) due to excitation by a UV, visible spectrum, or IR light source. The light sources can be continuum lamps such as a deuterium or xenon lamps for UV and/or a tungsten halogen lamp for visible/IR excitation. Since these light sources have a broad range of emission, the excitation band can be reduced using optical bandpass filters. Other methods for emission wavelength spectral width that may be utilized include an acousto-optic tunable filter, liquid crystal tunable filter, an array of optical interference filters, prism spectrograph, and the like. Alternatively, lasers are available in discrete wavelengths from the ultraviolet to the near infrared. Any of a variety of fluorescence signal-based multiplexing methods will be known to those skilled in the art and are within the scope of the present disclosure.

Alternatively, light emitting diodes can be used as narrowband excitation light sources. LED's are available from a peak wavelength of 240 nm to in excess of 700 nm with a spectral width of 20-40 nm. The same methods for the reduction of spectral width can be incorporated with the LED's to improve discrimination between excitation and emission spectra. In various embodiments, a plurality of narrowband light sources, such as LEDs or lasers, may be spatially and/or temporally multiplexed to provide a multi-wavelength excitation source.

The emission from the sample may be measured by any suitable means of spectral discrimination, most preferably employing a spectrometer. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device ("CCD") camera or detector array. In one embodiment, a discriminator allows the observation of the fluorescence and/or scattering signal by a photodetection means (such as a photomultiplier tube, avalanche photodiode, CCD detector array, a complementary metal oxide semiconductor ("CMOS") area sensor array and/or electron multiplying charge coupled device ("EMCCD") detector array. Fluorescence signal strength at several different wavelengths are acquired and saved in a computer memory.

The detection of growth could also be accomplished using Raman spectroscopy. Raman spectroscopy is a non-contact technique where the sample is illuminated by laser radiation. The scattered light is either elastically or inelastically scattered by interaction with the molecules which comprise the microorganism. The elastically scattered light is referred to as Rayleigh scattering and the inelastically scattered light is Raman scattering. Raman spectroscopy has been shown to be a potentially viable method of microorganism identification and/or characterization by examination of the vibrational spectra of the microorganism.

The laser illumination and scattering collection optics are designed to focus the beam to a near-diffraction limited spot size. This size ensures adequate laser signal on the microbe since Raman scattering is very inefficient. The collection optics are designed to efficiently capture scattered light and couple it into an optical spectrometer for analysis. The Raman signal can be acquired at one or more locations and the subsequent signal averaged.

Once Raman spectra are obtained, they may be analyzed for location and strength of key peaks in the spectra. This data may be compared to a stored reference data set of known microorganisms so that determinations of, for example, Gram type, morphological information, and species identification, can be obtained. A reference data set from known microorganisms can be obtained in the system and methods described herein, or may be obtained from a third party.

To enhance Raman (SERS) and fluorescence signals, microorganisms could either be coated with gold and/or silver nanoparticles in a sample preparation step, and/or the inner optical surface could be pre-coated with metal colloids of particular size and shape. In various embodiments, the nanoparticles may be associated with microorganisms in a centrifugation step.

In various embodiments, spectra such as fluorescence spectra obtained using various methods described above may be used to perform identification of microorganisms. Reference spectra may be obtained for known microorganisms, thus allowing for correlation of measured sample data with characterization of the microorganisms of interest using various mathematical methods known to those skilled in the art. The measured test data from known microorganisms is stored in machine-readable memory, e.g., within the instrument itself or within an associated data processing device, such as a connected computer-based system. For example, the data from samples being tested by the instrument may be compared with the baseline or control measurements utilizing software routines known to or within the ability of persons skilled in the art to develop. More particularly, the data may be analyzed by a number of multivariate analysis methods, such as, for example, General Discriminant Analysis ("GDA"), Partial Least Squares Discriminant Analysis ("PLSDA"), Partial Least Squares regression, Principal Component Analysis ("PCA"), Parallel Factor Analysis ("PARAFAC"), Neural Network Analysis ("NNA") and/or Support Vector Machine ("SVM"). These methods may be used to classify unknown microorganisms of interest in the sample being tested into relevant groups (e.g., species) based on existing nomenclature, and/or into naturally occurring groups based on the organism's metabolism, pathogenicity and/or virulence in designing the system for evaluating, detecting and/or characterizing the organism as described herein.

In other embodiments, the microorganisms associated with a detection device can be interrogated using mass spectrometry techniques, such as MALDI-TOF mass spectrometry, desorption electrospray ionization ("DESI") mass spectrometry, GC mass spectrometry, LC mass spectrometry, electrospray ionization ("ESI") mass spectrometry and Selected Ion Flow Tube ("SIFT") spectrometry.

A variety of other detection methods and analytical tools have been used to detect and/or determine values associated with various attributes of a microorganism, including, for example, optical density, nephelometry, densiometry, flow cytometry, capillary electrophoresis, analytical chemistry and indicator-based methods of metabolite detection, protein output, molecular diagnostics, impedance, quartz crystal microbalance, bioluminescence, microcantilever sensors, and asynchronous magnetic bead rotation, among others. Of the various methods that have been described herein, some, such as various optics based methods, surface plasmon resonance, and atomic force microscopy, are compatible with non-destructive measurement or detection of individual, living microorganisms and can be used to evaluate microorganism growth and/or development of a multicellular clone. Some of these methods are furthermore capable of resolving and providing multiple measures or data points for a particular, individuated microorganism at any given point in time. Any method, as may be currently in practice or developed in the future, may be used to determine a value associated with an attribute of a microorganism for use in determining a growth rate, as disclosed herein.

Analysis

In various embodiments, and with reference to FIG. 1, a system 100 may comprise a sample 110, and input system 120, a sample analyzer 130, an analysis module 140, and/or a healthcare information system ("Healthcare IS") 150. System 100 may be configured to evaluate individual microorganisms, collect data associated with the individual microorganisms in response to events, analyze the data, and determine an attribute of the microorganism.

In various embodiments, sample 110 may be any suitable biological sample containing a microorganism. For example, sample 110 may be a biological fluid (e.g., blood or other bodily fluid), a laboratory specimen from a culture, or any other suitable sample containing a microorganism. Sample 110 may be collected from a patient in a healthcare setting. Moreover, sample 110 may be collected for diagnostic, treatment, scientific, or any other suitable purpose.

In various embodiments, input system 120 may be any system capable of receiving, processing, handling, dispersing and/or otherwise preparing a sample (see, for example, U.S. Pat. Nos. 7,687,239 and 7,341,841, the entire contents of which are incorporated by reference herein). Input system 120 may comprise a sample input capable of receiving samples 110 from any suitable source (e.g., a vial, a test tube, a culture, an assay, and/or the like). Input system 120 may be operatively coupled to sample analyzer 130. More specifically, Input system 120 may comprise a distribution system capable of preparing and routing samples to a sample analyzer 130. The distribution system may comprise a manifold capable of receiving a plurality of samples. The distribution system may also comprise one or more pumps and plumbing to route the plurality of samples to the sample analyzer. Input system 120 may be capable of processing and/or preparing sample 110 prior to, during, or after transport of sample 110 from the distribution system to sample analyzer 130.

In various embodiments, sample analyzer 130 may be any hardware, software, or hardware-software system capable of evaluating and collecting data about sample 110. Sample analyzer 130 may comprise any suitable microorganism evaluation, measuring, and data collection devices. Sample analyzer 130 may comprise any instrument or be capable of performing any evaluation and/or data collection process, steps, and/or method described herein with respect to microorganism detection. More specifically, sample analyzer 130 may be capable of detecting, evaluating, characterizing, or otherwise analyzing one or more individuated microorganisms.

In various embodiments, analysis module 140 may be any hardware, software, or hardware-software system capable of evaluating and collecting data about sample 110. Analysis module 140 may be operatively coupled and/or in electronic communication with sample analyzer 130. Analysis module 140 may be capable of receiving and processing microorganism information from sample analyzer 130. For example, analysis module 140 may be capable of receiving image data associated with a microorganism. The image data may represent one or more individuated microorganisms, populations of individually identifiable microorganisms, other information associated with a sample, information regarding debris and noise, and any other suitable information collected, analyzed and/or received by sample analyzer 130. Moreover, analysis module 140 may be operatively coupled and/or in electronic communication with input system 120. Analysis module 140 may receive patient and/or sample data from input system 120 and/or sample analyzer 130 (e.g., information indicating the source of the sample, characteristics of the sample, sample collection information, and/or the like).

Analysis module 140 may be further capable of processing and/or analyzing the microorganism information. For example, analysis module 140 may be capable of parsing the information, assess various characteristics of a microorganism (e.g., location, growth rate, mass, doubling, and/or the like). Analysis module 140 may also be capable of identifying parsed data that is not indicative of or associated with a microorganism (e.g., debris, noise, and/or the like). Further, analysis module 140 may be capable of associating various characteristics of one or more microorganisms with events and/or conditions. For example, analysis module 140 may be configured to evaluate a growth rate of an object and/or object site over time. Analysis module 140 may also evaluate multiple events and/or conditions over time. For example, analysis module 140 may be capable of evaluating a growth rate over time and associated with growth rate with specific events or conditions (e.g., the introduction of heat, the introduction of an antimicrobial agent, and/or the like).

The multivariable analysis capability of analysis module 140, also makes analysis module 140 capable of making a recommendation or determination about a microorganism based on one or more events or conditions. For example, based on a change or lack of change of a growth rate in response to an event or condition (e.g., the introduction of an anti-microbial agent), analysis module 140 may be capable of determining a characteristic (e.g., susceptibility to the antimicrobial agent) or the identity of the microorganism. As will be described in greater detail herein, analysis module 140 may evaluate and characterize the change or lack of change of the microorganism information and render a recommendation or determination of the microorganism characteristic.

In various embodiments, healthcare IS 150 may be any hardware, software, or hardware-software system capable of evaluating, receiving, processing, associated, and/or displaying microorganism information about sample 110. Healthcare IS 150 may be operatively or electronically coupled to analysis module 140 and/or any other component of system 100. Healthcare IS 150 may comprise one of more portals that are accessible to a healthcare provider. For example, Healthcare IS 150 may comprise an electronic medical record ("EMR") or other suitable patient health data management system that is capable of providing information and recommendations about a patient's condition.

In various embodiments and with reference to FIG. 1, system 100 may be a computer-based system for individuated microorganism detection, tracking and analysis. System

100 may be capable of event or condition triggered (e.g., time-lapsed) microorganism information capture.

In various embodiments, system 100 is fully automated and capable of handling various noise levels and signal intensity ranges, independent of illumination heterogeneities, and applicable to different individuated microorganism evaluation systems and methods (e.g., imaging modes, including dark-field, fluorescent, and phase contrast images, and/or the like). For example, locally determined background signal intensities may be used to compensate for illumination heterogeneities that may be introduced as a function of irregular illumination intensity from the illumination source or an irregular interaction of light emitted from the illumination source with the sample cassette.

Examples of image properties that make microorganism detection and clone tracking non-trivial include: high and varying levels of noise, uneven illumination, large amount of debris, and non-immobilized microorganisms.

In various embodiments, system 100 is capable of detecting individuated microorganisms. System 100 may be capable of performing, for example, method 200 and/or method 300.

Figure 2:
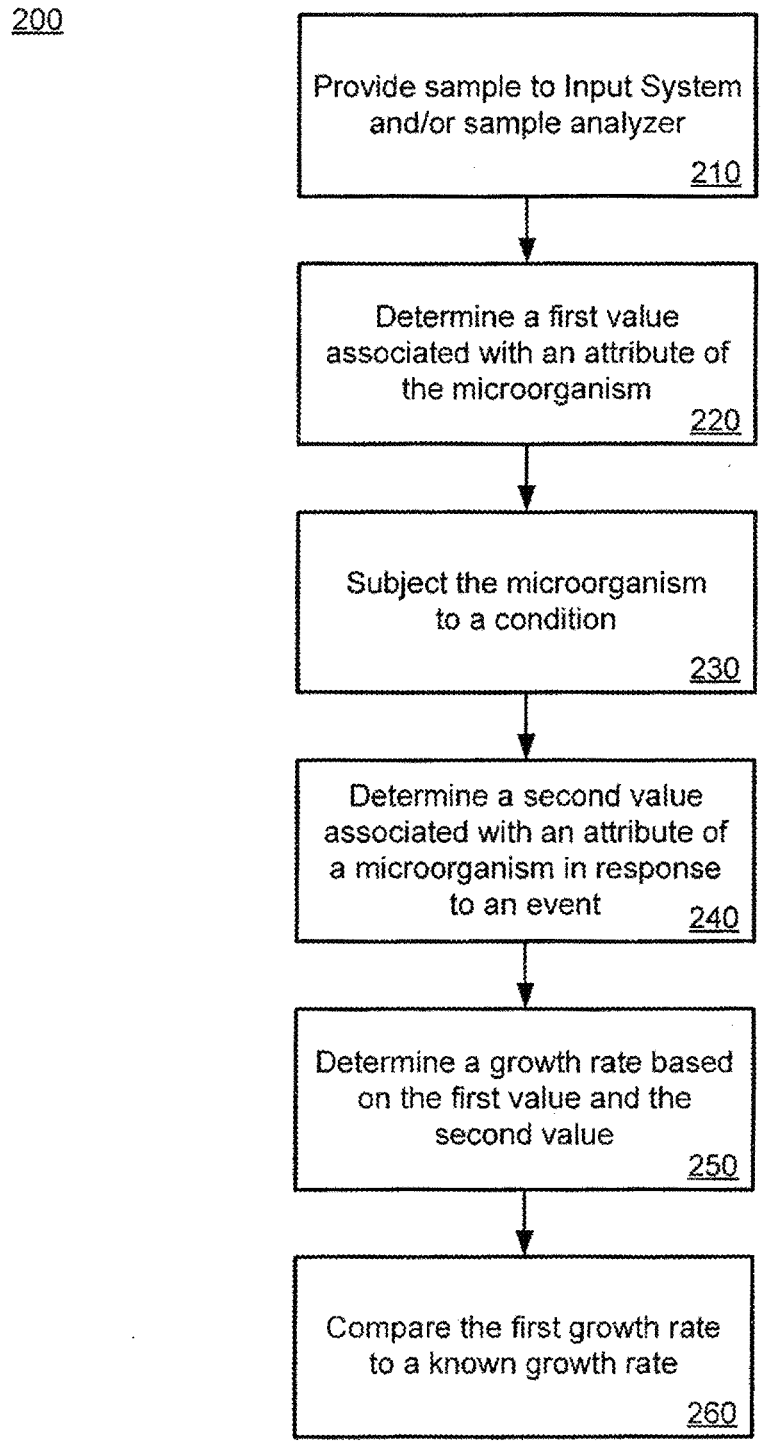
FIG. 2 illustrates a process for evaluating microorganisms.

In various embodiments and with reference to FIG. 2, system 100 may be capable of evaluating microorganisms. A sample containing microorganisms (e.g., a sample from a patient, a control sample, a research sample, and/or the like) for evaluation may be provided to any suitable component of system 100 (Step 210). The sample may be processed or prepared for evaluation in any suitable manner such as, for example, with input system 120. The sample may then be provided to sample analyzer 130. As described herein, sample analyzer 130 may be capable of detecting any attribute of a microorganism. In response to the sample being prepared and received by sample analyzer 130, sample elements (e.g., microorganisms, debris, and/or the like) may be analyzed or identified.

This analysis may include the evaluation of any suitable attribute of elements of the sample. In this way, sample analyzer 130 may evaluate and measure, characterize, sense or otherwise quantify one or more physical or non-physical attributes of elements of a sample to determine element information. System 100 may process and/or quantify these attributes in any suitable fashion. For example, system 100 may assign a first value to the each attribute or each element (Step 220). This first value may be a different first value for each detected, identified and/or analyzed attribute of each element.

The first value may be initially analyzed against a predetermined or dynamically determined range. This range may be associated with an attribute to be measured. In response to the attribute being within the range, system 100 may identify the element associated with the attribute as an element to be monitored. In response to the attribute being outside the range, system 100 may determine that the element associated with the attribute is an element that is not to be monitored.

In various embodiments, the sample and/or one or more elements may be subject to a condition (Step 230). The condition may be any suitable condition described herein. The condition may be introduced at any suitable time. For example, the condition may be introduced as part of sample preparation. The condition may also be introduced in response to and/or at a time or event after system 100 has identified or is evaluating the elements. The condition may also be introduced to the entire sample or to one or more portions of the sample.

In various embodiments, system 100 may evaluate the elements in response to and/or based on the condition. System 100 may be capable of collecting and or associating element information with the condition. Moreover, system 100 may be capable of collecting and associating element information based on or as a function of the condition. For example, the condition may be an exposure to a specific substance or time. In this example, system 100 may be capable of evaluating, correlating, and storing information about element attributes (or changes in an element's attributes in response to the condition and/or time). In this way, system 100 may be capable of determining a second value associated with an element attribute in response to an event (e.g., time) (Step 240). The second value may characterize a change or no change in an attribute and/or the element. As for the first value, the second value may be a different second value for each detected, identified and/or analyzed attribute of each element. Moreover, the second value may be a function of the first value and/or proportionally associated with the first value. As such, the second value, when compared to or analyzed with the second value may describe the nature of change of the first value. For example, system 100 may use the first value and the second value to determine a rate of change of an attribute (e.g., a grown rate of an element). Moreover, system 100 may use the second value or a comparison of the first value and the second value to determine whether an element is an element of interest (e.g., a microorganism).

The second value may also be analyzed against a second predetermined or dynamically determined range. This second range may be associated with the attribute being measured. In response to the attribute being within the second range, system 100 may identify the element associated with the attribute as an element to be analyzed or evaluated. In response to the attribute being outside the second range, system 100 may determine that the element associated with the attribute is not relevant for further analysis or evaluation (e.g., the element can be discarded or ignored).

In various embodiments, system 100 may be capable of assessing the response of the element to a condition (Step 250). For example, system 100 may determine a rate of change (e.g., a growth rate of an element) in the presence of the condition and in response to the event, based on the first value and the second value. This rate of change of an attribute of the element may be compared to a known or dynamically determined control rate of change (Step 260). In this way, system 100 may be capable of making a recommendation about an element, a condition, and/or an event based on the rate of change of the attribute measured. For example, the recommendation may comprise a determination that an element is susceptible to a condition based on a rate of change correlating with a control rate of change (or an associated rate of a control rate of change). The recommendation may comprise a determination that an element is resistant to a condition based on a rate of change not correlating with a control rate of change (or an associated rage of a control rate of change).

Microorganism Extraction from Evaluated Data

Figure 3:
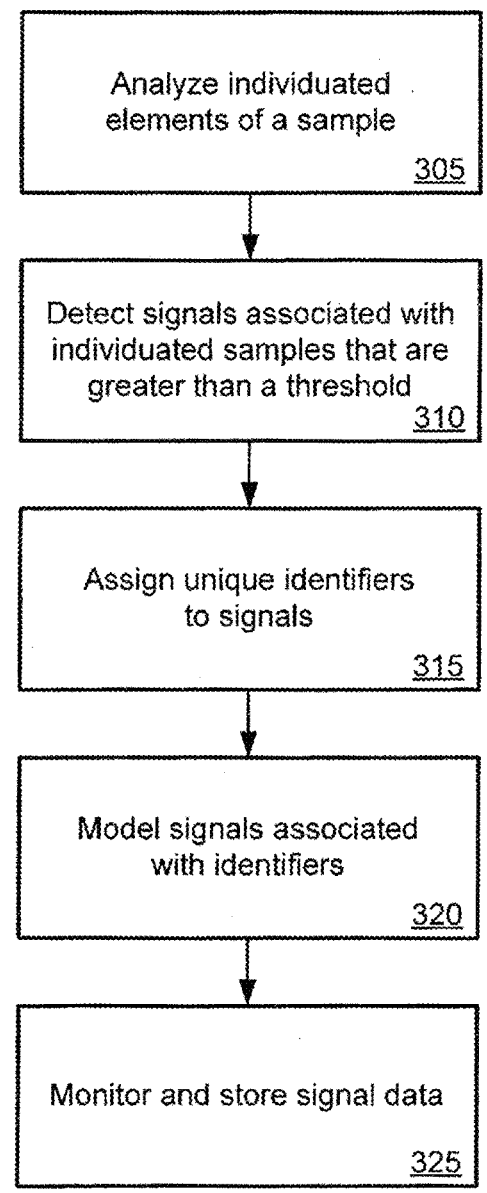
FIG. 3 illustrates a process for evaluating microorganisms.

In various embodiments, System 100 may be capable of analysis of individuated elements of a sample (FIG. 3, Step 305). Analysis module 140 may be capable of parsing evaluated data from sample analyzer 130 to identify local singularities (e.g., potential individuated organisms).

Signal Detection and Analysis

In various embodiments, detected signals and/or particles from data (e.g., an image) describing sample 110 (e.g., potential individuated organisms) are seeded or identified using the wavelet transform. More specifically, analysis module 140 is capable of detecting signals, spots, and/or singularities in the data that are greater than a threshold (Step 310). Analysis module 140 may detect signals having various properties including, for example, a range of intensities, a range of sizes, and a range of shapes. Each of the various properties may be associated with a predetermined threshold that characterizes the level of a significant signal versus noise. In this way, analysis module 140 may identify a signal as noise where a signal is not within a range (e.g., is not a significant signal). For example, in cases of image analysis for images with uneven background illumination, analysis module 140 is able to determine whether a signal is a significant signal.

Analysis module 140 may employ a wavelet transform for signal analysis. Analysis module 140 may employ the wavelet transformation and allow the signal to decompose the signal into one or more wavelet functions. These functions can be applied to the image. In response to applying the wavelet functions to the image, the analysis module 140 may generate one or more wavelet coefficients that represent an image on several levels of resolution (e.g., a stack of image planes).

For example, analysis module 140 may employ one or more wavelet transforms by successively constructing approximations of one or more signals (e.g., an image) at stepped or various resolution levels. For example, analysis module 140 may create a signal plane for a resolution level of an image, having a general amplitude of approximately zero and that has one or more points of amplitude (e.g., greater than or less than zero). These points of amplitude may correspond to particles (e.g., microorganisms, noise, foreign objects, debris, and/or the like) that can be filtered, identified or otherwise analyzed. As a result, analysis module 140 may reduce a signal (e.g., an image) to a sequence of approximations corresponding to the various resolution levels of the signal. Moreover, analysis module 140 may determine a sequence of the wavelet coefficients (e.g., points of amplitude) that characterize the details of the image. These wavelet coefficients when considered together with the approximations at the various levels of resolution describe the signal in a way that highlights the changes in the signal (e.g., the particles in the image), which may not be characterized in detail in the various approximation of the signal.

In various embodiments, analysis module 140 may employ wavelet transforms because the wavelet transforms are suitable for signal characterization (e.g., object detection in images). By employing wavelet transforms, analysis module 140 produces a characterization of a signal that is relatively sparse. Put another way, because the approximation of the signal plane has an amplitude that is near zero, points of amplitude may identify objects in a signal and the wavelet transform is helpful for identifying individuated microorganisms in a signal. This is so because the individuated organism can be described by a point of amplitude in the plane (e.g., a deviation for the near zero amplitude). Generally, this property of wavelet transforms may provide a representation where most of the wavelet coefficients are close to zero and only those that correspond to significant portions or features of the signal (e.g., an individuated organism or particle) are large. Moreover, the points of amplitude corresponding to significant portions and/or features of the signal persist through several resolution levels of the signal.

In various embodiments, by employing wavelet transforms, analysis module 140 may not require significant computation resources. In this way, analysis module 140 may perform signal analysis with minimal and/or generally available computer resources, because the wavelet transformation analysis is computationally efficient.

In various embodiments, analysis module 140 may employ any suitable wavelet function and associated wavelet transform for signal approximation. Each level k of the wavelet transform starts from an approximation image $A_{k-1}$ and produces two images. For example, analysis module 140 may determine a wavelet coefficient image $W_k$ by solving:

$$W_k(i,j) = A_{k-1}(i,j) - \tfrac{1}{4}\Sigma_{m,n} A_{k-1}(i+m, j+n),$$

with high pass filtering, where $A_0$ is an original image, $A_k$ and $W_k$ for k=1, ... , 8 are approximation and wavelet coefficient images respectively on a resolution level k, indices (m, n)={(−k, 0), (0, −k), (k, 0), (0, k)} for levels k=1, 3, 5, 7 and (m, n)={(−k, −k), (k, −k), (k, k), (−k, k)} for levels k=2, 4, 6, 8, and i, j∈{image area coordinates}. In response to determining $W_k$, analysis module 140 may approximate signal $A_k$ by low-pass smoothing of $A_{k-1}$, by solving:

$$A_k(i,j) = A_{k-1}(i,j) + \tfrac{1}{8}\Sigma_{m,n} W_k(i+m, j+n),$$

where $A_k$ and $W_k$ for k=1, ... , 8 are approximation and wavelet coefficient images respectively on a resolution level k, indices (m, n)={(−k, 0), (0, −k), (k, 0), (0, k)} for levels k=1, 3, 5, 7 and (m, n)={(−k, −k), (k, −k), (k, k), (−k, k)} for levels k=2, 4, 6, 8, and i, j ∈ {image area coordinates}.

In various embodiments, analysis module 140 may then reduce or eliminate noise in the signal by filtering out small wavelet coefficients that correspond to noise. Locations associated with points of amplitude within a predetermined threshold are retained as potential sample elements (e.g., organism locations) and points of amplitude outside the predetermined range are discarded as noise.

In various embodiments, analysis module 140 may determine an estimation of the wavelet coefficients that correspond to signal without noise on each resolution level of the wavelet transform. This estimation may be based on a Gaussian noise assumption and a non-informative prior distribution for the wavelet coefficient. The non-informative prior distribution may indicate that there is no initial assumption associated with data distribution The wavelet coefficient estimation for one resolution level may be calculated by solving:

$$W_k^{signal}(i, j) = \frac{(W_k^2(i, j) - \sigma_k^2)_+}{W_k(i, j)},$$

where $\sigma_k$ is a standard deviation of the wavelet coefficients that correspond to noise on the resolution level k and $W_k^{signal}(i, j)$ is a wavelet coefficient at location (i, j) on a resolution level k of a signal without noise.

The wavelet coefficient estimation may use a value of $\sigma_k$ for each resolution level of the wavelet transform. In various embodiments, analysis module 140 may estimate σ, based on an assumption that most of the wavelet coefficients correspond to noise. This assumption may allow analysis module 140 to determine noise wavelet coefficients using a median of the absolute value of wavelet coefficients by solving:

$$\sigma_k = \frac{\text{median}(|W_k(i, j)|)}{0.6745},$$

where the pixels (i, j) and corresponding $W_k$ (i, j) values included in the noise estimate are dependent on the resolution level k. To determine the resolution level k, analysis module 140 may decompose an original image into various levels (e.g., 8) of the wavelet transform as described above. This decomposition provides eight wavelet coefficient planes of the same size as the original image. Analysis module 140 may use one or more high resolution planes or the signal to filter out the noise. For each plane, analysis module 140 may deflate or normalize the wavelet coefficients by determining $W_k^{signal}$ (i, j) As a result, analysis module 140 may identify noise by determining which of the wavelet coefficients deflate or normalize to zero.

In various embodiments, analysis module 140 may also estimate $\sigma_k$ values for each plane. For example, analysis module 140 may create a noise mask for each plane. For the first plane (e.g., the highest resolution plane) the mask may include all wavelet coefficients. For the second, third, and fourth planes, the mask may include only the locations that are detected as noise (e.g., wavelet coefficients deflated or normalized to zero) in the previous plane. Analysis module 140 estimates the noise standard deviation for each plane based on the determination of $\sigma_k$ by using the wavelet coefficients that are covered by the noise mask.

In various embodiments, analysis module 140 may analyze the lower resolution planes (e.g., the fifth to eighth planes) to detect significant wavelet coefficients (e.g., sample elements or signal features that are not noise and that may correspond to organisms). Analysis module 140 may employ the same wavelet coefficient deflation procedure, namely the estimation of $\sigma_k$. However, analysis module 140 may employ a control based on a predetermined or dynamically determined rule. The rule may provide that the wavelet coefficients are set to zero in response to the wavelet coefficients being deflated or normalized to zero on both planes from paired planes (e.g., the fifth and sixth planes and/or the seventh and eighth planes in an eight plane analysis). In response to the normalization or deflation not being zero, the deflated wavelet coefficients can be set to one. As a result, each location corresponding to a one is not discarded altogether. Rather, the location is monitored as a potential seed site (e.g., a site where an organism is present). $\sigma_k$ values are estimated using all wavelet coefficients of the plane, there is no mask. This may be a two-step filtering process. For example, the first filtering step may detect noise and the second filtering step may detect particles. A mask may be used to define areas of an image that contain only noise wavelet coefficients.

In various embodiments, analysis module 140 may calculate wavelet coefficient correlation planes by taking products of the deflated wavelet coefficients at the same location on all of the various wavelet coefficient planes. This correlation may allow analysis module 140 to identify one or more correlation points across the various planes. In this way, analysis module 140 is able to determine potential microorganism locations, of variable size and morphology, in the presence of noise and uneven background illumination with a manageable frequency of false positive events while minimizing the frequency of false negative events.

Detection of Microorganisms

In various embodiments, analysis module 140 may assign unique identifiers (e.g., locations) to signals (Step 315). By monitoring the locations (Step 325), analysis module 140 may estimate morphological parameters of the identified signal objects (e.g., detected potential organisms).

In various embodiments, analysis module 140 may determine potential locations based on the particle seeding from a signal. Analysis module 140 may further evaluate the identified locations to determine which of the identified locations correspond to the actual microorganisms. As such, analysis module 140 may model each identified location (Step 320). For example, analysis module 140 may estimate particular attributes (e.g., detected or visual properties of a microorganism) to create an estimation of the particular sample element. The particular attributes may be associated with a microorganism location, such that microorganism attributes, activities and/or the like can be further evaluated, characterized or estimated by system 100. More specifically, analysis module 140 may create a microorganism object characterized by length and width in signal parameters (e.g., pixels in the context of an image), orientation angle in the plane on a signal (e.g., in radians), and height in signal intensity units of an image for each identified location. Additionally, analysis module 140 may determine the signal intensity of an object associated with the identified location (e.g., microorganism signal intensity may be calculated as a microorganism object parameter).

Analysis module 140 may estimate, determine, and/or characterize the dimensional parameters of objects at identified sites by fitting microorganism models to data associated with each location. The model may be characterized as a second-order surface such as, for example:

$$M_{ij}(x,y) = a^2 x^2 + b^2 y^2 + cxy + d.$$

Analysis module 140 may fit the surface associated with the location by minimizing the squared error to an original image at the location (i, j). The coefficients of the surface a, b, c and d are used to determine the parameters of the object associated with the location. For example, analysis module may calculate the length, width, and orientation angle of the object using the eigenvalue decomposition of the matrix $$\begin{bmatrix} 2a & c \\ c & 2b \end{bmatrix}.$$

Microorganisms may look like brighter circular or rod-like spots on darker background. Based on this determination, analysis module 140 may discard certain identified locations. For example, only objects and/or associated object locations with both positive eigenvalues or the larger positive eigenvalue may be retained as potential microorganisms. The height of the object associated with the location may be assigned the value of d.

Using the parameters determined for each object model at each identified location, analysis module 140 may create a microorganism object as a rectangular box with length and width equal to the corresponding microorganism object's length and width and the height of 1. Analysis module 140 may smooth the box by convolving with a Gaussian kernel of width 7. The resulting object height may be scaled up to the height of the microorganism object parameter d. This smoothed box may be used to calculate an error of the microorganism object as an absolute deviation between the smoothed box and the original image at the corresponding location. The error may be used as a threshold range or limit to identify microorganism object sites (e.g., organisms for evaluation) and eliminate debris and/or foreign objects that are not microorganism objects. For example, analysis module 140 may identify microorganism objects with errors of less than 300 as detected microorganisms. In response to meeting the threshold range, analysis module 140 may represent each selected microorganism as a microorganism object with corresponding parameters.

In various embodiments, analysis module 140 may determine and/or calculate a microorganism intensity parameter. The microorganism intensity parameter may be determined based on the sum of intensity of pixels in the original image covered by the microorganism object box minus image background for these pixels. If microorganism objects overlap, analysis module 140 may distribute the intensity value between overlapping microorganism object locations in proportion to the values of the microorganism object boxes over the corresponding pixel.

In various embodiments, analysis module 140 may create a background signal based on the first signal of the signal sequence (with the least number of microorganisms). The first signal may be transformed by deleting all areas that belong to any microorganism object (regardless of whether the microorganism object is retained as a microorganism or discarded because of a large fitting error). In response to the transformation, analysis module 140 may substitute the pixel values in these areas with the median of the lower 50th percentile of 800 closest pixels that do not belong to any other identified location and corresponding microorganism object. Analysis module 140 also smoothes the background image by a median filter of size 10 in order to eliminate noise. The smoothed background image may be saved and used as the background for all images in the sequence.

As such, analysis module 140 is able to estimate and/or characterize the length, width, and/or height of microorganism objects based on image local curvatures at identified locations. Moreover, analysis module 140 may reduce associated errors by eliminating identified locations and associated seed objects in response to the fit quality of microorganism object being outside a predetermined range with respect to the original image.

Clone Tracking

In various embodiments, analysis module 140 tracks each microorganism from the first image through the image sequence individually. Analysis module 140 may assign microorganisms in the first image to clones (e.g., divided or new microorganisms at a monitored object location). Moreover, analysis module 140 may create clone tracks as combinations of individual microorganism tracks from the same clone. This allows analysis module 140 to evaluate which microorganisms belong to which clone for the first image of the sequence, where the number of microorganisms is the smallest and clones are, likely, well separated. By creating an assignment or track for each clone, analysis module 140 may determine a baseline associated with microorganisms and clones from the first signal. Analysis module 140 may then evaluate the clone progress and/or behavior, automatically using the microorganism track assignments.

In various embodiments, analysis module 140 may employ one or more rules for determining track assignments. For example, a track may be a sequence of sets of microorganisms assigned to a particular track in each signal of a signal sequence. The track may start as one microorganism and each microorganism of the track can be associated with zero, one, or several microorganisms in the next signal of the sequence. Each microorganism in the first signal of the signal sequence can be a start of a microorganism track. The start or origin of each microorganism track corresponds to the first signal of the sequence and no new tracks can be created thereafter. Tracks can end before the end of a signal sequence. Microorganisms in a subsequent signal of the sequence should have predecessors in the previous signal. Microorganisms that are tagged as non-growing can be assigned as a predecessors to no more than one microorganism in the next signal of a sequence. The microorganism in the next signal should represent the same microorganism as its predecessor with high probability. Tracks may be created by associating microorganisms in a subsequent signal of the signal sequence with the closest microorganisms in the previous signal. This may be done by evaluating a change in a characteristic or event (e.g., a location) associated with a subject cell and an associated microorganism.

In various embodiments, the first signal sequence can be registered to eliminate alignment shifts from one signal to the next. Signal registration can be performed on signal sequences regardless of whether correlating elements between the signals are present in the signals. Correlating elements may be used as an alignment marker (e.g., fiducial marks in an image). Otherwise, the detected microorganisms may be used as alignment markers. Registration may be determined by finding the minimal translation of a signal that minimizes the mean squared error of its alignment markers with the previous signal in the sequence.

In response to registration, non-growing microorganism objects may be detected. For the first five cycles of the signal sequence each microorganism may be matched to the closest microorganism in the next signal in the sequence. As a result, analysis module 140 may determine a list of single-microorganism tracks through the first five cycles of the signal sequence. Analysis module 140 may calculate two measures of volume difference for all possible pairs of microorganisms in a track. The first measure may be the size of the non-overlapping volume of the microorganism models that are placed at the same location but retain their orientation. The second measure may be the difference in volume between the microorganism models regardless of their orientations. For the five cycle tracks there can be ten pairs of microorganisms that produce two vectors of difference measures of length ten. A microorganism in the first signal of the sequence can tagged by analysis module 140, as non-growing if the square root of the mean of the squares is less than 0.3 for the first vector of difference measures and is less than 0.5 for the second vector.

The implementation of the distance measure calculation for all microorganisms in a first image to all microorganisms in a second matrix may be computationally expensive, especially in cases of hundreds or thousands of microorganisms. Therefore, the distance measure may be calculated iteratively in order make the computational expense of this component of the tracking process feasible.

More specifically, analysis module 140 may place each microorganism from the first signal in the same signal with all microorganisms of the second signal. For each such microorganism configuration an adjacency matrix can be calculated with a Gaussian similarity function:

$$s(i,\ j) = \exp\frac{\|X_i - X_j\|^2}{2\sigma_{dist}^2}.$$

Analysis module 140 may determine that this adjacency matrix can be interpreted as a transition probability matrix of a random walk that jumps randomly between microorganisms. The distance parameter $\sigma_{dist}^2$ of the similarity function may be initially set to 60. The distance parameter may be set to this level to make the similarity function greater than zero for most microorganisms that are ancestors of the same microorganism.

Each microorganism in the first signal may be assigned a vector of likelihoods of being a predecessor for all microorganisms in the second signal based on the distance parameter. The Laplacian of the adjacency matrix s(i, j) may be constructed. Analysis module 140 may obtain eigenvectors that correspond to the smallest eigenvalues (<0.0005) of the Laplacian. These eigenvectors may approximate indicator functions of microorganism clusters in the microorganism configuration initially constructed. The eigenvectors may be combined as columns into the matrix U, and the matrix $Q=UU^T$ may be constructed. A row of a matrix Q that corresponds to a microorganism from the first signal is taken as a likelihood vector of this microorganism being the predecessor for the microorganisms on the second signal.

In various embodiments, as likelihood vectors for all microorganisms in the first signal being are collected, analysis module may associate each microorganism in the first signal with zero, one, or several microorganisms in the second signal. For each microorganism in the second signal, analysis module 140 evaluate whether any identified microorganism object may be a predecessor microorganism in the first signal, based on the highest likelihood value. Based on the highest likelihood value, analysis module 140 may make an association between microorganisms if the likelihood value is the highest for all first signal microorganisms.

In various embodiments, analysis module 140 may identify and separately analyze non-growing microorganisms. For example, analysis module 140 may associate non-growing microorganisms with zero, or one microorganism in the second signal, and the microorganism in the second signal should have similar signal characteristics to the microorganism in the first signal. For example, analysis module may use a similarity threshold of five-fold for both volume difference measures calculated during non-growing microorganism detection. Analysis module 140 may tag microorganisms in a subsequent signal that have been associated with non-growing microorganisms in a previous signal as non-growing microorganisms to propagate non-growing microorganisms through the signal sequence.

All microorganisms that are assigned track association are deleted from the second image and the association step is repeated until there are no possible associations left between two images. In this way, microorganisms identified in the second image are associated with and/or assigned to a clone in the first image.

In various embodiments, if there are non-associated microorganisms left in subsequent signal analysis module 140 initiates a tracking procedure. A new microorganism configuration associated with the subsequent signal for each microorganism of the previous signal may be created by removing all previously associated microorganisms from the subsequent signal except the ones that have been associated with the particular previous signal. As a result, analysis module 140 may increase $\sigma_{dist}^2$ and the non-associated microorganisms and repeat tracking through the signal sequence.

Analysis module 140 may associate and/or cluster microorganisms in the first signal of the signal sequence into clones. Analysis module 140 may associate the clusters based on the clones having the substantially similar spectral clustering distances which were identified during tracking. As such, analysis module 140 may create clone tracks that are combinations of microorganism tracks that start from the first image microorganisms of the same clone.

Growing Clone Detection

In various embodiments, analysis module 140 may detect potential growing clones base on a probability analysis. For example, analysis module 140 may assign a probability of being a growing clone or a value corresponding to a likelihood of being a growing clone to each tracked clone. The probability or likelihood value can be any suitable value. For example, the likelihood may be a value between zero and one, where one represents the highest likelihood. Analysis module 140 may also be configured to determine a growth likelihood value for each tracked clone. The growth likelihood value may be calculated as a product of two likelihood values (e.g., the clone signal intensity curve shape likelihood and the tracking error likelihood).

In various embodiments, analysis module 140 may further clarify, refine, and/or eliminate some tracked clones. For example, clones that are not tracked to the end of signal sequence may be assigned a growth likelihood value of zero.

In various embodiments, analysis module 140 may further characterize one or more tracked close based on signal intensity curves of tracked clones. The signal intensity curve for a clone may be quantified as the sequence of sums of intensities of a population (e.g., each individuated microorganism) assigned to the particular clone, which is evaluated or tracked in each signal of the signal sequence. For example, a cubic polynomial $p2^{x2}+p3^x+p4$ may be fitted to or approximate the natural logarithm of the signal intensity curve, where parameters p1, p2, and $p3^x$ and the mean squared error of the fit characterize features of the signal intensity curve. These features may serve as input for two logistics regression functions that in turn output the two likelihood values (e.g., clone signal intensity curve shape likelihood and the tracking error likelihood).

In various embodiments, analysis module 140 may determine the tracking error likelihood. The tracking error likelihood may be determined based on a logistic regression function that takes the mean squared error of the fit of the signal intensity curve as an input. This likelihood can represent an assumption that the logarithm of the signal intensity curve of a growing clone should have curve that is well approximated by a cubic polynomial.

In various embodiments, analysis module 140 may determine the clone intensity curve shape likelihood logistic regression function with cubic polynomial parameters p1, p2, and p3 as input. Based on this input, analysis module 140 may determine that the logarithm of the signal intensity curve of a growing clone should have a specific shape.

In various embodiments, analysis module 140 may determine any suitable variant response function. Similarly, analysis module 140 may be capable of characterizing a response based on any mathematical function and/or estimating the mathematical function associated with a response.

In various embodiments, the logistic regression functions have been constructed by fitting logistic regression models to a training set of tracked clones. The training set included examples of tracked growing and non-growing clones from several evaluations such as those described herein.

In various embodiments, analysis module 140 may fit a cubic polynomial to the logarithm of the signal intensity curve on a clone-by-clone basis for the signal sequence. Analysis module 140 may use a logistic regression function in the cubic polynomial parameter space to assign a growth likelihood value for a clone.

EXAMPLES

In various embodiments, the examples described herein can demonstrate evaluation of various aspects of microorganism attributes, as defined herein. The examples described herein can also demonstrate determination and/or characterization of changes in attributes (e.g., growth rate), in response to, for example, events or conditions. Moreover, the examples described herein may demonstrate analysis of the changes in attributes to make a determination of alternation of growth rates as compared to reference growth rates. Based on these determinations, the systems, methods and computer readable mediums (e.g., system 100), may perform the evaluation steps and provide one or more outputs based on the determined alterations.

Example 1

Identification and Growth Rate Quantitation of Individual Bacterial Clones Using a Novel Microfluidic Concentration Device The ability of the system of the present disclosure to provide immunochemical and microscopic identification and quantitative growth rate measurement by evaluating in near real time and in situ the mass increase of individual microorganisms was assessed. The system provides a rapid, accurate evaluation of growth dynamics for the population of viable organisms in the sample.

The system disclosed herein may be a bench top instrument that combines a disposable fluidic cartridge with automated microscopy and image analysis software. The system can include, among other features, automated sample distribution to multiple on-board analysis chambers providing integrated electrokinetic concentration and imaging, electrophoretic concentration to a capture and imaging surface using transparent indium tin oxide (ITO) electrodes and redox buffer system, phase contrast, darkfield, and fluorescence microscopy, XYZ motion control including autofocus, off-board (instrument-based) pumps and fluid media, on-board reagent reservoirs (antibodies, stains, antibiotics), and active on-device valving for fluidic network control.

Evaluations can be performed using the system, with off-board specimen preparation (i.e., simple centrifugation or filtration sample preparation). The system can provide rapid concentration of bacteria to assay capture and imaging surface using electrokinetic concentration. Targeted bacterial identification can be performed by fluidic introduction of species specific antibodies followed by fluorescently labeled secondary antibodies, with automated epi-fluorescent microscopy. Individual clones can be mapped and growth rate quantitation exploits registered time-lapse image analysis, processed to derive growth rate information (doubling times and growth rate constants). The system can also provide on-board, near real-time antibiotic susceptibility testing (AST).

A flowcell for use with the system can include indium tin oxide (ITO; conductive and transparent) coated glass as top and bottom layers, with an adsorptive chemical coating on the bottom surface (examples of coating are found in U.S. Pat. No. 6,844,028, the entire contents of which are incorporated by reference herein). A sample containing microorganisms is introduced and potential is applied. Since bacteria are generally negatively charged, they migrate to the positively charged surface, where they adsorb to the chemical coating. After electrokinetic concentration, the device is automatically filled with growth media (TSB). All subsequent assay steps are performed in media and microorganism viability is maintained throughout the process.

Bacterial species display unique surface antigens enabling specific immunolabeling. Proof of concept was demonstrated by concentrating a sample of mixed *Klebsiella pneumoniae* and *Haemophilus influenzae* to a surface and incubating with a mixture of anti-Kp and anti-Hi. Subsequent species-specific secondary fluorescent labeling identified bacterial species via fluorescent imaging, results of which are shown in FIGS. 6A-6D.

Growth rates were determined in accordance with various processes disclosed herein to identify microorganisms via threshold discrimination, and track growth by tabulating integrated intensity through a timed sequence of dark field images. Growth constants and doubling times of individual clones are derived as explained herein, and can be expressed as either individualized or aggregate subpopulation values.

Standard methods of microorganism growth rate quantitation measure optical density ($OD_{600}$) changes in a growing suspension culture. The experimental system was used to determine the aggregate growth rates of a panel of ten clinically relevant bacterial species, with the results compared to suspension culture measurements. The average difference of 18% sd 5% demonstrates a high degree of concordance in the methods.

Individual bacterial clone growth tracking enables evaluation of antibiotic susceptibility and resistance characteristics on a clonal basis within hours with near real time measurement.

TABLE 1

Exponential growth curve constants and doubling times of 6 tracked clones of *A. baumannii*. Average value derived from means of individual time points.

| Clone ID | k (min$^{-1}$) | R$^2$ | DT (min) |
|---|---|---|---|
| 45 | 0.0169 | 0.917 | 40.9 |
| 63 | 0.0174 | 0.973 | 39.9 |
| 83 | 0.0175 | 0.962 | 39.5 |
| 88 | 0.0175 | 0.967 | 39.5 |
| 106 | 0.024 | 0.983 | 28.8 |
| 113 | 0.0215 | 0.972 | 32.3 |
| Average | 0.018 | 0.986 | 38.6 |

Figure 5A:
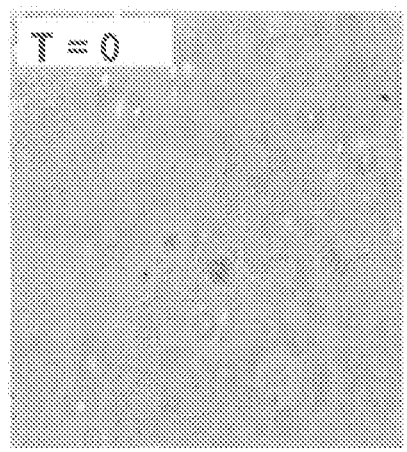
FIGS. 5A-5C illustrate an exemplary electrokinetic concentration (EKC) of *S. aureus*.
Figure 5B:
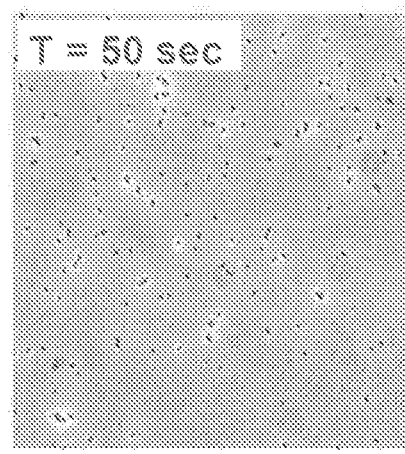
Figure 5C:
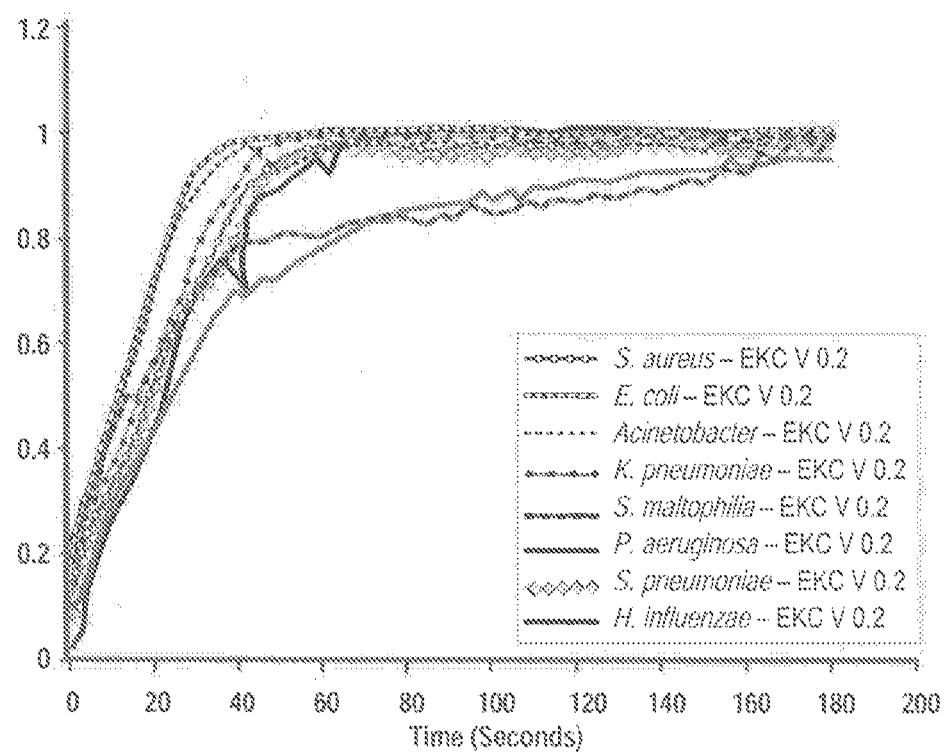

FIGS. 5A-5C illustrate electrokinetic concentration (EKC) of *S. aureus*. Phase microscopy image at time=0 (FIG. 5A) shows out-of-focus microorganisms in bulk solution beyond the image plane (surface). The image field of view is 202×187 μm. After 50 seconds of EKC, microorganisms have been driven to the surface and concentration is complete (FIG. 5B). During EKC, phase images are collected at a rate of approximately one per second, and image analysis in accordance with the present disclosure is used to rapidly count particles (microorganisms). FIG. 5C shows EKC curves for a panel of 8 clinically relevant bacterial species.

Figure 6A:
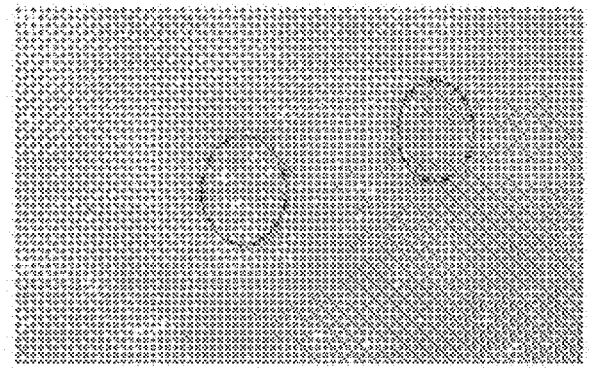
FIGS. 6A-6D illustrate exemplary evaluation data from immunolabeling of selected bacterial strains of *Klebsiella pneumoniae* ATCC 49472 and *Haemophilus influenzae* ATCC 10211.
Figure 6B:
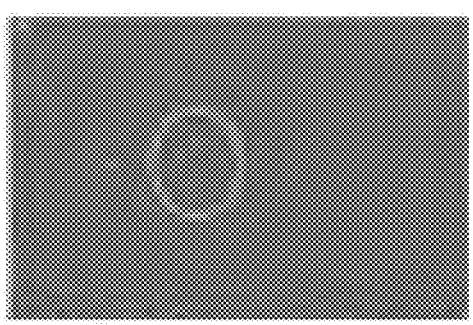
Figure 6C:
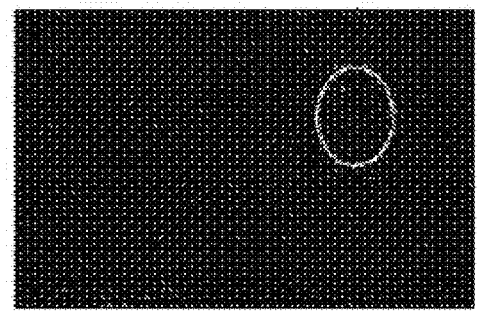
Figure 6D:
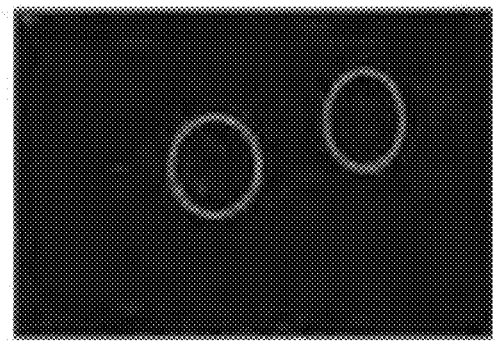

FIGS. 6A-6D illustrate immunolabeling of selected bacterial strains in accordance with various embodiments. A mixed sample of *Klebsiella pneumoniae* ATCC 49472 and *Haemophilus influenzae* ATCC 10211 was concentrated in a flowcell. A mixture of anti-*K. pneumoniae* and anti-*H. influenzae* was incubated in the cell, followed by fluorescently labeled secondary antibodies. Image acquisition with fluorescent microscopy demonstrates bacterial species labeling. FIG. 6A illustrates mixed bacterial concentrated to the surface. The circle to the left indicates *K. pneumonia* and the circle to the right indicates *H. influenza*. FIG. 6B illustrates *K. pneumonia* labeled with mouse anti-*K. pneumonia* and anti-mouse Alexa Fluor® 546 (goat anti-mouse IgG, Life Technologies, NY). FIG. 6C illustrates *H. influenza* labeled with rabbit anti-*H. influenza* and anti-rabbit Alexa Fluor® 647 (goat anti-rabbit IgG, Life Technologies). Circle indicates *H. influenza*. FIG. 6D illustrates *K. pneumonia* (left circle) and *H. influenza* (right circle).

Figure 7A:
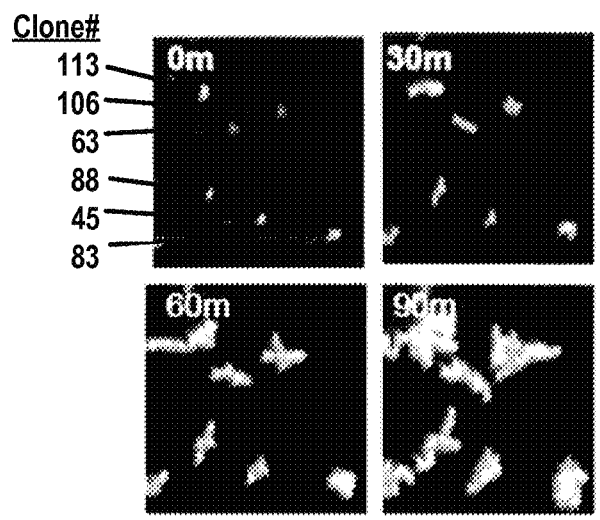
FIG. 7A illustrates a series of darkfield images of *Acinetobacter baumannii* showing growth over 90 minute period, with computer-based system derived clonal analysis.
Figure 7B:
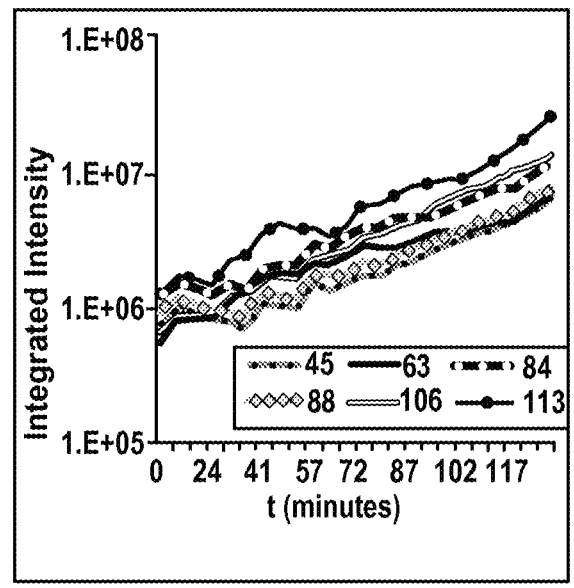
FIG. 7B illustrates integrated intensity curves of a dataset of 6 clones identified and evaluated using the system described herein.
Figure 7C:
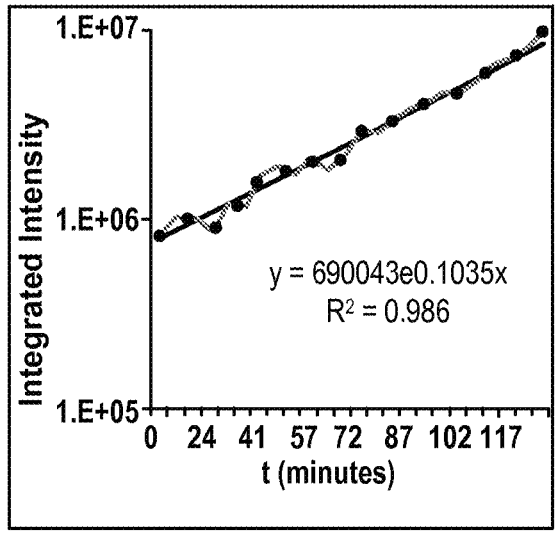
FIG. 7C illustrates a growth curve derived from the average integrated intensity values from each time point.

FIG. 7A illustrate a series of darkfield images of *Acinetobacter baumannii* showing growth over 90 minute period and microorganism analysis. Integrated signal intensity curves of a dataset of 6 clones identified and evaluated using the system described herein are shown (FIG. 7B). A growth curve derived from the average integrated intensity values from each time point is also illustrated (FIG. 7C).

Figure 8:
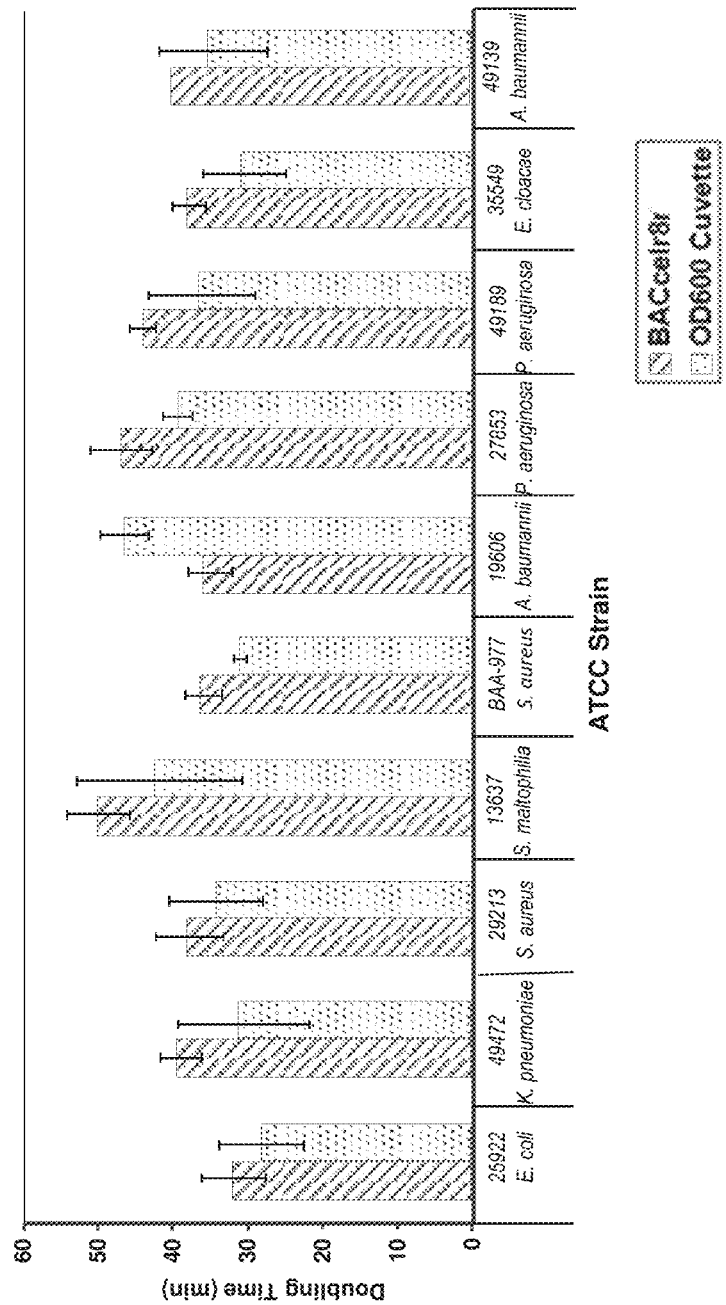
FIG. 8 illustrates doubling times in minutes of ten bacterial strains measured with various systems described herein.

FIG. 8 illustrates doubling times in minutes of ten bacterial strains, measured with the system of the present disclosure and by $OD_{600}$ change in broth culture suspension. Each value is the average of minimum three runs, with each run consisting of four replicates.

Figure 9A:
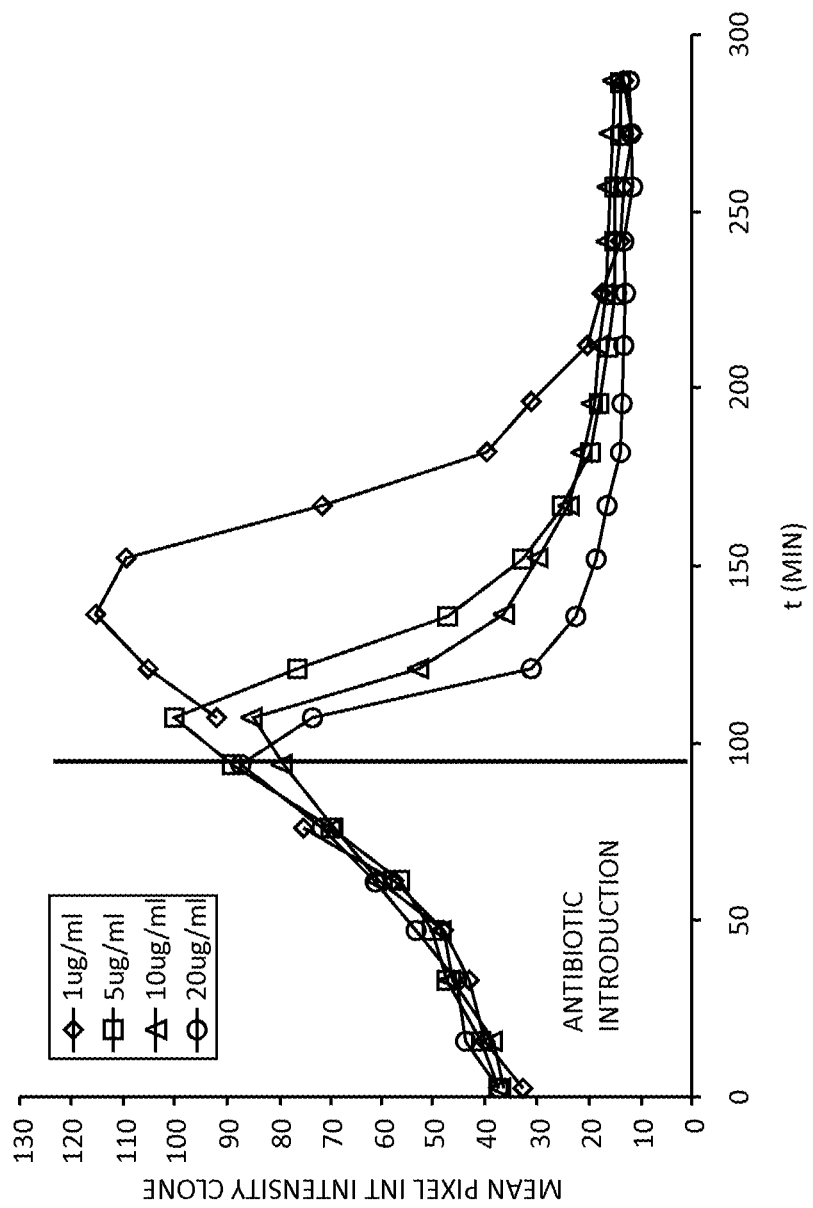
FIGS. 9A and 9B illustrate growth and kill curves in which *Klebsiella pneumoniae* was concentrated, grown, and dosed with varying concentrations of imipenem, a lytic antibiotic.
Figure 9B:
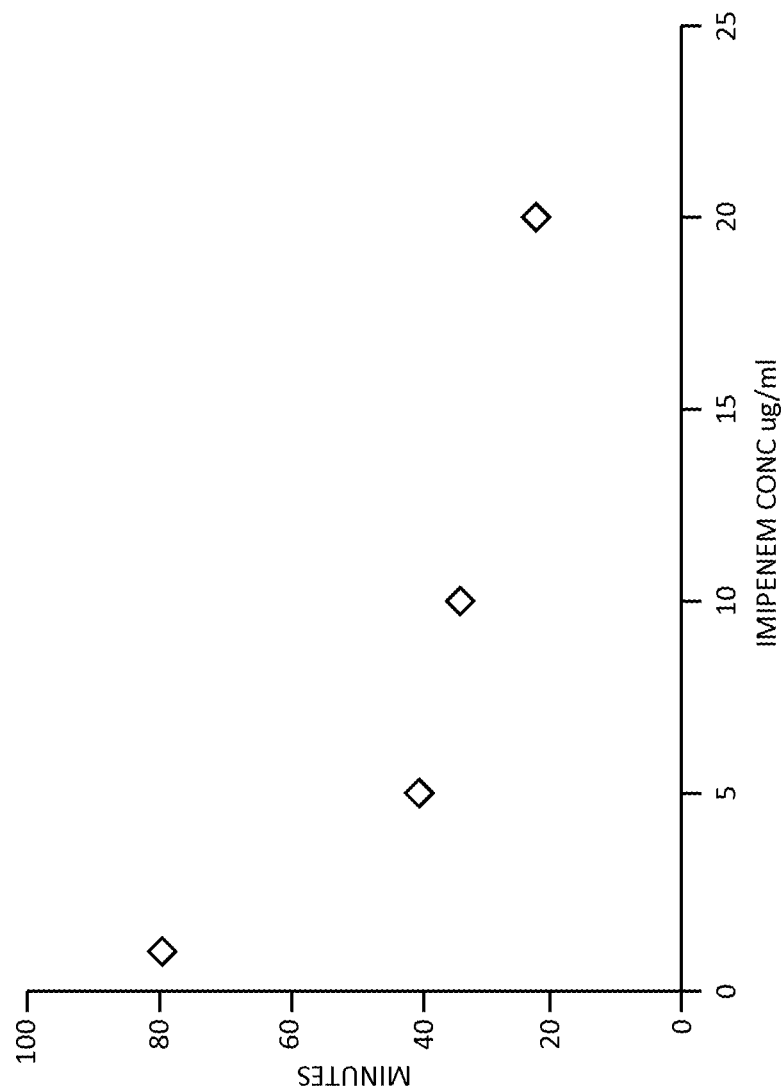

FIG. 9A illustrates growth and kill curves in which *Klebsiella pneumoniae* were concentrated, grown, and dosed with varying concentrations of imipenem, a lytic antibiotic. Tracking the decrease in integrated intensity after introduction of antibiotic reveals dose dependent kill rates. FIG. 9B shows 50% kill time as function of antibiotic concentration.

Example 2

Same-Day Blood Culture with Digital Microscopy

Introduction

Bacteremia due to multiple drug resistant organisms (MDRO) is increasing in frequency and growing in complexity. Critically ill patients who acquire a bloodstream infection must begin adequate antibiotic therapy as quickly as possible. For critically ill patients, resistance can render initial therapy ineffective, delaying the start of effective antimicrobial therapy. The requirement for overnight culture creates an unacceptable delay. Delay also prolongs exposure to broad-spectrum empiric therapy, creating selective pressure favoring emergent resistance. Systems and methods in accordance with various embodiments of the present disclosure, such as the multiplexed automated digital microscopy (MADM) system referred to with respect to the following examples, have the potential to reduce turnaround time by rapidly analyzing live bacteria extracted directly from a clinical specimen, eliminating the need for colony isolates. The purpose of this pilot study was to determine MADM system sensitivity, specificity, speed, and technical requirements for same-day analysis of live organisms extracted directly from blood. Tests used two of the most common ICU pathogens, *Staphylococcus aureus* (SA) and *Pseudomonas aeruginosa* (PA).

The MADM system used a custom microscope and pipetting robot, plus an evaluation system, as described herein. 32-channel disposable cassettes (FIG. 4A) enabled live microorganism immobilization for microscopy and fluid exchanges for different test agents. The microscope scanned 40 image fields in each flowcell channel, each channel having organisms extracted from about 3.5 µL of prepared inoculum.

Simulated blood specimens consisted of isolates spiked into 10 mL each of 29 aliquots of two short-fill CPD blood bank bags to make approximately 5 CFU/mL of bacterial target species, confirmed by quantitative culture. Spiked isolates included 14 *Staphylococcus aureus* (SA), 3 *Pseudomonas aeruginosa* (PA), or 12 non-target Gram-negative bacilli species. Dilution of each sample with 30 mL of modified TSB culture medium promoted growth. 20 additional control aliquots contained no spikes. 4-hour incubation at 35° C., followed with brief spin cleanup, ended with pellet resuspension into an electrokinetic buffer to make 1 mL samples for MADM system analysis. 20 µL sample aliquots were then pipetted into 14 cassette flowcells. A 5-minute low-voltage electrokinetic capture was performed to concentrate microorganisms on the lower surface of each flowcell where a capture coating immobilized the bacterial cells.

Liquid (40° C.) Mueller-Hinton agar with and without antimicrobials was then exchanged through each channel and gelled. Separate pairs of channels received antibiotics, which included the following antibiotics at the concentrations indicated: 32 µg/mL amikacin (AMK), 8 µg/mL imipenem (IPM), 6 µg/mL cefoxitin (FOX), or 0.5 µg/mL clindamycin (CLI). Cooling then gelled the agar, followed by incubation at 35° C. with microscope imaging at 10-minute intervals for 3 hours (concurrent with identification in other channels).

The system acquired dark-field images every 10 minutes. The analyzer applied identification algorithms to each individual immobilized cell that exhibited growth. 6 channels provided data for ID algorithms to score individual organisms and their progeny clones. ID variables included cell morphology, clone growth morphology, clone growth rate, and other factors. The analyzer computed ID probability based on the number of related clones and their scores. The system required 40 or more clones that exceeded a threshold score in order to proceed with analysis.

Controls included quantitative culturing, disk diffusion tests for isolate resistance phenotype, and 20 blood samples without spikes.

Results

Figures 10A, 10B, 10C:
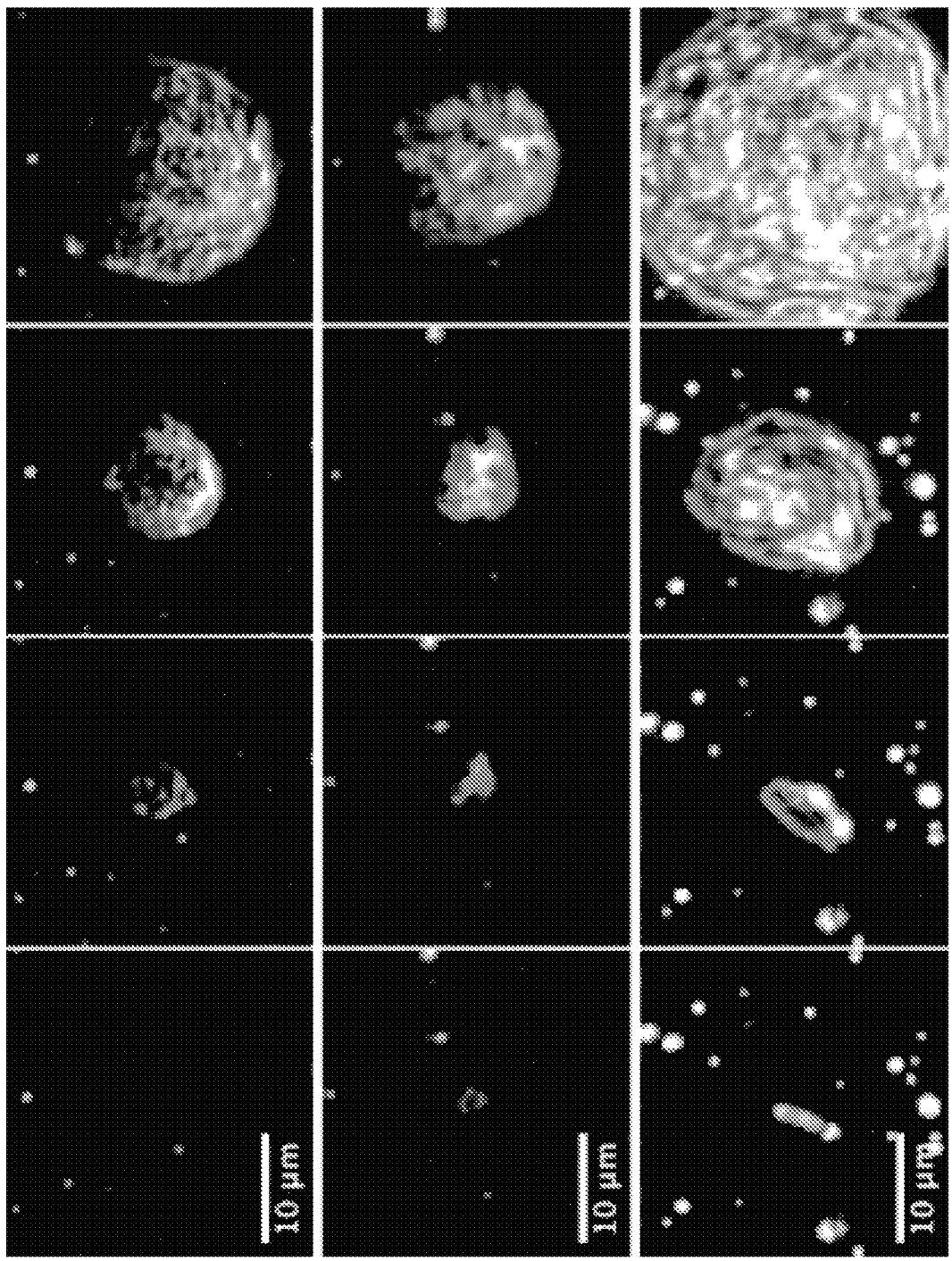
FIGS. 10A-10C illustrate time-lapse dark-field images of individual growing clones (GC).

Culture confirmed that normal growth occurred in the prepared samples. Organism detection required ≥4 growing clones (GC). Recovery yielded SA GC counts that exceeded CFU as determined by culturing because of near-complete clump disruption in most samples. Counting combined results in multiple channels when appropriate. Identification required ≥40 GC, and each phenotype test required ≥40 GC. The MADM system detected growth in 29/29 spiked samples and no growth in 20/20 non-spiked controls. Growth sufficient for ID occurred in 23/29 samples in the fixed 4-hour growth period. 4 SA samples clumped excessively, precluding ID scoring. 2 PA samples grew too slowly (<1.1 div/h) to achieve 40 GC in the growth period (5 h would suffice). SA growth rates were ≥1.5 div/h. The MADM system identified 1/1 PA and 10/10 SA. One false PA ID occurred out of 22 non-target samples to yield 100% sensitivity and 97% specificity. The false ID was attributable to a known imaging aberration, later corrected. FIGS. 10A-10C illustrate examples of dark-field images acquired using a system in accordance with various embodiments over a period of three hours, with time points at 0, 60, 120, and 180 minutes (from left to right). Clone growth is shown for SA without drug (FIG. 10A, no antibiotic), SA in 6 µg/mL FOX (FIG. 10B, cefoxitin), with growth indicating MRSA phenotype, and for a Gram-negative rod (*E. coli*) without drug (FIG. 10C) for morphology comparison. Brighter areas represent 3-dimensional growth effect (more light scattering from layering or end-on rod orientation). Non-growing particles are assumed to be debris.

The MADM system was used to identify drug resistance in 19/20 adequate samples with one false MSSA, yielding drug resistance phenotyping results with 89% sensitivity and 100% specificity. Table 2 summarizes SA data for overall concordance with comparator results.

Discussion

This pilot study asked whether major pathogens grow quickly enough to enable same-day diagnostic testing directly with bacteremic blood samples using microscopy. The MADM system had previously been used to analyze small numbers of live microbial cells extracted from other specimen types.

This study demonstrated that 4 hours of growth in a common nutrient medium provides enough live clones for MADM system analysis with fast-growing cells (>1.1 div/ hour growth rate in the conditions tested). PA required slightly longer times for adequate testing, estimated at 5 hours. These results provide parameters for determining requirements for practical application. Given the number of GC required for a test (40 with the study prototype), number of tests, and the slowest target organism growth, straightforward calculation derives the minimum growth duration needed. Fastest possible turnaround time results from maximizing growth rate while minimizing the GC needed per test, and minimizing the required number of tests and their duration.

TABLE 2

Identification of *S. aureus* drug resistance phenotypes using MADM system analysis.

| S. aureus | True Neg | True Pos | Accuracy |
|---|---|---|---|
| IDENTIFICATION (Adequate Growth N = 23) | | | |
| MADM-Pos | 0 | 10 | Sens 100% (CI 66%-100%) |
| MADM-Neg | 23 | 0 | Spec 100% (CI 72%-100%) |
| PHENOTYPE: MRSA (Adequate Growth N = 10) | | | |
| MADM-Pos | 0 | 4 | Sens 80% (CI 30%-100%) |
| MADM-Neg | 5 | 1 | Spec 100% (CI 46%-100%) |
| PHENOTYPE: CLI-R (Adequate Growth N = 10) | | | |
| MADM-Pos | 0 | 4 | Sens 100% (CI 40%-100%) |
| MADM-Neg | 6 | 0 | Spec 100% (CI 52%-100%) |

Within 8 hours starting with blood, automated microscopy successfully identified target pathogens and detected drug resistance phenotypes for a major species of live bacterial cells extracted directly from a small volume of simulated bacteremic blood. Diagnostic analysis using individual live-cell methods enables rapid turnaround without first requiring colony isolates. The probabilistic identification scoring achieved high concordance with clinical lab results. Resistance phenotype analysis also achieved high concordance. This analytical strategy can also use responses of individual clones to identify organism subpopulations and resistance phenotypes within polymicrobial specimens.

Conclusion

Application of systems and methods in accordance with various embodiments of the present disclosures, such as MADM system analysis, enables diagnostic analysis of live microorganisms extracted after brief growth in culture medium with high specificity and sensitivity.

Example 3

3-Hour ESBL Detection from Positive Blood Cultures Using a Multiplexed Automated Digital Microscopy (MADM) System Introduction Infections due to Gram negative bacteria expressing ESBLs are increasing in frequency and growing in complexity. ESBL drug resistance expression can be difficult to accurately detect by standard culturing methods, and is associated with multiple drug resistance in nosocomial and community infections. For critically ill patients, the likelihood for treatment success is related to the time required to initiate effective antimicrobial therapy. At best, confirmatory tests now require at least one day to perform with isolate culturing. In contrast, automated microscopy has the potential to reduce turnaround time by detecting complex resistance phenotypes directly in positive culture broth. The purpose of our study was to determine the sensitivity, specificity, and speed of automated microscopy to detect ESBL expression in clinically significant isolates of Enterobacteriaceae.

Materials and Methods

Direct observation of microorganism response to antibiotic exposure was performed on a disposable 32-channel fluidic cassette (FIG. 4A) inserted into a custom bench-top evaluation system in accordance with various embodiments of the present disclosure that combines digital microscopy, motion control, and image analysis. The system was used to measure growth of immobilized bacteria in a multichannel fluidic cartridge. Cassette flowcells were constructed with transparent top and bottom surfaces to allow microscope imaging.

Multiple institutions provided clinical strains. The collection included 24 strains of Enterobacteriaceae known to be ESBL-positive, and 32 known to be ESBL-negative. Strains included *K. pneumoniae* (14 neg, 11 pos); *K. oxytoca* (1 neg); *E. coli* (12 neg, 7 pos); *P. mirabilis* (1 pos); *E. cloacae* (3 neg, 4 pos), *E. aerogenes* (1 pos); *S. marcescens* (1 neg); and *C. freundii* (1 neg). Quality control strains included CLSI standard strains from the ATCC. CLSI ESBL confirmatory disk diffusion tests (DD) served as the comparator.

10 mL of banked whole blood in CPD was spiked into BACTEC Plus Aerobic/F bottles (BD), followed by an isolate spike using the above-listed clinical isolates to make 103 CFU/mL final concentration. Bottles incubated overnight (16 hours) at 35° C. with agitation. Centrifuged 100 µL culture aliquots were resuspended in 500 µL of a low ionic strength buffer to lyse blood cells. Further 5,000-fold dilution used an electrokinetic buffer to produce inocula. 20 µL buffer-resuspended aliquots of the inocula were pipetted into each flowcell and electrokinetic concentration captured live cells onto the flowcell surfaces. Antibiotics were then introduced into each flowcell. ESBL detection used 4 separate fluidic channels, each receiving a 20 µL inoculum containing 256 µg/mL of ceftazidime (CAZ) or cefotaxime (CTX) with or without 4 µg/mL of clavulanic acid (CA). Total preparation time averaged 20 minutes prior to placing the cassette on the microscope stage. Each 20× magnification field of view for microscopy contained approximately 4 to 40 growing clones, and each flowcell channel contained 40 separate fields of view. The system acquired darkfield images of 40 separate fields of view for each condition (each flowcell) every 10 minutes for 3 hours, computed the mass of each channel's cell population during the test, and compared the mass ratio in the antibiotic-only to its paired +CA channel. Thus, the system performed 6 concurrent assays in separate flowcells for each isolate, summarized in Table 3, below:

TABLE 3

Assay conditions for growth evaluation and detection of
ESBL positive blood cultures using MADM system.

| Growth control (no drugs) | Clavulanic acid (CA) 4 µg/mL |
|---|---|
| Ceftazidime (CAZ) 256 µg/mL | CAZ-256 + CA-4 |
| Cefotaxime (CTX) 256 µg/mL | CTX-256 + CA-4 |

The clone-by-clone growth analysis was performed for each isolate under each test condition using the image analysis algorithm. The system classified ESBL status by computing the growth in each drug with or without CA, using the ratio of clone mass. The system classified an isolate as ESBL positive if the mass ratio achieved a threshold, compound criteria using both drugs. The comparator was a CLSI confirmatory ESBL disk diffusion (DD) assay.

Results

The MADM system correctly classified 24 of 24 ESBL-positive strains (100% sensitivity), and 30 of 32 ESBL-negative strains (94% specificity) within three hours after inoculum introduction. The average maximum mass ratio of ESBL-negative isolates was 2.4±5.4 s.d. while the average for ESBL-positives was 96±113 s.d. Sensitivity was 100% (CI 84%-100%) and specificity 94% (CI 78%-99%).

Figure 11:
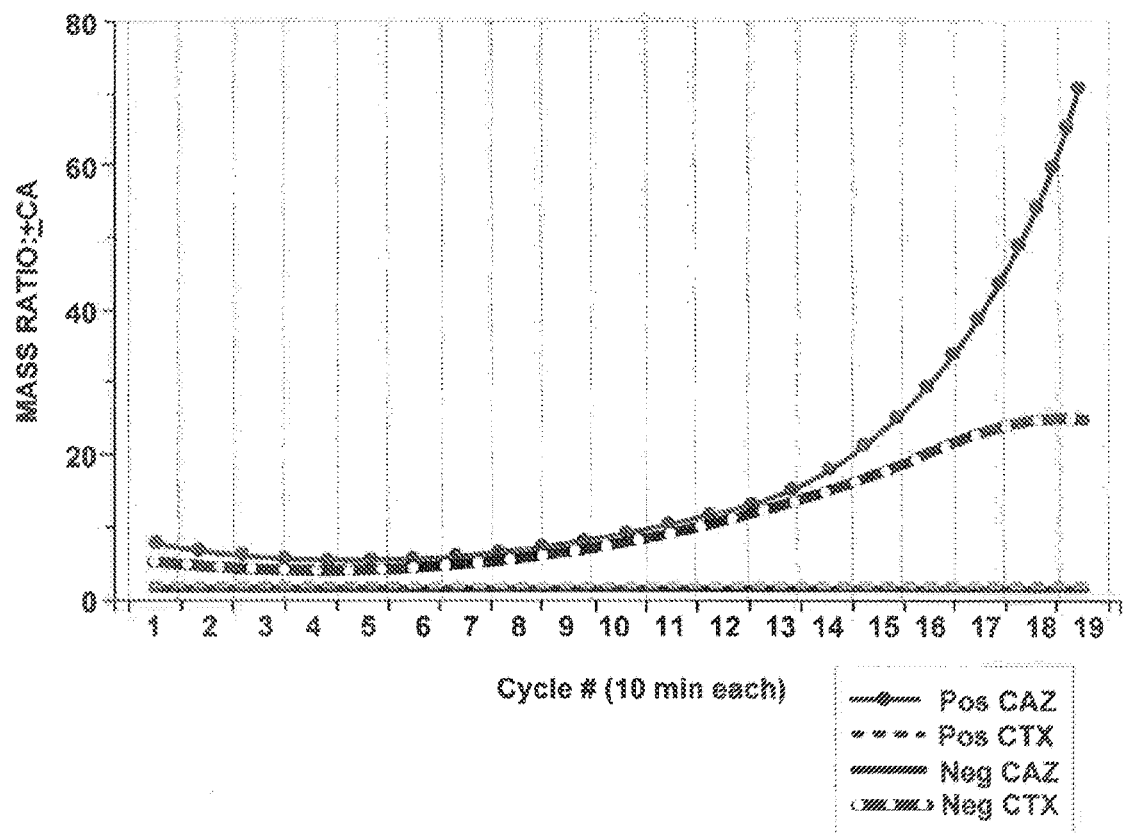
FIG. 11 illustrates growth curves of an extended-spectrum beta-lactamase positive (ESBL+) bacterial strain and a ESBL-negative (ESBL−) bacterial strain.
Figure 12:
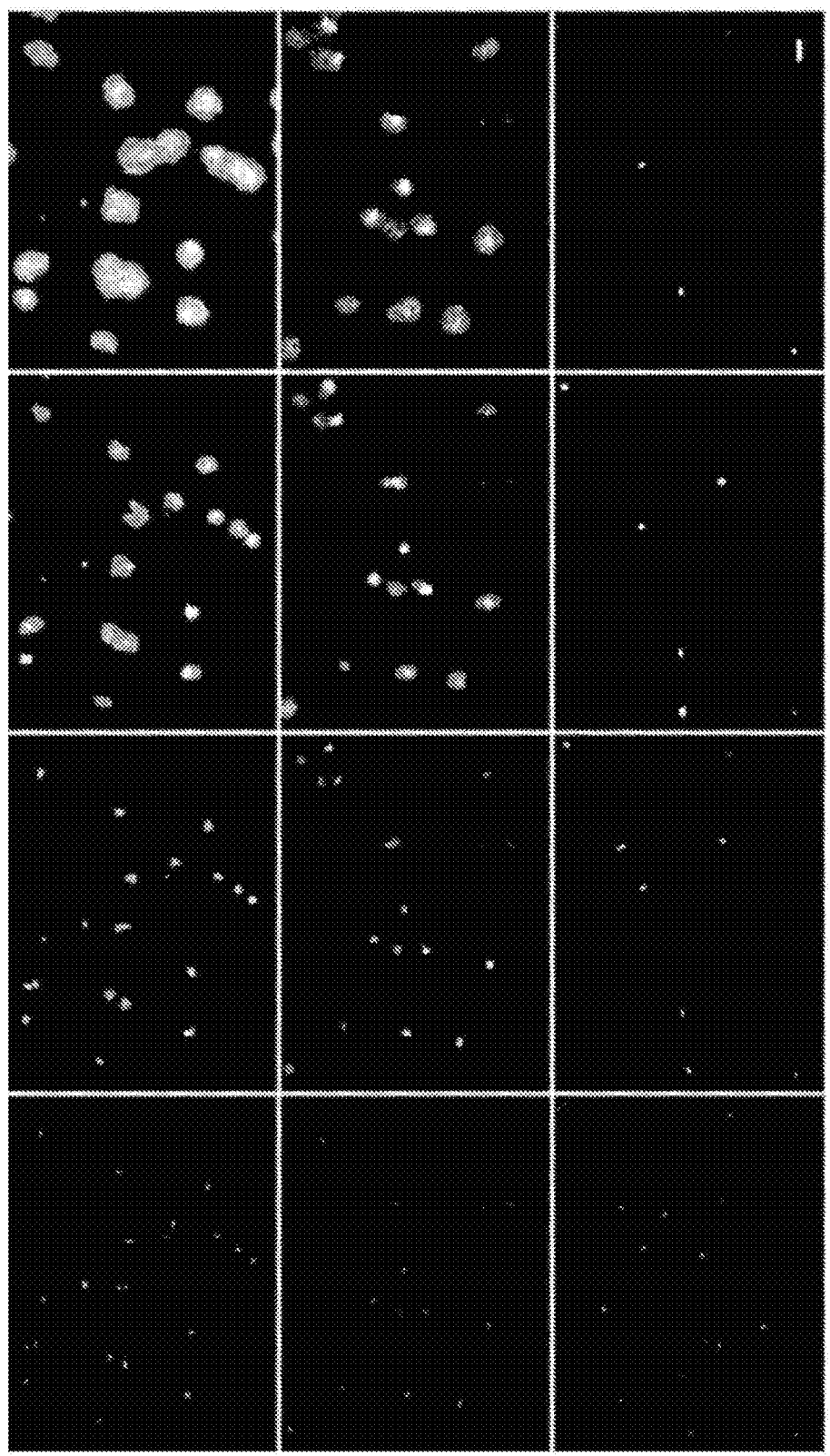
FIGS. 12A-12C illustrate *K. pneumoniae* ESBL+ growth in various conditions.
Figure 13:
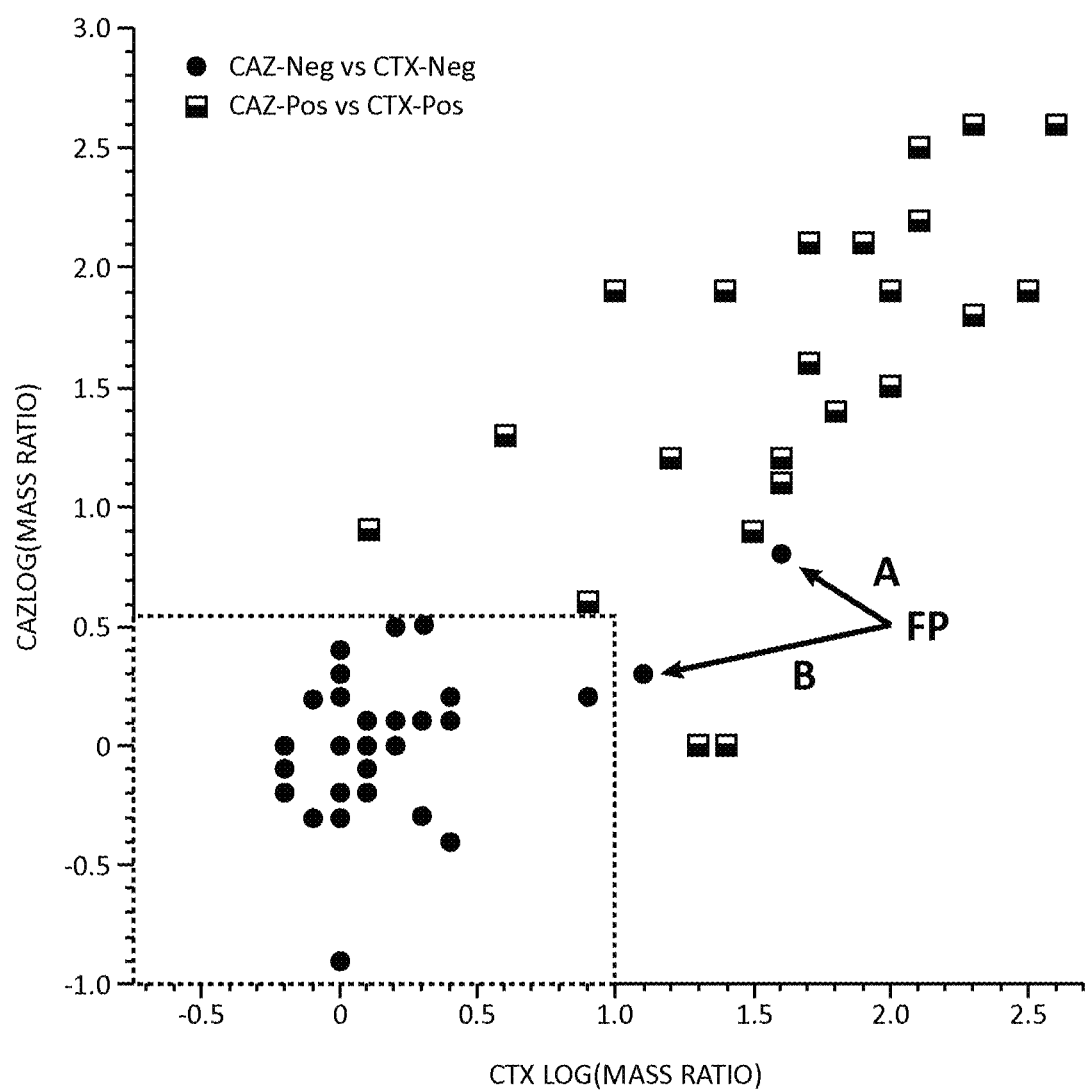
FIG. 13 illustrates a scatter plot of mass ratios with and without combination with clavulanic acid (CA).

FIG. 11 illustrates growth curves for one positive ESBL+ (*E. cloacae*, upper curves), and one negative ESBL– (*E. coli*, lower curves) strain identified using the MADM system. The data is illustrated as mass ratios between drug alone (ceftazidime CAZ) or cefotaxime (CTX)) and drug with CA (CAZ or CTX). FIGS. 12A-12C illustrate images at hourly intervals of an ESBL– positive strain, *K. pneumoniae* ESBL+. Rows show clone images at 60-minutes intervals starting after a 20-minute delay to first image during antibiotic exposure. FIG. 12A illustrates drug-free *K. pneumoniae* ESBL+ growth control. FIG. 12B illustrates *K. pneumoniae* ESBL+ growth in the presence of CAZ. FIG. 12C illustrates *K. pneumoniae* ESBL+ growth in the presence of CAZ+CA. A 20 µm scale bar is shown (lower right). FIG. 13 illustrates a scatter plot of mass ratios for the two agents (CAZ or CTX) in the presence and absence of CA with all strains. Two false positives occurred (FP). One (A) had marginal disk zone differential (4 mm) and the other (B) exhibited delayed drug effects. Squares indicate ESBL positives by DD, and dots indicate ESBL negatives. The dashed box outlines the original interpretation criterion zone.

One false-positive occurred for a *K. pneumoniae* strain that had DD values of 11 and 15 mm, just below the 5 mm difference required, and produced microcolonies in the zones. It is indicated as datum "A" in FIG. 13. An *E. coli* strain, indicated as strain "B" in FIG. 13, was clearly negative by DD but had an initial CAZ growth difference that disappeared after 90 minutes. This suggested a rule change to compensate for potentially delayed drug action.

Conclusions

This study demonstrates direct 3-hour blood culture pathogen ESBL resistance phenotype detection using automated microscopy. It extends other MADM system studies that used respiratory specimens and additional resistance phenotypes. Direct measurement of the magnitude and kinetics of clavulanate synergy enabled sensitive, specific, and rapid detection of the ESBL phenotype using a single challenge concentration of each antibiotic. The analytical speed of the automated system was consistent with that required to help de-escalate empiric therapy in critically ill bacteremic patients.

Example 4

Same-Day ID and Resistance Phenotyping Directly from Respiratory Specimens by Automated Microscopy Introduction Nosocomial infections due to multiple drug resistant (MDR) bacteria are increasing in frequency and growing in complexity. For critically ill patients, resistance can render initial therapy ineffective, delaying the start of effective antimicrobial therapy. But standard diagnostic cultures introduce a 2-3 day delay to provide guidance. Rapid, same-day, direct-from-specimen ID and AST of respiratory specimens could reduce clinical morbidity and mortality. Systems and processes for evaluating microorganism in accordance with various embodiments of the present disclosure, such as a multiplexed automated digital microscopy (MADM) system described and used in the following example, have the potential to reduce turnaround time by rapidly analyzing bacteria extracted directly from a clinical specimen. A pilot study using respiratory specimens was performed to compare analysis performed using a multiplexed automated digital microscopy (MADM) system with traditional cultures-based approaches. The purpose of our study was to determine the speed and accuracy of a MADM system as an alternative to culturing with same-day quantitation, identification, and resistance phenotyping. Customized MADM systems used commercial inverted microscopes with 12-bit monochrome cameras. A computer system ran custom image analysis and experiment control software. 32-channel disposable cassettes (FIG. 4A) enabled live microbial cell immobilization for microscopy and fluid exchanges for different test media and reagents.

A total of 281 de-identified remnant respiratory specimens were collected from hospital and commercial sources. The specimens included 25 endotracheal aspirates (ETA) of unknown age obtained from a specimen vendor. Also included were 230 mini-bronchoalveolar lavage (mini-BAL) and 26 ETA specimens obtained from Denver Health Medical Center (DHMC). DHMC specimens were 7-21 days old. AST results were available for all mini-BAL specimens but not for ETA. Accompanying reports also included semi-quantitative ID used to select 92 bacteria-positive specimens for analysis using the MADM system. Targets included *Pseudomonas aeruginosa*, *Acinetobacter baumannii* complex, and *Staphylococcus aureus*. Controls used standard culturing methods (Cx).

After culture re-test, 79 specimens demonstrated quantitative culture ("qCx") values above the diagnostic threshold (1e4 for mini-BAL and 1e5 CFU/mL for ETA). These specimens were prepped for introduction into the MADM system. The system performed quantitative ID for *Staphylococcus aureus* (STAU), *Pseudomonas aeruginosa* (PSAE), and *Acinetobacter* spp. (ABCC). Concurrent quantitative culture (qCx) was performed on specimens. The MADM system performed resistance phenotype tests on STAU-containing specimens for cefoxitin (FOX) MRSA phenotyping and clindamycin (CLI) resistance. The system tested ABCC- and PSAE-containing specimens for amikacin (AN) and imipenem (IMP) resistance.

Specimen preparation used a brief procedure to release bacteria, reduce imaging background, and suspend bacteria in a low ionic strength buffer. We rejected 13 specimens reported as positive but for which repeat qCx failed to confirm content. We rejected 10 samples with heavy interfering background when dilution to $OD_{600}=0.3$ yielded organism counts inadequate for analysis. We rejected 7 samples for other technical deficiencies. The remaining 62 specimens were tested using the MADM system.

20 µL samples of prepared specimen were pipetted into independent flowcell channels and a low-voltage electrical field was applied for 5 minutes. The electrical field concentrated bacteria onto a functional surface coating that immobilized the bacteria on the lower flowcell surface. Each flowcell channel received only one type of test reagent solution that contained a selective agent if required (only for channels used to test AB, sulbactam 32 µg/mL).

The instrument acquired images at 10-minutes intervals for 180 minutes, using 10 fields of view in each flowcell channel through a 20× objective. Imaging used darkfield illumination. Identification variables included response to selective agents (AB with sulbactam), cell morphology, growth morphology, and growth rate.

Identification algorithms applied to each individual immobilized bacterial cell. The system measured the amount of change in mass over time to compute growth rates. Identification consisted of computing and combining probability scores for morphology, response to selective media, and growth rates to produce a receiver operating characteristic curve (ROC) to derive classification criteria.

Results

Figure 14A:
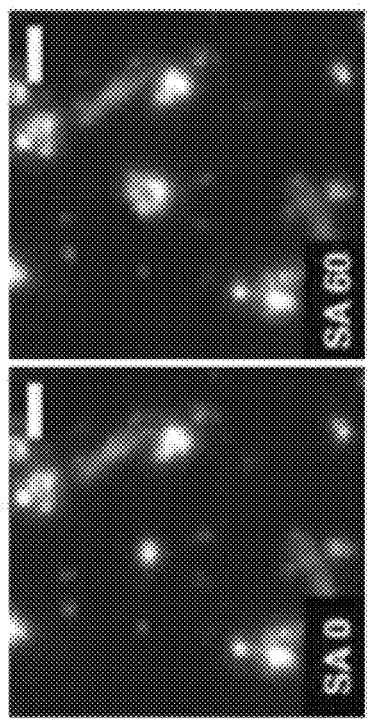
FIGS. 14A-14D illustrate darkfield images of bacterial growth at approximately time=0 and 60 minutes. Scale bars=5 μm.
Figure 14B:
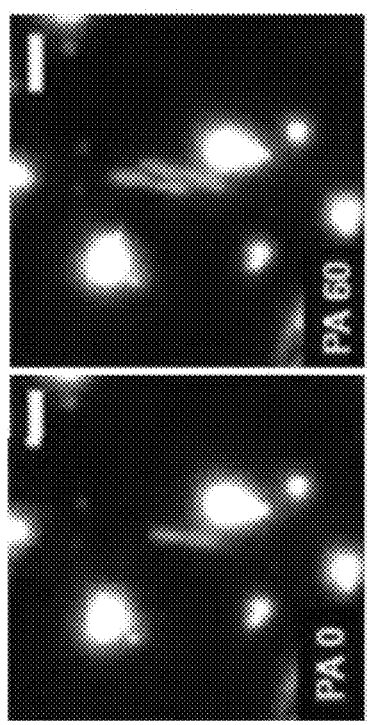
Figure 14C:
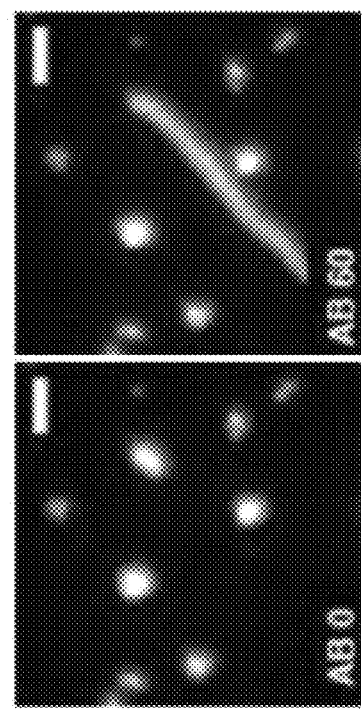
Figure 14D:
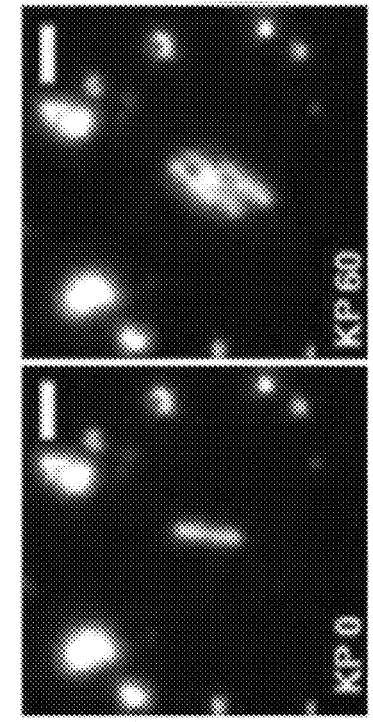

FIGS. 14A-14D illustrate organism growth after one hour to exemplify microscopy images used for time-lapse quantitative analysis. 80% of specimens had multiple species, but none had multiple target species. FIG. 14A illustrates *Staphylococcus aureus* (SA) growth at 0 and 60 minutes. FIG. 14B illustrates PA growth at 0 and 60 minutes. FIG. 14C illustrates *Acinetobacter baumanni* (AB in 32 µg/mL sulbactam) growth at 0 and 60 minutes. FIG. 14D illustrates *Klebsiella pneumonia* (KP, non-target) growth at 0 and 60 minutes. Non-growing pixel blobs are considered debris.

Dark field illumination revealed specimen matrix residue pixel blobs with a broad range of size and morphology. The system distinguished live microorganisms by requiring measurable growth as well as morphologic criteria in accordance with various aspects of the present disclosure.

MADM system results were concordant with repeat qCx in 59/62 specimens. Identification scoring algorithms for STAU yielded 14/14 true positives (TP), 45/45 true negatives (TN), 2 false positives (FP), and 1 false negative (FN); for ABCC 1/1 TP, 60/61 TN, 1 FP; for PSAE 3/3 TP, 59/59 TN. Two specimens yielded false positives for STAU and one yielded a STAU false negative. Overall ID performance was 95% sensitivity and 99% specificity. 2 specimens had STAU that expressed the MRSA phenotype by MADM (FOX) and Cx (OXA), and one by MADM system analysis only. None of the STAU expressed CLI-resistance. All PSAE and ABCC were susceptible to IMP and AN. MADM system resistance detection was concordant with hospital AST results except with one STAU sample (MSSA by oxacillin MIC, MRSA by FOX in the MADM system). For the 186 ID tests, Table 4 summarizes performance. Times to results were 1 hour for specimen prep and 3 hours to all analytical results for a total of 4 hours specimen-to-answer. Table 5 summarizes resistance phenotype results, with one discordant MRSA false positive.

TABLE 4

| ID performance, MADM vs. Cx. | | |
| --- | --- | --- |
| Sensitivity | 95% | CI95 = 73%-100% |
| Specificity | 98% | 94%-100% |
| Positive Predictive Value | 86% | 64%-96% |
| Negative Predictive Value | 99% | 96%-100% |
| Positive Likelihood Ratio | 53 | |
| Negative Likelihood Ratio | 0.05 | |

TABLE 5

| Target-positive specimens. | | | | | | | | | |
| --- | --- | --- | --- | --- | --- | --- | --- | --- | --- |
| SPECIMEN | TYPE | ID | Cx CLI | MADM CLI | Cx MRSA | MADM MRSA | Cx AN | MADM AN | Cx IMP | MADM IMP |
| DH 425 | Mini-BAL | STAU | S | S | S | R | | | | |
| DH 427 | Mini-BAL | STAU | S | S | S | S | | | | |
| DH 439 | Mini-BAL | STAU | S | S | R | R | | | | |
| DH 440 | BAL | STAU | S | S | S | S | | | | |
| T12 | ETA | STAU | S | S | R | R | | | | |
| ETA 280667 | ETA | STAU | NA | NA | NA | NA | | | | |
| DH 457 | BAL | STAU | S | S | S | S | | | | |
| DH 485 | BAL | STAU | S | S | S | S | | | | |
| DH 500 | BAL | STAU | NA | NA | NA | NA | | | | |
| DH 509 | BAL | STAU | S | S | S | S | | | | |
| DH 514 | Mini-BAL | STAU | S | S | S | S | | | | |
| DH 543 | BAL | STAU | S | S | S | S | | | | |
| DH 550 | BAL | STAU | S | S | S | S | | | | |
| DH 556 | Mini-BAL | STAU | S | S | S | S | | | | |
| DH 430 | Mini-BAL | PSAE | | | | | S | S | S | S |
| DH 554 | BAL | PSAE | | | | | S | S | S | S |
| DH 641 | Mini-BAL | PSAE | | | | | S | S | S | S |
| | | ABCC | | | | | NA | S | S | S |

NA = not analyzed:
STAU = *S. aureus*:
PSAE = *P. aeruginosa*:
ABCC = *Acinetobacter* sp.
CLI = clindamycin:
AN = amikacin:
IMP = imipenem:
Cx = culture result Discussion 2 false positive STAU IDs resulted from incorrect speciation (1 chained cocci, 1 *Enterococcus*). Test optimization or fastidious media could improve future versions. One ABCC false positive was *Enterobacter* sp. The false negative STAU had too few clones to meet the call criterion. Scanning more fields of view resolves this problem. The MRSA discordance arose in Cx with oxacillin, which is no longer considered the most reliable phenotyping agent (FOX, as used in the MADM system analysis). The small number of cells required for analysis is compatible with the bacterial concentration at BAL diagnostic threshold of $10^4$ CFU/mL and ETA at $10^5$ CFU/mL.

Conclusions

A multiplexed automated digital microscopy system in accordance with various embodiments of the present disclosure accurately analyzed live immobilized bacteria extracted directly from mini-BAL and ETA specimens. Total specimen-to-answer time was 4 hours.

Example 5

Automated 4-Hour Detection of Heteroresistant Vancomycin-Intermediate *Staphylococcus aureus* (hVISA)

Introduction

Infection with heteroresistant organisms can be difficult or impossible to detect by standard antibiotic susceptibility culturing methods using MIC criteria. Of particular concern, heteroresistance by *S. aureus* to vancomycin (VAN) may be emerging as a diagnostic challenge. The magnitude of the problem remains obscure because VAN-heteroresistant *S. aureus* (hVISA) exhibits MICs within the susceptible range but may lead to VAN failure. This leaves the microbiological laboratory community unable to perform adequate epidemiological and clinical studies. The purpose of our study was to determine assay criteria for multiplexed automated digital microscopy (MADM) system to rapidly identify the hVISA phenotype in individual live organisms using abbreviated population analysis profiles (PAP). Numbers of individual organisms tested fell within the range obtainable directly from lower respiratory specimens.

Materials and Methods

Customized MADM systems in accordance with various embodiments of the present disclosure used commercial inverted microscopes with 12-bit monochrome cameras. The computer-based system ran custom image analysis and experiment control software, as described herein. 32-channel disposable cassettes (FIG. 4A) enabled live microorganism immobilization for microscopy and fluid exchanges for different test media and reagents.

We characterized *Staphylococcus aureus* (SA) clinical isolates along with isolates from a Centers for Disease Control (CDC) SA collection using 48-hour broth microdilution abbreviated population analysis profiles (BMD-PAP), which served as the control. A total of 30 isolates were characterized. We also applied BMD-PAP to hVISA reference strain Mu3 (ATCC 700698), and measured areas under the curve (PAP-AUC) in all tests.

BMD-PAP consisted of serial isolate concentrations from 1 to 106 CFU/mL dropped onto sectors of VAN agar plates containing from 0 to 6 µg/mL in 10 steps (non-doubling dilutions) and counting colonies. An isolate met the hVISA+ detection threshold criterion if its BMD-PAP-AUC ≥0.9 Mu3 AUC. This study did not attempt to discriminate between hVISA and VISA, as designated by the plus sign in hVISA+.

For MADM system analysis, each independent flowcell channel, an example of which is illustrated in FIG. 4B, contained 10 µL of 106 CFU/mL (pipette introduction). A capture coating immobilized individual microorganisms for microscope image acquisition and spatial mapping. A wash displaced the sample fluid with Mueller-Hinton media containing different VAN concentration for each flowcell, from 0.01 to 4 µg/mL, plus one antibiotic-free growth control channel. The system evaluated changes in mass of each growing clone in accordance with various embodiments of the present disclosure. Each treatment flowcell channel received one of the following VAN concentrations: 0, 0.01, 0.05, 0.1, 0.2, 0.4, 0.8, 1.0, 2.0, or 4.0 µg/mL.

The instrument acquired images at 10-minutes intervals for 90 minutes, using three fields of view in each flowcell channel through a 20× objective and darkfield illumination. In each channel, the system approximately 1,000 growing clones. It then counted the number of clones from the same population sample that exhibited at least 4-fold gain in mass by the end of a 4-hour analysis period. Computation normalized the latter count by dividing it by the initial count. The abbreviated AUC was also determined and compared to microdilution PAP AUC By plotting abbreviated PAPs for these normalized counts, we then selected an AUC value for the abbreviated PAP region that yielded the best discrimination between hVISA+ and VSSA strains determined by BMD-PAP AUC and the Mu3 reference AUC.

Results

Figure 15:
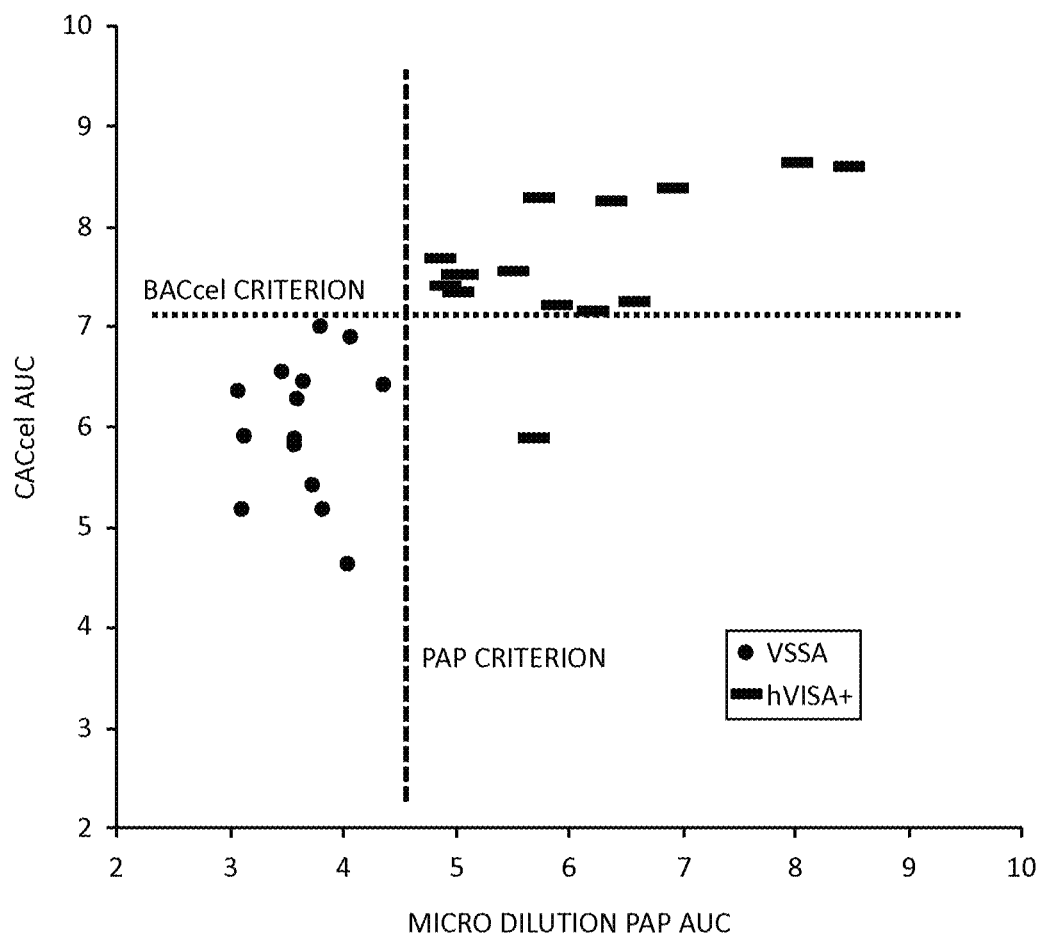
FIG. 15 illustrates a scatter plot of multiplexed automated digital microscopy (MADM) system-determined Area Under the Curve (AUC) for abbreviated population analysis profiles (PAP) vs. broth microdilution BMD-PAP-AUC (arbitrary units for areas).
Figures 16A, 16B, 16C, 16D, 16E:
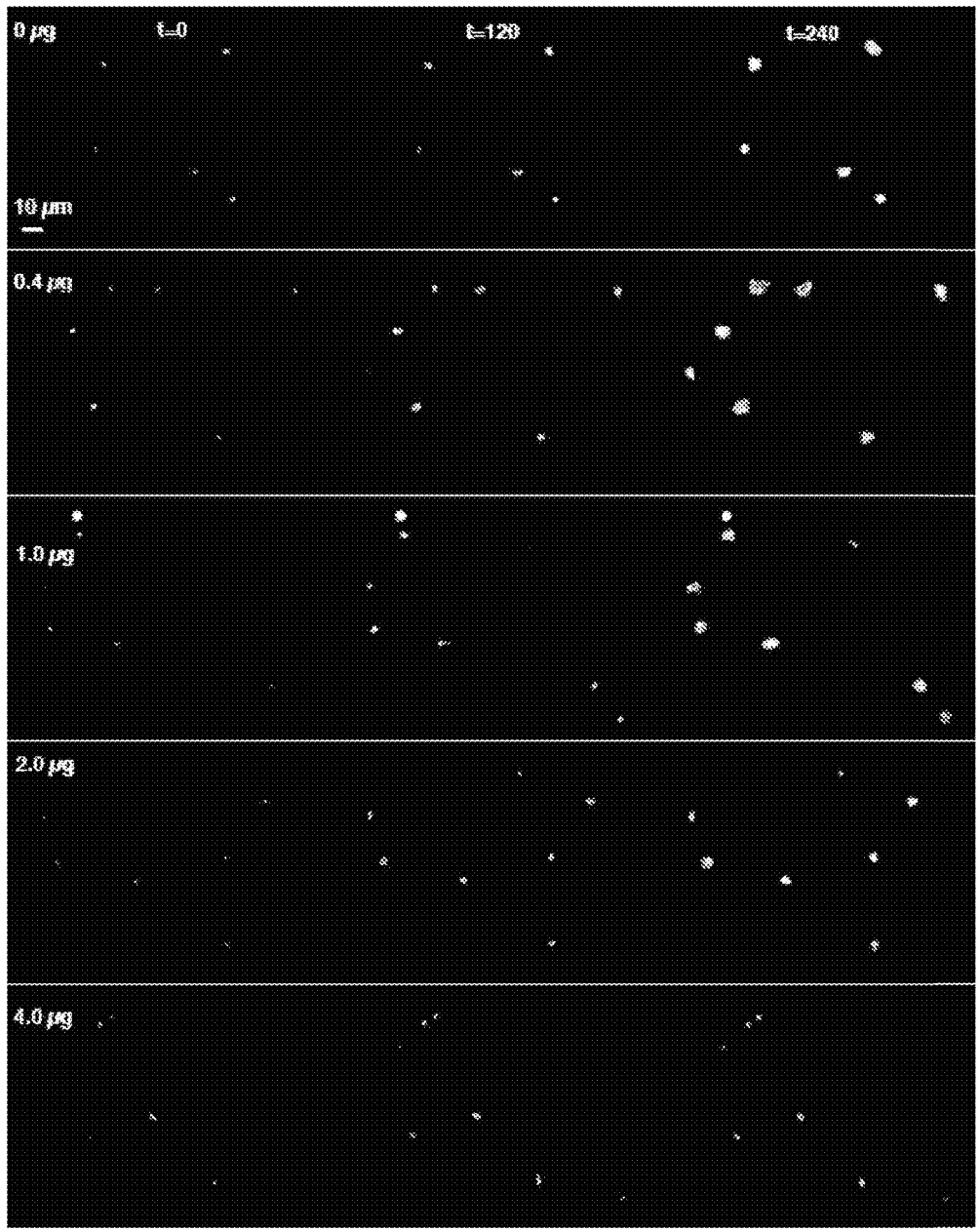
FIGS. 16A-16E illustrate heterorisistant vancomycin-intermediate *Staphylococcus aureus* (hVISA) strain 2-9B, images at 0, 120, and 240 minutes (horizontal labels and columns) in different vancomycin (VAN) concentrations (μg/mL, rows).

BMD-PAP detected 15 hVISA+ isolates (3 CDC strains, 12 screened clinical isolates) and 15 VSSA (12 CDC strains). One MADM system evaluation with a VSSA strain contained too many organisms to count and was censored as a technical error, leaving 29 total comparisons. The MADM system correctly classified 14/15 hVISA+ strains, and 14/14 VSSA strains. As illustrated in the plot of MADM-PAP-AUC vs. BMD-PAP-AUC (FIG. 15, arbitrary units for areas), one discrepant hVISA+ strain exhibited a MADM system AUC value below the classification criterion. Horizontal dotted line shows the MADM system criterion AUC level, and vertical dotted line shows BMD-PAP AUC detection criterion. Test sensitivity was 93% (CI95 66%-100%) and specificity was 100% (CI95 73%-100%). The MADM system time-to-result was 4 hours.

Zoomed images (FIGS. 16A-16E) illustrate an example for one hVISA+ strain at several VAN concentrations used to derive the abbreviated MADM system PAP. Increase in individual clone mass appears as a brightening of, and increase, in the clone's 2-dimensional footprint area. Integrated pixel intensity enables computation of growth rates over time using a series of time lapse images acquired at 10-minute intervals. A count of 4-hours clones that exhibit at least 4-fold growth, divided by the initial count of growing clones in the same fields of view, yielded normalized PAPs.

Discussion

Growth analysis by the MADM system revealed an identification criterion for using abbreviated PAPs of individual clones growing in the presence of different VAN concentrations to identify non-susceptible *S. aureus* subpopulations in isolates obtained from various sources. The comparator method used an analogous PAP with broth cultures and the generally accepted classification criterion against a stable reference strain (Mu3).

MADM system PAPs for positive strains had down-sloping characteristics of heteroresistance as did the BMD-PAPs. This study identified a narrow range of VAN concentrations to use for expanded studies, enabling efficient and rapid automation. At its present state, the MADM system appears applicable for use with clinical isolates to identify hVISA+ within 4 hours. This enables replication with larger screening studies to help estimate phenotype prevalence as well as characterizing statistical performance.

The small number of cells required is also compatible with the number available from lower respiratory tract specimens at the diagnostic threshold. Additional research with polymicrobial specimens will determine potential for inclusion in a practical rapid diagnostic system.

Conclusion

A multiplexed automated digital microscopy (MADM) system in accordance with various embodiments of the present disclosure identified hVISA+ isolates in 4 hours with 93% sensitivity and 100% specificity in a collection of 29 isolates characterized by a broth microdilution methods for population analysis profiling.

Example 6

Rapid Microbiological Identification and Major Drug Resistance Phenotyping Using a Multiplexed Automated Digital Microscopy (MADM) System for Ventilator-Associated Pneumonia (VAP) Surveillance Introduction Standard clinical VAP diagnosis is imprecise, with subsequent treatment often delayed and associated with increased morbidity, mortality (28-d MR=30%) and hospital costs. Quantitative culture (qCx) of bronchoalveolar lavage (BAL) is usually obtained only after VAP is clinically diagnosed. Surveillance of at-risk mechanically ventilated (MV) adults with multiple BALs is associated with significantly more antibiotic-free days & fewer deaths. However, surveillance qCx requires 48-72 hours for results from conventional labs. Susceptibility testing requires an additional day.

Surveillance microbiological testing for rapid bacterial identification and antibiotic resistance testing was evaluated using a multiplexed automated digital microscopy (MADM) system in accordance with various embodiments of the present disclosure to assess whether it could sensitively identify patients who subsequently develop VAP when compared to usual microbiological approaches using conventional culture methods of lower respiratory samples from patients at risk for VAP and reduce time to initiation of treatment and reduce failure rates of initial therapy.

Materials and Methods

Adult MICU patients with identified surrogate were included within 72 hours of intubation and if anticipated to require MV for >48 h. Moribund state or pregnancy were exclusions. Surveillance mini-BAL (Combicath, Plastimed) was performed on Day 1, 3, 5, 7 and 10 of MV. Samples were split and processed for both a) routine respiratory quantitative microbiological culture and sensitivity assays (>48 h result availability) and b) rapid (<8 hour) flowcell/surface-capture assays using the MADM system. Viable microorganisms were identified using growth analysis enhanced by a focused VAP antibody panel (S. aureus, P. aeruginosa, A. baumannii). Untypable organisms were also reported. Sensitivity was assessed using growth analysis. Attending physicians were blinded to MADM system results.

BAL sample were prepared, removing debris and separating microorganisms from other sample material. Sample microorganisms were introduced into a multichannel fluidic cassette as described elsewhere herein. Bacteria were concentrated and retained on the lower surface of all flowcells using low-voltage electrical field (5 min). Antibody labeling of bacteria in flowcells was used to aid identification.

The automated digital microscopy system was used to perform darkfield imaging of 10 fields of view every 10 minutes for 180 minutes in each flowcell channel. Initial epifluorescence imaging was also performed for antibody detection. The system used identification algorithms in accordance with various embodiments of the present disclosure for each individual immobilized microorganism exhibiting growth and determined growth rates of progeny for the duration of the test. Identification consisted of probability scores based on microorganism morphology and growth rates. Antibody labeling identification data was also incorporated. Observed microorganisms were then classified as STAU, PSAE, or non-target. Antibiotic responses were used to aid identification when appropriate. Quantitation was performed by counting identified microorganisms and computing original specimen CFU/mL.

Conventional clinical microorganism identification was performed by DHMC micro lab using standard CLSI procedures. Clinical microbiological data was provided to ICU clinicians for medical decision making. Identification information generated using the MADM system was prospectively performed but not available for clinical decision making.

TABLE 6

| Species | Resistance Mechanism |
|---|---|
| S. aureus (STAU) | MRSA phenotype |
|  | Clindamycin resistance (any) |
| P. aeruginosa (PSAE) | Amikacin resistance |
|  | Piperacillin/Tazobactam resistance |
| A. baumannii (ABCC) | Imipenem resistance |
|  | Cefepime resistance |

VAP target organization panel for identification & susceptibility >$10^4$ CFU/ml Primary outcome assumptions were made relative to study power and sample size: 1) 10% incidence of VAP, 2) 40 h difference in clinically reportable VAP target (QCx BAL ID (48 h)+resistance (18 h) vs. MADM system determination of BAL ID (4 h)+resistance (2 h)), and 3) 80% power, two-tailed $\alpha \leq 0.01$ requires 35 patients, assuming a median of 2 mini-BAL per patient (~8 unique isolates).

Results

Figure 17A:
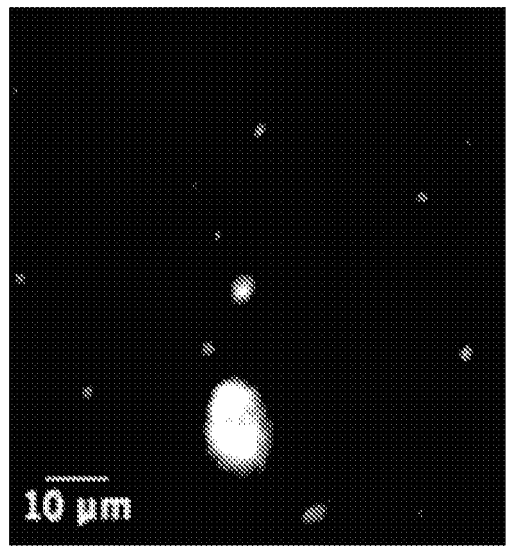
FIGS. 17A-17B illustrate computer-imposed colored ellipses indicate potential organisms (pixel blobs) tracked for growth during analysis in accordance with various embodiments.
Figure 17B:
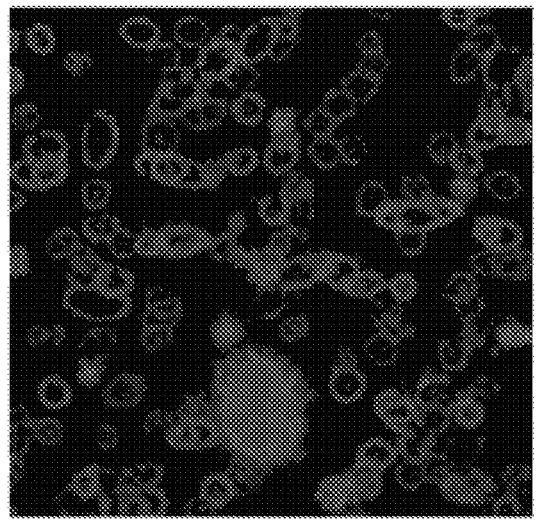

A total of 77 mini-BALs (median 2; range 1-7 per patient) were performed on 33 MV patients. Patient demographics are presented in Table 7. 20 (61%) patients had diffuse or patchy chest x-ray infiltrates and 3 patients had no infiltrates on enrollment. 70 BAL samples were tested using a MADM system. FIGS. 17A and 17B illustrate computer-imposed ellipses indicating potential microorganisms (pixel blobs) tracked for growth during analysis. 12 samples grew ≥1 bacterial type at >104 CFU/mL by qCx. 8 samples contained mixed respiratory bacteria. 7 samples contained VAP associated bacteria (4 S. aureus (including 1 auxotroph and 3 MRSA), 2 S. maltophilia, 1 K. pneumoniae). The MADM system identified 3 of 4 target organisms accurately and antimicrobial response enabled identification of 2 of 2 S. maltophilia. A K. pneumoniae sample was reported untypable. Auxtrophic growth precluded testing for 1 *S. aureus* sample. Antimicrobial response matched in 5 samples (3 MRSA, 2 *S. maltophilia*). 14 samples grew ≥1 bacterial type at <104 CFU/mL by QCx. 10 samples contained mixed respiratory bacteria, 3 samples yeast, 2 samples lactose fermenting GNB, 1 sample non lactose fermenting GNB, 1 sample *H. influenzae*, beta lactamase positive, 1 sample H. species, not influenzae, 1 sample beta hemolytic *Streptococcus*. None of the patients having bacteria detected by QCx at <104 CFU/mL developed clinical VAP. In 98% of samples, MADM system determined results were concordant with QCx-negative samples. The MADM system detected an enteric organism ($10^5$) in one sample negative by QCx. One VAP was diagnosed by clinical criteria. MADM system determined identification would have resulted in important and earlier antibiotic change/addition in 63% of mini-BAL samples with above threshold target organisms by QCx.

TABLE 7

Patient demographics (n = 34)

| | | | |
|---|---|---|---|
| Age; Median (IQR) | | 55 | (41-60) |
| Gender | | 21M: 13F | |
| Ethnicity | Hispanic | 14 | (42%) |
| | Native American | 1 | (3%) |
| | Caucasian | 14 | (42%) |
| | African American | 4 | (12%) |
| Smoking | Ever | 27 | (82%) |
| | Current | 17 | (52%) |
| Alcohol Use AUDIT Score | Median (IQR) | 7 | (0-18) |
| APACHE II | Median (IQR) | 21 | (16-24) |

TABLE 7-continued

Patient demographics (n = 34)

| | | | |
|---|---|---|---|
| Mech. Vent (days) | Median (IQR) | 4 | (6-10) |
| ICU LOS (days) | Median (IQR) | 10.5 | (6.5-18.2) |
| ICU D/C Status | Deceased | 11 | (33%) |
| | Home | 18 | (55%) |
| | SNF | 3 | (9%) |
| | T/F - acute hospital | 1 | (3%) |

TABLE 8

BAL surveillance and safety

| | |
|---|---|
| Patients enrolled | 34 |
| Surveillance mini-BAL performed | 77 |
| Combicath (Plastimed) | 66 |
| AirLife ™ Catheter (Carefusion) | 11 |
| BAL per patient; Median (IQR, range) | 2 (1-4, 1-7) |
| BAL return; Average (SEM) | 5.2 ± 0.5 mL |

Surveillance BAL Adverse Events Total (BALs = 77)

| | n | % |
|---|---|---|
| Desaturation requiring increase Fi02 | 2 | 3% |
| Tachycardia | 1 | 1% |
| Agitation post mini BAL (60 min) | 2 | 3% |
| Bloody return | 4 | 5% |
| Total | 9 | 12% |

TABLE 9

Microbial ID; clinical correlations

| | | MADM Micro ID 4-6 Hurs (BACcel ™) | | | Conventional Micro ID 48-72 hours | | Abx at time of | |
|---|---|---|---|---|---|---|---|---|
| pec# | PIS | BACcel ID | Conc (CFU/ml) | Phenotype, sensitivity | Isolate | Concordance | mini-BAL | DC Status |
| 03-D1 | | Fastidious Organism | $1.07 \times 10^4$ | Phenotype not assessed | $10^4$-$10^5$ MSSA | No | None | SNF |
| 05-D7 | | Enteric | $1.26 \times 10^5$ | AN, IMP-no growth, CAZ, CLI, FOX, TZP-all growth | No isolate | no | CTX D5 not on day | Died |
| 06-D1 | | Steno | $7.68 \times 10^5$ | AN, CAZ, CLI, FOX, IMP-all growth, TZP-antimicrobial effect | >$10^5$ *S. maltophilia* | yes | Vanco/Icaspo/imipenem | Home |
| 06-D3 | | Steno | $1.60 \times 10^4$ | AN, CAZ, CLI, FOX, IMP-all growth, TZP-antimicrobial effect | $10^4$-$10^5$ *S. maltophilia* | yes | TMP/Levaquin/Casp/Vanco | Home |
| 08-D7 | | STAU | $1.11 \times 10^6$ | FOX-R (MRSA) CLI-R | >$10^5$ MRSA | yes | Metronidazole only | Died |
| 08-D10 | | STAU | $1.42 \times 10^5$ | Technical failure, no phenotype | $10^4$-$10^5$ MRSA | yes | Metronidazole only | Died |
| 17-D1 | | UNK/enteric | $1.87 \times 10^4$ | ID UNK, no phenotype available | $10^4$-$10^5$ *K. pneumo* | yes | Vanco, HIV | SNF |
| 22-D3 | | STAU | $4.00 \times 10^4$ | MRSA | $10^4$-$10^5$ MRSA | yes | Vanco; (zosyn DC d2) | Home |
| 33-D7 | | STAU | $6.64 \times 10^4$ | MRSA, CLI-R | $10^4$-$10^5$ *Candida* spp. | no | Cefepime, Vanco flouc; | Home |

TABLE 10

Microbiology performance

| Performance Characteristic | Rate | Comments |
|---|---|---|
| BAL Samples with Target organism micro ID | 12 (15.6%) | 9 patients |
| Concordance Conventional vs. CPIS ≥6 | 7 of 8 | |
| Concordance BACcel vs. CPIS ≥6 | 8 of 9 | |
| BACcel call prior to routine change care | 9 of 9 | Change of Abx in 6; Abx stopped in 2 |
| VAP diagnosis by CDC NIS criteria | 1 | Enteric organism* |

*Organism not specified. BACcel positive on D7. No antibiotic for 2 days at time of miniBAL; patient died.

TABLE 11

Study results

| | | Clin Micro Presence/Absence ≥1 × $10^4$ CFU/mL | | STAU, PSAE, ABCC, Steno, Enteric |
|---|---|---|---|---|
| | | Positive | Negative | |
| BACcel MADM | Positive | True Positive (N = 6) | False Positive (N = 2*+) | Positive Predictive value 75% (6/8) |
| | Negative | False Negative (N = 1+) | True Negative (N = 61) | Negative predictive value 98% (61/62) |
| | | Sensitivity = 86% (6/7) | Specificity = 97% (61/63) | |

*Patient with diffuse infiltrates + clinical pneumonia CPIS score (≥6)
+BACcel isolate: Gr + ve clustered cocci. Speciation pending S. auerus vs. CNS +STAU grew in fastidious growth media flow cell but STAU ID test was not activated in that flow cell. STAU was called correctly after activation
POSITIVE diagnostic likelihood ratio (+DLR) = 27:95% CI [6.7-109]
NEGATIVE diagnostic likelihood ratio (−DLR) = 0.15:95% CI [0.02-0.91]

Conclusions

Mini-BAL based surveillance for VAP is both feasible and safe in ventilated at-risk patients. MADM system-based microbiological surveillance for VAP demonstrated sensitivity (86%) and specificity (97%), with a significant reduction in time to clinically available bacterial ID and resistance (approximately 40-66 h lead time) for multiple organisms and resistance types. In 5 of 7 (63%) mini-BAL samples with a target organism above threshold by QCx, MADM system-based ID would have resulted in important and earlier antibiotic changes/additions. As shown here, systems in accordance with various embodiments of the present disclosure, such as the MADM system, is a promising approach for rapid surveillance in patients at risk for VAP.

Example 7

Rapid Identification of Resistance Phenotypes in Gram-Negative Bacilli Using an Automated Digital Microscopy System Introduction Nosocomial infections due to multi-resistant Gram negative bacteria are increasing in frequency and growing in complexity. Pseudomonas aeruginosa (PA) and Acinetobacter baumannii (AB) are major causes of nosocomial infection and difficult to manage because of multi-drug resistance. Enterobacteriaceae that acquire the KPC carbapenemase are also likely to co-exist with multi-drug resistance in addition to presenting formidable detection challenges. Conventional phenotyping methods require growth of large numbers of bacteria, which increases the total time-to-result. For critically ill patients, the likelihood for success is indirectly related to the time required to administer effective antimicrobial therapy. However, standard tests require 2-3 days to characterize antimicrobial resistance patterns using culture-based methods. In contrast, various systems and methods in accordance with various aspects of the present disclosure, such as multiplexed automated digital microscopy (MADM) systems, have the potential to reduce turnaround time by direct detection of antimicrobial resistance phenotypes in bacteria extracted from a clinical specimen. The purpose of this study was to determine the sensitivity, specificity, and speed of automated microscopy to detect major resistance phenotypes associated with multi-drug resistance in significant Gram-negative clinical isolates.

Materials and Methods

We adapted a commercial inverted microscope and camera with custom image analysis software and a purpose-built 32-channel disposable fluidic cassette (FIG. 4A). Cassette flowcells (FIG. 4B) had transparent top and bottom surfaces to allow microscope imaging. The bottom surface was coated with poly-L-lysine to immobilize live bacteria.

We tested clinical isolates of Pseudomonas aeruginosa (PA), Acinetobacter baumannii (AB), and Klebsiella pneumoniae (KP). Test agents included amikacin (AN), imipenem (IMP), ceftazidime (CAZ), ertapenem (ETP), aminophenylboronic acid (APB), and benzo(b)thiophene-2-boronic acid (BTB). The boronic acids inhibit the KPC enzyme as well as AmpC. Table 12 summarizes organisms and test conditions. Test results are expressed as nonsusceptible (NS) or susceptible (S).

TABLE 12

Organisms and test conditions

| Species | Test | # NS/S | Conditions |
|---|---|---|---|
| PA | AN | 37/35 | AN 32 µg/mL |
| AB | IMP | 26/66 | IMP 8 µg/mL |
| | CAZ | 59/17 | CAZ 8 µg/mL |
| KP | ETP | 6/13 | ETP 16 µg/mL |
| | KPC/APB | | ETP 16 µg/mL + APB 300 µg/mL |
| | KPC/BTB | | ETP 16 µg/mL + BTB 50 µg/mL |

We grew isolates on blood agar, suspended colonies in tryptic soy broth for 2 hours, then centrifuged and resuspended log-phase bacteria in low ionic strength electrokinetic buffer.

MADM system analysis was performed using a 32-channel disposable fluidic cassette (FIG. 4A) to measure growth of immobilized bacteria. We separately tested PA clinical isolates for nonsusceptibility (NS) with amikacin (AN) at 32 µg/mL, and AB isolates with imipenem (IMP) at 8 µg/mL or ceftazidime (CAZ) at 8 µg/mL. We tested Klebsiella pneumoniae (KP) clinical isolates for ertapenem (ETP) nonsusceptibility at 16 µg/mL with and without the inhibitors aminophenyl boronic acid (APB) at 300 µg/mL or benzo(b)thiophene-2-boronic acid (BTB) at 50 µg/mL to identify putative KPC-positive strains.

10 µL aliquots of 5E+7 CFU/mL were pipetted into separate flowcells for each isolate and test condition. Microorganisms were electrokinetically concentrated onto the flowcell detection surface with an electrical field to the positively charged lower surface to immobilize cells and yield 10-100 bacteria per field of view (FIG. 4B). Each isolate was tested in separate flowcell channels with no antibiotic (growth controls). The system measured growth at 10-minute intervals. Microorganisms were exposed to the test conditions for 3 hours. Growth was evaluated, interpreting results for PA, AB, and KP-ETP as NS if growth had not arrested within 3 hours. Results for both KP-KPC tests were interpreted as presumptive for KPC if growth differences between the inhibited (with APB or BTB) and uninhibited (ETP alone) exceeded a criterion amount (FIG. 20) in the same 3 hour time frame. CLSI disk diffusion assays were performed as controls for PA and AB; and a CLSI Hodge Test and RT-PCR were performed as controls for KP.

Results

Table 13 summarizes assay performance. Sensitivity and specificity were, respectively: PA-AN (33/37) 89% and (33/35) 94%; AB-IMP (24/26) 92% and (65/66) 98%; AAB-CAZ (58/59) 98% and (14/17) 82%; KPETP (6/6) 100% and (13/13) 100%; KPC/APB (5/6) 83% and (13/13) 100%; KPC/BTB (4/6) 67% and (13/13) 100%.

TABLE 13

Assay performance

| Test | Sensitivity | Specificity |
| --- | --- | --- |
| PA-AN | 33/37 89% CI 74%-96% | 33/35 94% CI 79%-99% |
| AB-IMP | 24/26 92% CI 73%-99% | 5/66 98% CI 91%-100% |
| AB-CAZ | 58/59 98% CI 90%-100% | 14/17 82% CI 56%-95% |
| KP-ETP | 6/6 100% CI 52%-100% | 13/13 100% CI 72%-100% |
| KP-KPC/APB | 5/6 83% CI 36%-99% | 13/13 100% CI 72%-100% |
| KP-KPC/BTB | 4/6 67% CI 24%-94% | 13/13 100% CI 72%-100% |

Figures 18A, 18B:
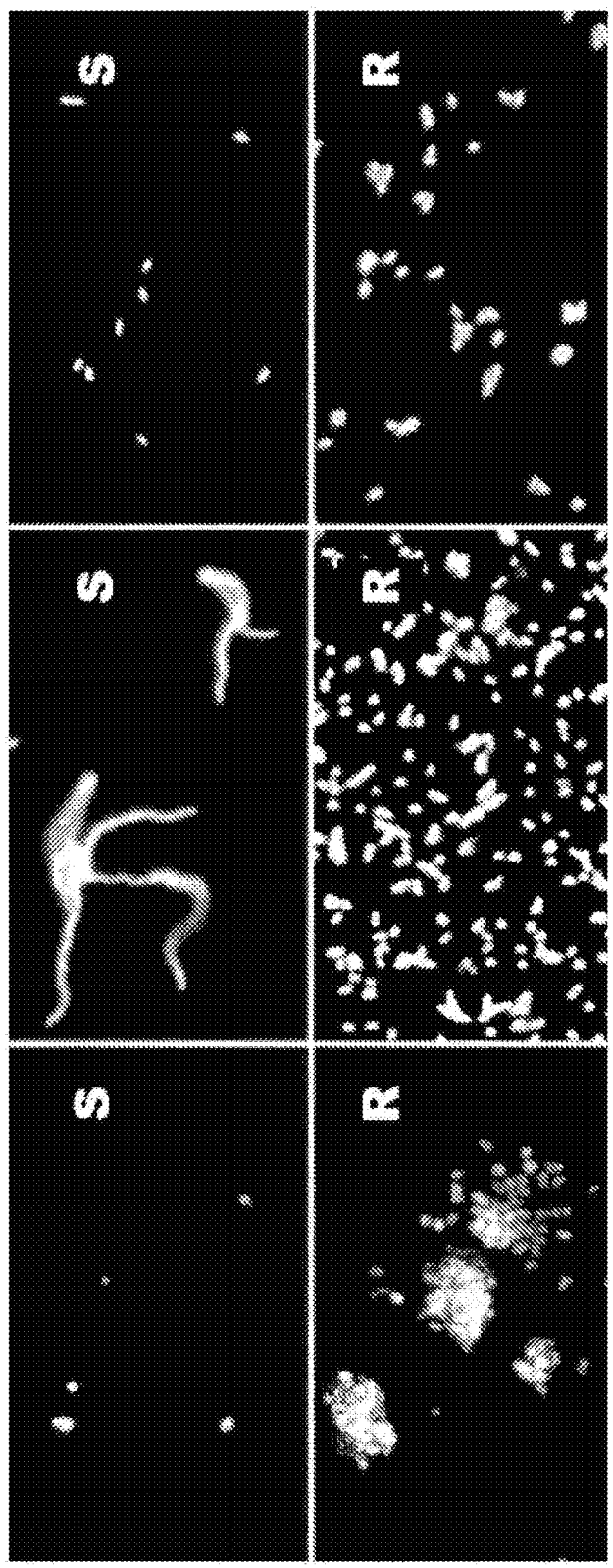
FIGS. 18A-18B illustrate non-fermenter clinical isolates at end of 3 hours of drug exposure in accordance with various embodiments.

FIGS. 18A-18B illustrate images of non-fermenter clinical isolates exposed to antibiotics for 3 hours. Images zoomed in for detail. Sum of integrated pixel intensities of individual clones closely parallels clone mass and/or cell count from standard methods. Either susceptible (FIG. 18A, S) or resistant (FIG. 18B, R) strains may show abnormal morphology during growth in drug-containing media. The detectable difference occurs when a susceptible strain ceases to grow.

Figures 19A, 19B:
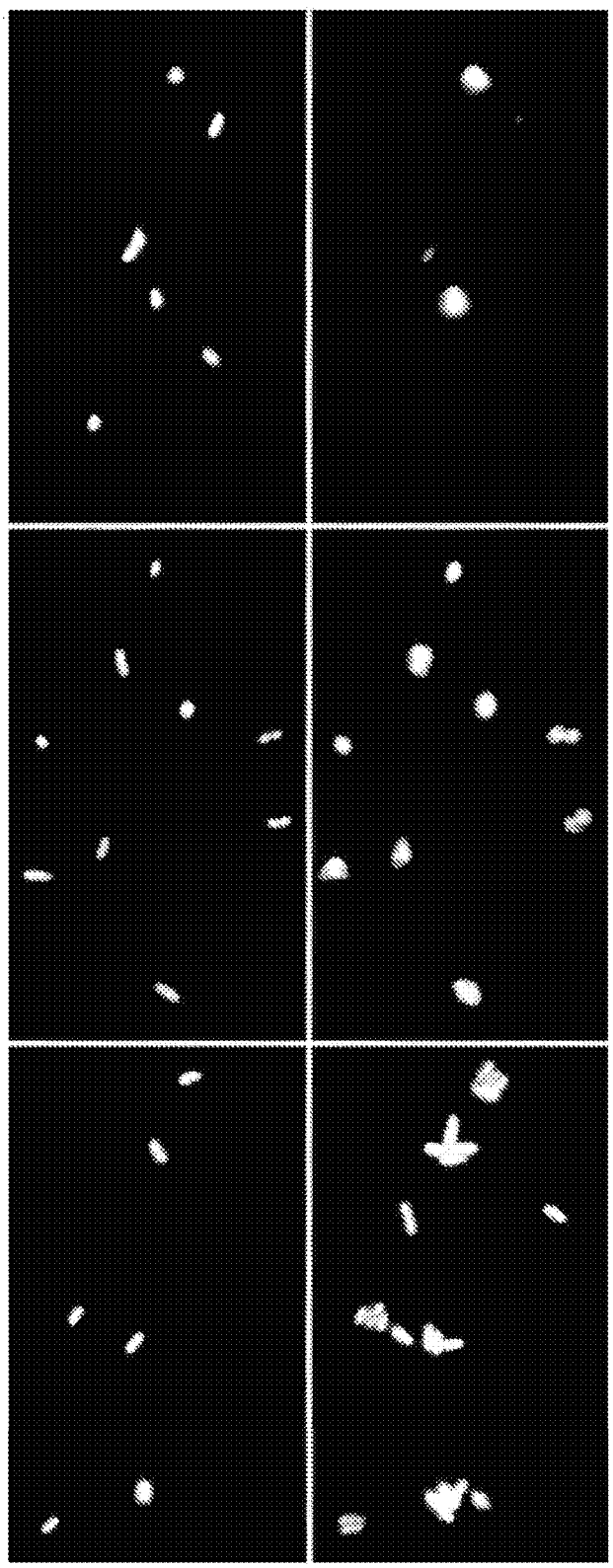
FIGS. 19A-19B illustrate a carbapenemase-producing *K. pneumoniae* (KPC) clinical isolate growth under various conditions.
Figure 20:
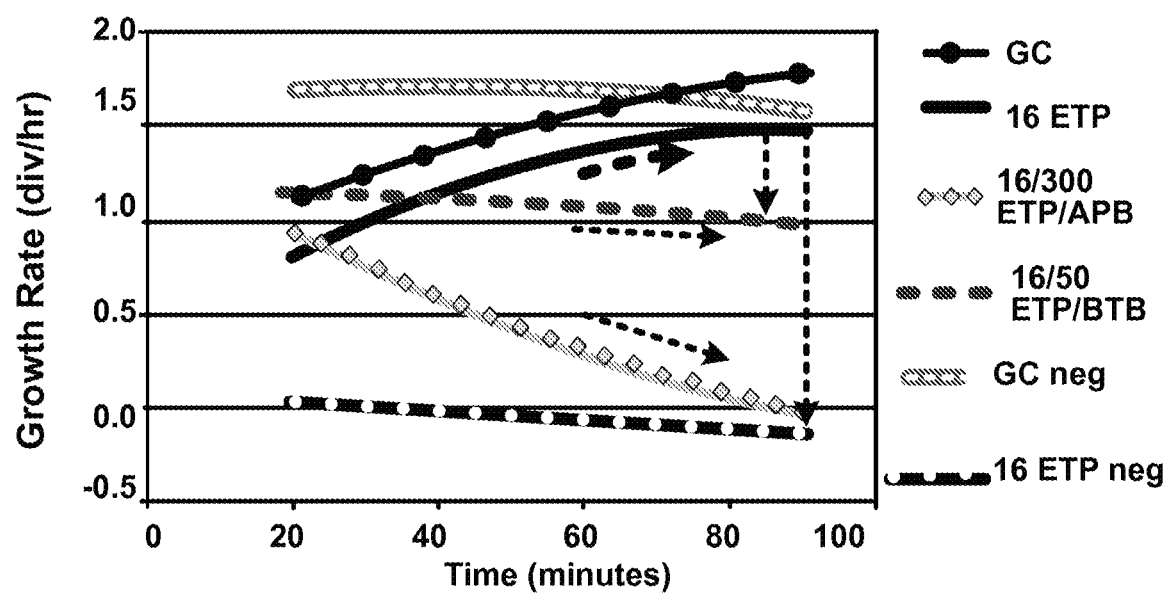
FIG. 20 illustrates KPC assays under various conditions.

FIGS. 19A and 19B illustrate images and growth data (FIG. 20) from KP tests. The left panel of FIGS. 19A and 19B illustrate 20 min after start of drug exposure. The right panel of FIGS. 19A and 19B illustrate 90 min after start of drug exposure. Images are zoomed for detail. ETP exposure causes abnormal growth morphology. Sum of integrated pixel intensities of individual clones closely parallels clone mass and/or cell count. Difference between ETP alone (FIG. 19A) and ETP+APB (FIG. 19B) shows enzyme inhibition and decreased resistance, hence KPC-positive interpretation. Clear differences occur between the behaviors in ETP alone and ETP with an enzyme inhibitor added (FIG. 20). Images show the same field of view at different times (20 and 90 minutes of drug exposure).

FIG. 20 illustrates KPC assays, growth rate vs. exposure time, "GC"=growth control, one for KPC-positive strain (same as in FIGS. 19A-19B) and one for KPC-negative strain (dotted line). For KPC-positive, the difference between growth curves for ETP alone and ETP with a boronic acid enzyme inhibitor (APB or BTB) determines the interpretation. Susceptible strains show no differences, and also fail to grow in ETP at 60 μg/mL (lower dotted line). The dashed arrows indicate growth curves that exceeded difference criteria (from the heavy dashed arrow) for a positive interpretation (enzyme positive ETP alone vs. ETP+inhibitor).

Conclusions

Direct analysis of small numbers of bacteria using ADM identified resistance phenotypes in non-fermenters and in *K. pneumoniae* within 3 hours. The experimental method met the objectives of using a small number of cells, achieving rapid results, and having accuracy approaching those of standard tests in identifying major resistance phenotypes, including difficult-to-detect KPC-positive organisms. Cell number was consistent with that previously shown adequate to rapidly identify pathogens from organisms extracted directly from a polymicrobial patient specimen. Further optimization may further decrease the total assay time and improve test performance.

Assay kinetics enabled sensitive, specific, and rapid detection of each phenotype using a single challenge concentration of each antibiotic.

Example 8

Rapid Identification of Live *Acinetobacter* Spp. in Bronchoalveolar Lavage Specimens by Automated Immunofluorescence Microscopy Introduction Hospital acquired infections (HAI), and particularly nosocomial pneumonia, are leading causes of morbidity and mortality in critically ill patients. *Acinetobacter* spp., including *A. baumannii* and several other *Acinetobacter genomospecies*, are important pathogens in the ICU.

Hospital-adapted *Acinetobacter* harbors numerous antibiotic resistance mechanisms and presents serious diagnostic challenges. Because these organisms are often highly drug resistant, their identity and phenotype markedly influence the choice of therapy.

Culture-based systems are able to identify *Acinetobacter* spp. but require initial enrichment culturing and colony isolation. Culturing methods therefore require as long as 48 hours for positive identification and antibiotic susceptibility testing. This is too long for managing critical infectious diseases because initial therapy must assure adequate control of disease progression.

Molecular methods shorten the identification, but cannot differentiate between live and dead, nor intact or fragmented bacteria, nor can they quantify specimen contents. These are important criteria for many types of specimen, particularly in diagnosing pneumonia.

In order to eliminate the delays required for culturing, it would be desirable to analyze live organisms extracted directly from a patient specimen. Such a method would require species identification and enumeration, as well as the ability to determine the viability of individual cells.

The purpose of this investigation was to characterize a method for rapid identification of *Acinetobacter* spp. extracted directly from a mock specimen using fluorescent-labeled antibody paired with automated growth tracking of individual bacteria to determine viability. The experimental methods tested in this study are intended to become part of a new rapid diagnostic system using bacteria extracted directly from a patient specimen without prior enrichment culturing or colony isolation.

Materials and Methods

*Acinetobacter* spp. and non-*Acinetobacter* isolates were obtained from ATCC and JMI Laboratories (N. Liberty, Iowa). The collection included 19 *A. baumannii* and 1 *Acinetobacter genomospecies*, plus 28 non-*Acinetobacter* isolates of species often found in respiratory specimens.

Direct observation of bacteria was performed on a disposable fluidic cassette inserted into a custom bench-top instrument that combines automated digital microscopy, motion control, and analysis module.

The cassette contained multiple independent flowcells. Flowcells were constructed with transparent top and bottom surfaces to allow microscope imaging. Each surface had a transparent electrode coating, forming an electrophoresis chamber. The bottom surface was coated with poly-L-lysine to immobilize bacteria upon surface contact.

Colonies from agar plates were resuspended in tryptic soy broth (TSB) and grown for 2 hours. Mock specimens were made by spiking log phase bacteria (approx. $5 \times 10^6$ CFU/mL) into bronchoalveolar lavage (BAL) fluid from non-infected sheep. A specimen was then centrifuged on Percoll to reduce debris, washed and resuspended in electrokinetic capture buffer, and pipetted into a cassette's sample wells. Tests were also performed on isolates without BAL. For experiments on live/dead mixtures, live organisms were mixed with formalin-killed bacteria in a 1:1 ratio (McFarland standard).

Figure 21A:
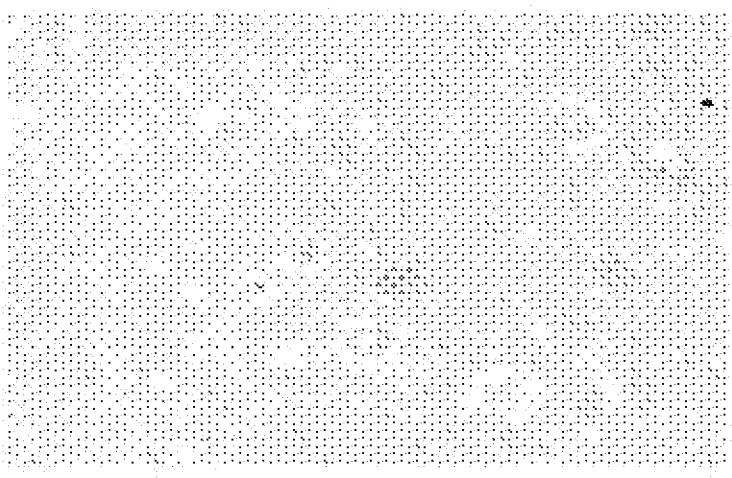
FIGS. 21A-21C illustrate (A) phase contrast, unfocused images show that bacteria are not in contact with the surface, (B) phase contrast, bacteria and residual debris in focus on the surface, and (C) a fluorescence image showing antibody-labeled bacteria.
Figure 21B:
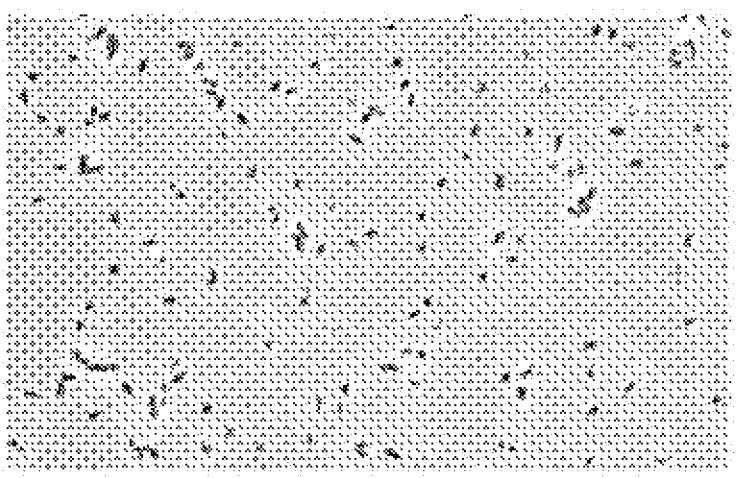
Figure 21C:
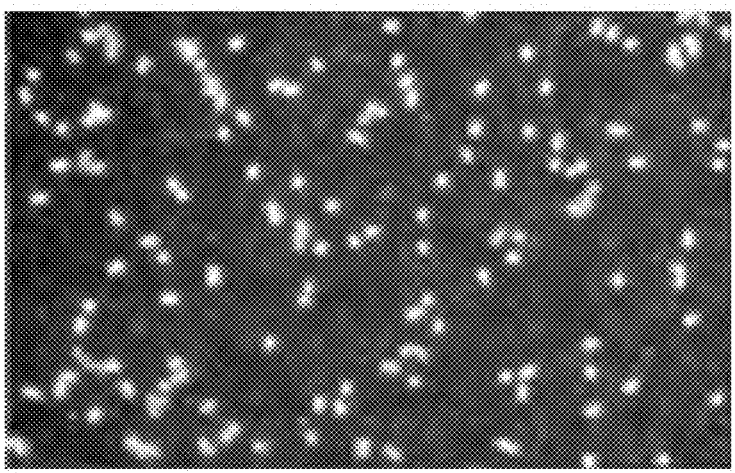

Application of an electrical field caused bacteria to migrate to the positively-charged lower electrode during a capture step. The bacteria adhered to the surface coating, permitting subsequent medium exchanges. Photomicrographs illustrating microorganisms in a flowcell before and after surface capture are shown in FIGS. 21A-21C. FIG. 21A illustrates unfocused images showing that bacteria are not in contact with the surface. FIG. 21B illustrates bacteria and residual debris in focus on the surface. FIG. 21C illustrates fluorescence image showing antibody-labeled bacteria. Each flowcell contained approximately 100 to 500 founder cells on the surface within the digital microscope's 444×592 μm field of view. After capture, the flowcells were rinsed with TSB, removing electrokinetic concentration buffer.

Polyclonal antibodies were developed in chickens and isolated using acid precipitation of yolk proteins followed by tangential flow filtration using a 100 kDa filter. Antibodies specific for *Acinetobacter* surface antigens were isolated from the yolk preparation by affinity purification.

Antibody staining of immobilized bacteria was performed by incubation in the affinity-purified IgY for 5 minutes in a 1% BSA/TSB staining solution. Primary antibody binding was followed by washing and detection of bound IgY using 5-minute incubation in goat anti-chicken antibody conjugated to Alexa-555. Quantitative image analysis computed the mean intensity of cell staining and the percentage of cells that stained above a threshold level criterion.

The instrument acquired time sequenced images for each of the flowcells at 10-minute intervals. For growth measurement, the image analyzer computed mass changes using dark field imaging mode. Clones were considered to be growing if they exhibited at least 50% increase in integrated intensity over the 40 minute growth period.

To test feasibility for polymicrobial multiplexing, 1:1 mixed species of live *Acinetobacter* and *Pseudomonas aeruginosa* were spiked into BAL. Staining for *P. aeruginosa* used rabbit O-typing antisera and goat antirabbit antibody conjugated to Alexa-488.

Results

Anti-*Acinetobacter* antibody labeled 16 of 20 strains of *Acinetobacter* spp. and did not label 25 of 28 strains of non-*Acinetobacter* species commonly found in respiratory specimens (Table 14).

TABLE 14

Antibody staining results.

| Species | Number Tested | Number Positive (%) | Number Negative (%) |
|---|---|---|---|
| A. baumannii | 19 | 15 (79) | 4 (21) |
| Acinetobacter gsp. 13 | 1 | 1 (100) | 0 (0) |
| Total | 20 | 16 (80) | 0 (0) |
| Pseudomonas aeruginosa | 7 | 0 (0) | 7 (100) |
| Stenotrophomonas maltophilia | 4 | 0 (0) | 4 (100) |
| Haemophilus influenzae | 1 | 0 (0) | 1 (100) |
| Klebsiella pneumnoniae | 4 | 1 (25) | 3 (75) |
| Escherichia coli | 3 | 0 (0) | 3 (100) |
| Enterobacter aerogenes | 1 | 0 (0) | 1 (100) |
| Enterobacter cloacae | 2 | 1 (50) | 1 (50) |
| Staphylococcus aureus | 1 | 0 (0) | 1 (100) |
| Staphylococcus epidermidis | 1 | 0 (0) | 1 (100) |
| Staphylococcus haemolyticus | 1 | 0 (0) | 1 (100) |
| Staphylococcus pneumoniae | 1 | 0 (0) | 1 (100) |
| Staphylococcus pyogenes | 1 | 0 (0) | 1 (100) |
| Staphylococcus salivarius | 1 | 0 (0) | 1 (100) |
| Total | 28 | 3 (11) | 25 (89) |

Capture time was fixed at 300 seconds. Electrokinetic transport moved all bacteria above the capture area to the surface, determined by focusing at different levels above the surface. Growth of immobilized bacteria began after TSB wash without an appreciable lag time (<10 min.).

Figure 22A:
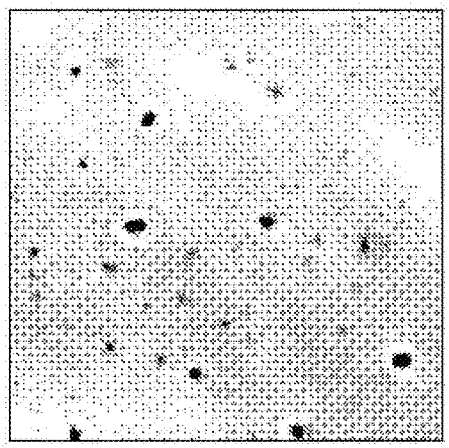
FIGS. 22A-22C illustrate live and formalin-killed *A. baumannii* (ATCC 19606).
Figure 22B:
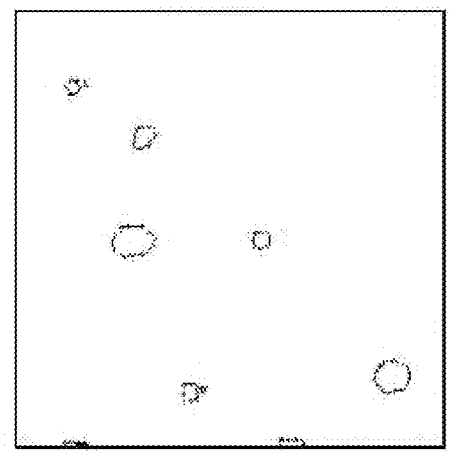
Figure 22C:
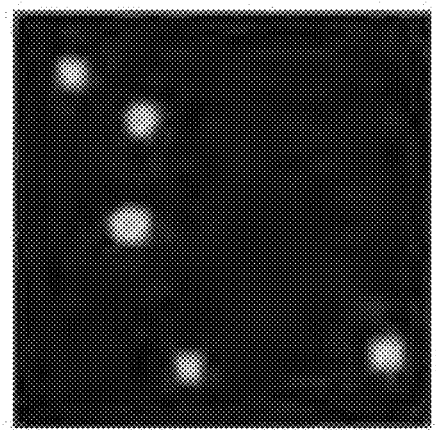

Antibody did not detectably bind to BAL debris. Over 90% of live cells extracted from the live control mock BAL specimen met the growth criterion, indicating that sample preparation capture, and labeling did not adversely affect viability. None of the spiked dead cells exhibited growth. A mixture of live and formalin-killed cells resulted in staining of both live and dead cells. FIGS. 22A-22C illustrate live and formalin-killed *A. baumannii* (ATCC 19606), partial field of view. FIG. 22A shows phase contrast, with debris. FIG. 22B illustrates outlines of image analyzer mapped contours of all presumptive cells. FIG. 22C illustrates fluorescence, antibody stained)

Figure 23A:
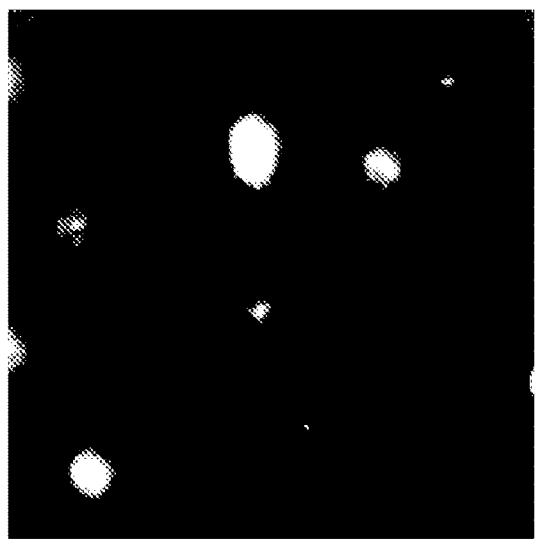
FIGS. 23A-23C illustrate growth of individual clones of ATCC 19606.
Figure 23B:
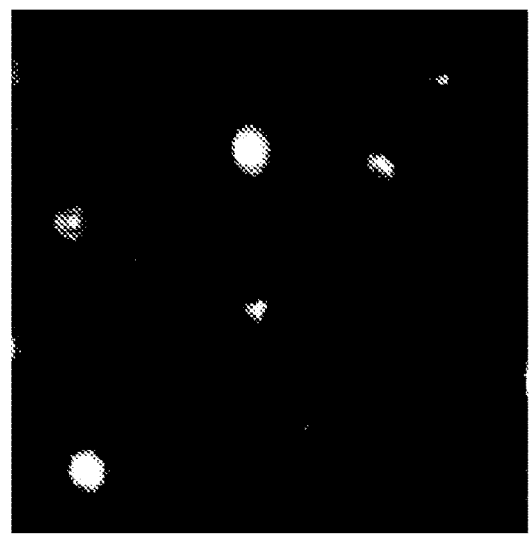
Figure 23C:
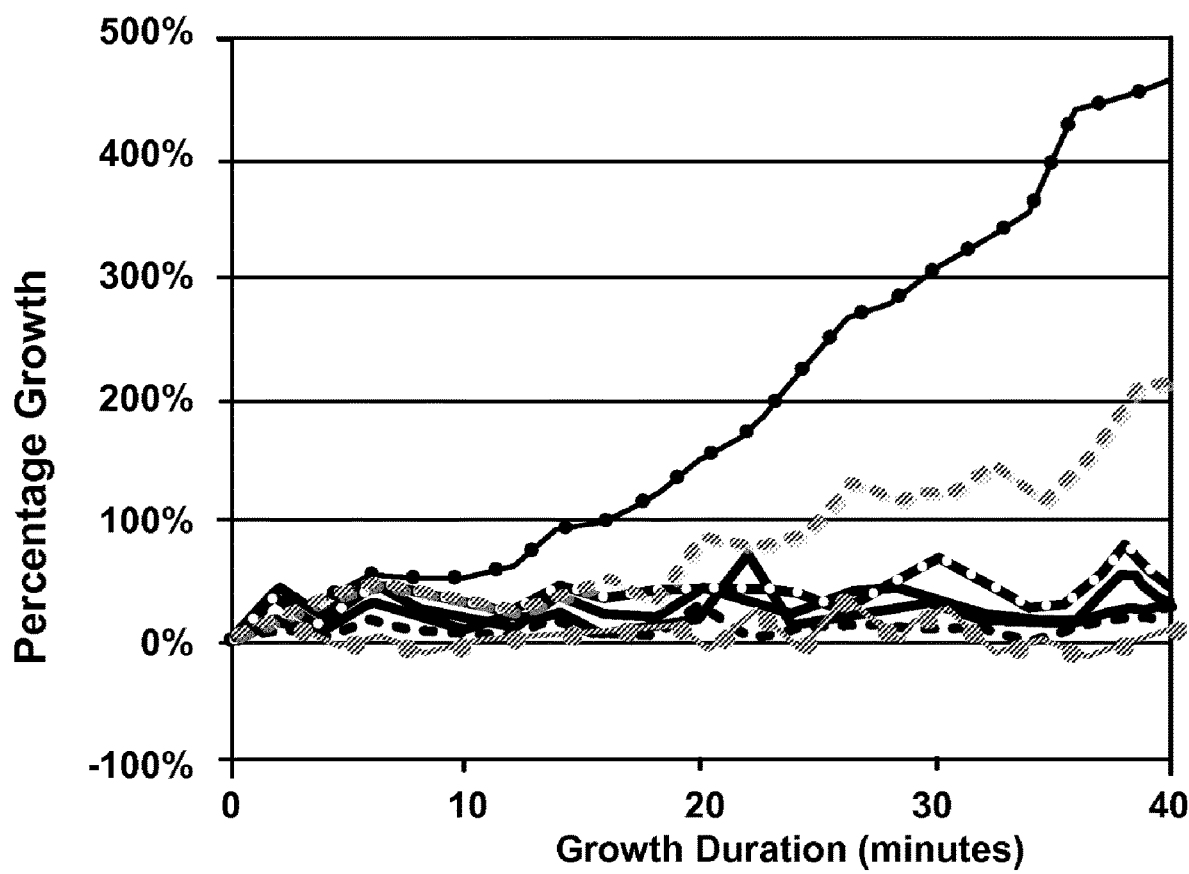

Growth measurement clearly differentiated between growing and non-growing individual clones after approximately 30 minutes of growth measurement. In the mixed live/dead mock specimen, 33% of clones met the viability criterion (FIG. 23A-23C illustrate examples of individual clones of ATCC 19606 *Acinetobacter*, live plus dead cells. Time sequence, dark field, partial field of view. FIG. 23A illustrates start of interval. FIG. 23B illustrates after 40 min. of growth. FIG. 23C illustrates quantitation of individual clone growth from the images).

Figure 24A:
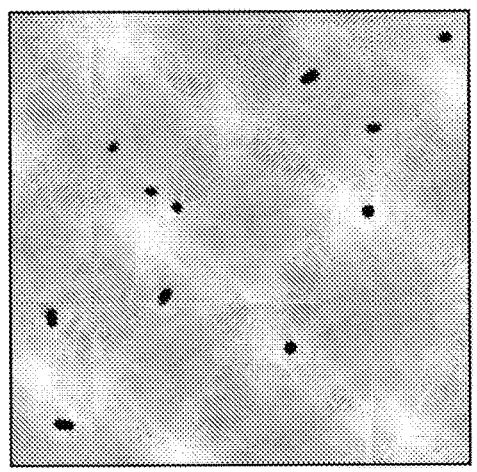
FIGS. 24A-24C illustrate mixed species, *A. baumannii* ATCC 19606 and *P. aeruginosa* ATCC 35554.
Figure 24B:
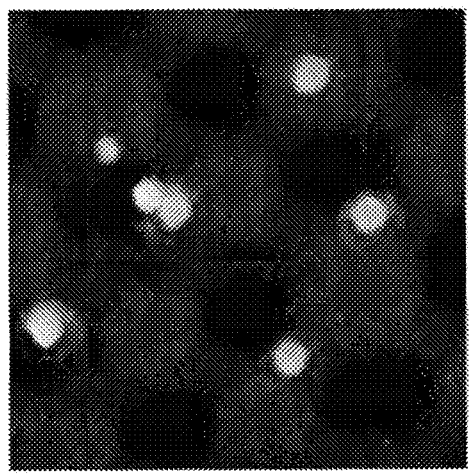
Figure 24C:
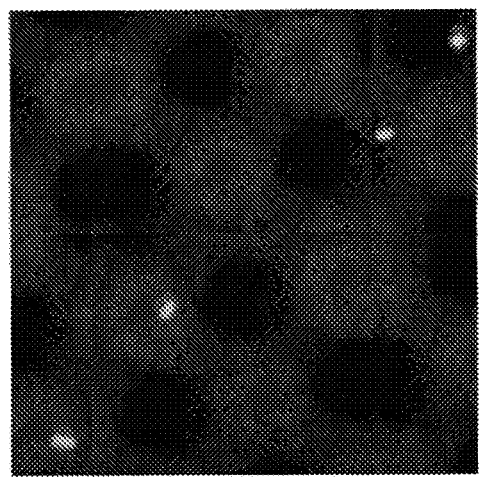

A mixture of live *Acinetobacter* and *Pseudomonas* exhibited the expected staining with respective antibodies. Of 344 total cells observed, 221 stained with *Acinetobacter* antibody and 123 stained with *P. aeruginosa* antibody. FIGS. 24A-24C illustrate a mixture of species, *A. baumannii* ATCC 19606 and *P. aeruginosa* ATCC 35554 (partial field of view). FIG. 24A illustrates phase contrast microscopy of the mixed species. FIG. 24B illustrates staining with anti-*Acinetobacter*. FIG. 24C illustrates staining with anti-*Pseudomonas*. None of the cells remained unstained, and none stained with both antibodies. Bacteria in control flowcells containing each strain alone were stained using their primary antibodies, and no cross-reactivity was observed for either one. Bacteria in separate control flowcells containing each strain alone did not stain with either secondary antibody in the absence of primary antibody.

This set of conditions demonstrated the feasibility of concurrent color multiplexing with multiple antibodies.

Conclusions

Polyclonal antibody developed against surface antigens of *Acinetobacter* spp. showed the potential for multiplexed identification in the presence of interfering species commonly seen in respiratory specimens. Electrokinetic immobilization and species immuno-identification did not significantly affect cell viability. The experimental methods were able to quantify the ratio of live cells in a mock specimen. Immuno-identification combined with automated growth tracking of immobilized bacteria represents a rapid and potentially powerful approach to identifying and differentiating intact live *Acinetobacter* spp. cells from dead or dormant cells directly from high-titer specimens.

Example 9

Direct Identification of MRSA and MLSB Phenotypes in *Staphylococcus aureus* Using Small Numbers of Immobilized Cells Introduction Mechanisms of broad-spectrum resistance to ß-lactam antibiotics present serious clinical challenges, particularly with critically ill patients. Methicillin resistant *S. aureus* (MRSA) has become a major pathogenic phenotype that requires rapid identification in order to assure adequate initial therapeutic coverage. MRSA is associated with multiple drug resistance mechanisms in addition to conferring total β-lactam resistance. Laboratories need new methods to rapidly determine all major antibiotic resistance phenotypes. Conventional phenotyping methods require growth of large numbers of bacteria, which lengthens the total time-to-result. New methods requiring small numbers of organisms for testing could potentially obviate the need for overnight culturing and enable direct-from-specimen analysis.

Multiplexed direct cellular phenotyping offers a rapid alternative method, requiring relatively small numbers of cells. It has the potential to overcome the inherent limitations of other rapid methods, such as gene-based detection, for which resistance expression lacks a direct molecular marker correlate. Direct cellular phenotyping shows evidence of meeting analytical challenges such as inducibility and heteroresistance that now complicate antibiotic susceptibility testing.

This study tested multiplexed assay methods intended to enable a new rapid diagnostic system that will use bacteria extracted directly from a patient specimen without prior enrichment or colony isolation. The purpose was to determine whether the novel direct cellular phenotyping methods meet requirements for speed and accuracy in simultaneously identifying two unrelated and clinically important resistance mechanisms in *S. aureus* using small numbers of bacterial cells.

Materials and Methods

Direct observation of bacterial response to antibiotic exposure was performed on a custom disposable 32-flowcell cassette (FIG. 4A) inserted into an automated digital microscope with customized motion control and image analysis software. Each flowcell (FIG. 4B) was independent. Flowcell top and bottom surfaces had transparent, electrically conductive coatings for electrophoresis and microscopy. The bottom surface was coated with poly-L-lysine that immobilized bacteria upon contact.

A collection of oxacillin borderline-MIC isolates was provided by the CDC. The collection included 78 mecA-positive and 56 mecA-negative strains, plus one strain with mutated mecA that produced a variant PBP2a protein of unknown clinical significance. Tests also included CLSI QC strains (data not shown), ATCC 43300 (MRSA), BAA-976 (macrolide efflux), BAA-977 (inducible MLSB phenotype), and 29213 (susceptible control). 44 of the mecA-positive and 14 of the mecA-negative isolates were either constitutively or inducibly resistant to clindamycin (CLI) according to D-test results. Table 1 lists the CLI resistance phenotype counts by mecA status.

TABLE 15

| CLI resistance phenotype counts by mecA status. | | | | | | | |
|---|---|---|---|---|---|---|---|
| mecA | $MLS_B$ Phenotype | | | | | | |
| Status | D | D+ | HD | R | NEG | S | Total |
| Positive | 24 | 3 | 8 | 9 | 12 | 23 | 79 |
| Negative | 10 | 2 | 1 | 1 | 3 | 39 | 56 |

Phenotypes as described by Steward et al. (2005):
D = D-test pos.
D+ = D-test pos. plus ingrowth;
HD = D-test pos. with haze overgrowth;
R = constitutively resistant to CLI;
NEG = susceptible to CLI;
S = susceptible to CLI and ERY.
All phenotypes except the S-type were ERY resistant.

Colonies from agar plates were resuspended in broth and grown for 2 hours. Log phase *S. aureus* were resuspended in electrokinetic capture buffer at $1 \times 10^6$ CFU/mL. A 10 μL sample was pipetted into each flowcell of the cassette, and the cassette placed into the instrument.

Electrophoresis for 5 minutes concentrated bacteria to the flowcell surface. Bacteria adhered to the capture coating, permitting subsequent medium exchanges. Each 444×592 μm field of view contained approximately 100-500 bacterial cells. All assays used Mueller-Hinton broth (MHB) as a wash medium and reagent vehicle.

For each isolate, the system performed concurrent assays in separate flowcells: a growth control, a non-induction FOX test, a FOX-induced FOX test, a non-induction CLI test, and an ERY-induced CLI test. Prior studies had established 1 h of 1 μg/mL FOX followed by 3 h of 6 μg/mL FOX as standard conditions. Other studies had established 1 h of 0.1 μg/mL ERY followed by 3 h of 0.5 μg/mL CLI as standard.

The instrument acquired images for each of the flowcells at 10-minute intervals. The system performed growth rate measurements on the entire bacterial population within each field of view.

Prior studies established growth-rate interpretation criteria after the challenge period. For MRSA identification, mecA-positive isolates had growth rates greater than 0.1 divisions per hour (div/h), and mecA-negative isolates had rates less than 0.1 div/h. For MLSB identification, CLI-resistant isolates had growth rates greater than 0.4 div/h and CLI-susceptible isolates had rates less than 0.4 div/h.

Results

Growth began after bacterial immobilization and MHB wash without an appreciable lag time (<10 min).

Figures 25A, 25B:
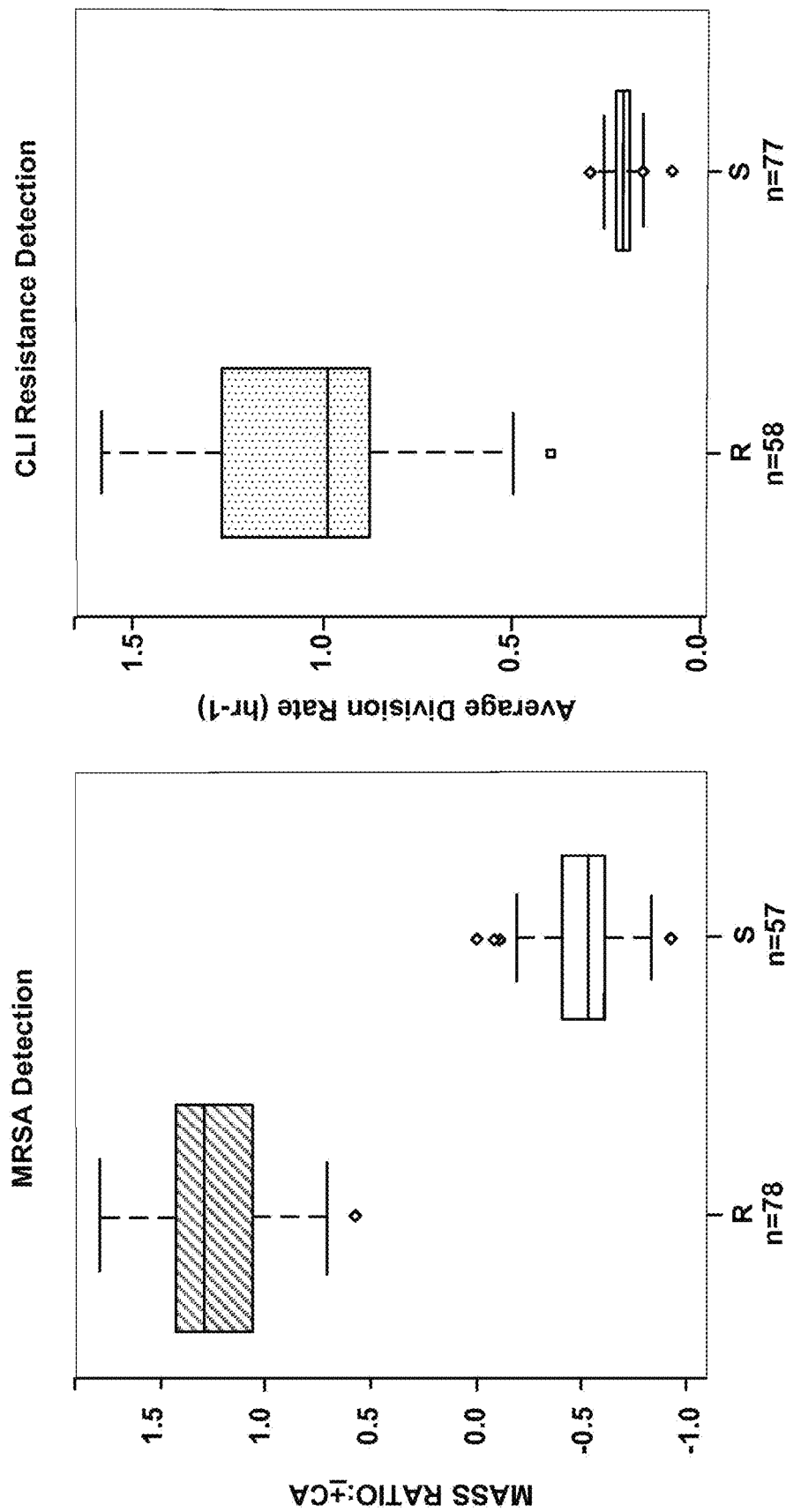
FIGS. 25A-25B illustrate MRSA identification using FOX induction (negative growth rate signifies cell lysis) and MLSB identification using erythromycin (ERY) induction and clindamycin (CLI) challenge.

78 of the 79 mecA-positive strains were classified as MRSA, and 56 of the 56 mecA-negative strains as MSSA (FIG. 25A). As with all test methods reported by the CDC (Swenson et al., 2007), the experimental method classified the mutated mecA strain (BS-089) as susceptible. MLSB identification using ERY induction and CLI challenge (FIG. 25B; note difference in Y-axis scale compared to FIG. 25A) This strain was classified MSSA in the tabulated results based on CLSI FOX-DD results. CLI-resistance was correctly characterized in 43 of the 44 mecA-positive and 14 of the 14 mecA-negative isolates (FIG. 25B). The division rate for the incorrectly classified strain is plotted separately as a striped square (FIG. 25A) and a spotted square (FIG. 25B). Results were compared to mecA PCR results, CLSI FOX disk diffusion (FOX-DD), and D-tests.

Discussion

The experimental method performed using a system and method in accordance with various embodiments of the present disclosure met the objectives of minimal starting cell count, rapid time to result, and demonstrated accuracy comparable to that of FOX-DD and D-zone tests in identifying the MRSA phenotype and CLI resistance in this oxacillin MIC borderline collection.

Further optimization of the induction concentration and challenge concentration may further decrease the total assay time using systems and methods disclosed herein.

Conclusions

Analysis using a MADM system in accordance with various embodiments of the present disclosure required orders of magnitude fewer cells (100-500) and a dramatically decreased period of time (4 hrs) for MRSA and MLSB identification as compared to the number of cells (approx. $10^4$-$10^5$) and length of time (days) required by conventional microbiological methods. If combined with compatible concentration and in situ identification methods, the rapid direct phenotyping method enabled the system and methods of the present disclosure has the potential to eliminate the need for overnight culturing and colony isolation with patient specimens such as bronchoalveolar lavage fluid, wound swabs, and other high-titer specimens. The analytical speed of the automated system was consistent with that required to guide initial empiric therapy in critically ill patients.

Example 10

Detection of Persister Clones Using Vital/Mortal Staining

Current microbiological methods use the absence or presence of bacterial cell growth and/or division to determine the effects of antibiotics on bacteria. Unfortunately, standard clinical microbiology approaches to determination of the minimum inhibitory concentration (MIC) of an antibiotic such as those provided by CLSI and EUCAST do not account for slowly growing clones or for clones that may grow after a dormant period. Survival of these persister clones may have dire consequences for a patient if ignored during the selection of an antibiotic treatment schema. Systems and methods in accordance with various embodiments of the present disclosure may be capable of detecting not only microorganism growth and/or division, but also may have the potential to detect several other indicators of bacterial activity, enabling a more thorough characterization of these persister clones during antibiotic susceptibility testing.

In order to identify persister clones capable of retaining activity after exposure to antibiotics, a variety of indicators that revealed different physiological states tested (Table 16). Physiologic indicators of active bacteria may include, for example, growth, responsiveness to external stimulus, transcription, translation, energy dependent activity, enzyme activity, and an intact permeability barrier. The indicators tested experimentally were grouped according to the following functional categories of physiologic states to which they are responsive, which included indicators of respiratory and metabolic activity, and membrane integrity.

TABLE 16

Indicators of bacterial activity grouped by functional category

| Membrane Potential |
| --- |
| $DiOC_2(3)$ |
| $DiBAC_4(3)$ |
| Respiratory/Metabolic Activity |
| CTC |
| $C_{12}$-Resazurin |
| CFDA |
| CFDA, SE |
| 2-NBDG |
| Membrane Integrity |
| YO-PRO-1 |
| PI |
| Plasmolysis |

Results

Membrane Potential Indicators

Active bacterial cells maintain a proton gradient across their cell membranes, creating a membrane potential that may be measured using fluorescent dyes. However, the dyes used in this study to evaluate membrane potential are toxic to bacteria and may only be used as an endpoint assay.

$DiBAC_4(3)$ (Molecular Probes) is an anionic dye that enters depolarized cells (i.e., cells lacking a membrane potential) and fluoresces in the red channel when it binds to intracellular proteins or membranes. Using this indicator, 18.5% of an overnight refrigerator stock (control) and 95% of heat-killed E. coli stained with 10 g/ml $DiBAC_4(3)$ after a 15 min incubation period at room temp.

$DiOC_2(3)$ (Molecular Probes) is a dye that fluoresces in the red channel when it is highly concentrated and self-associates in cells with an intact membrane potential. Fewer $DiOC_2(3)$ molecules are able to enter inactive cells and will exhibit a green fluorescence as a single molecule. The red:green fluorescence ratio is used to normalize the fluorescence results of cells with differing sizes. Carbonylcyanide-m-chlorophenylhydrazone (CCCP) is a proton ionophore that disrupts the proton gradient and was used to treat E. coli cells in an experimental sample that was compared to an untreated overnight refrigerator stock. No significant difference in red:green fluorescence ratios were observed between the O/N refrigerator stock and CCCP-treated E. coli, and further experimentation would be required to determine whether different dye concentrations would be effective for evaluation of cells with intact versus depolarized cell membranes using the system of the present disclosure.

Respiratory/Metabolic Activity Indicators

CTC (5-Cyano-2,3-ditolyl tetrazolium chloride) (Sigma) is a redox dye that produces an insoluble fluorescent formazan when it is reduced. Metabolically active bacteria that reduce CTC retain the formazan intracellularly and are detectable based on the fluorescence of the formazan. Overnight refrigerator stock cultures of both E. coli and S. aureus were fluorescently labeled with the reduced form of CTC after 25 min at 35° C. with 4 mM CTC in 0.9% NaCl.

2-NBDG (Molecular Probes) is a fluorescent derivative (green channel) of D-glucose that is internalized by active bacteria. Overnight refrigerator stock cultures of E. coli and K. pneumoniae were fluorescently labeled after approximately 1 min of exposure to 1 μM 2-NBDG. However, overnight refrigerator cultures of *H. influenzae, S. maltophilia*, and *S. aureus* did not fluoresce despite independent verification of the viability of the stock cultures used for the 2-NBDG experiment. While *S. maltophilia* does not metabolize glucose and served as a negative control providing results that conformed with expectations, the failure of *H. influenza* and *S. aureus* indicates that further experimentation is required and other carbon sources may provide better results and/or compatibility with a wider array of microbial species.

C12-Resazurin (Molecular Probes) is a redox dye that is reduced to a red-fluorescent C12-resorufin by metabolically active bacteria. The dyes is non-toxic and stable in culture media according to manufacturer literature. Overnight refrigerator stock cultures of *S. aureus* were able to reduce C12-Resazurin based on detection of the red-channel fluorescence. Unexpectedly, both heat-killed (2-7 h post heat-kill) and isopropyl alcohol killed *S. aureus* were also fluorescently labeled with C12-Resazurin. Further experimentation would be required to evaluate the suitability of this dye for detection of metabolically active bacteria while reducing false positive results.

Carboxyfluorescein diacetate/carboxyfluorescein diacetate succinimidyl ester (CFDA/CFDA-SE; Molecular Probes) compounds are converted into amine-reactive fluorescent molecules when cleaved by esterases present within active cells. When CFDA-SE is taken up by live cells, the fluorescent molecule produced by esterase cleavage and amine reaction is retained inside the cell. Hence, if the cell eventually becomes inactive, these cells will continue to fluoresce. The product formed by uptake and processing of CFDA, on the other hand, should be more "leaky" over time and may exit a dead cell. The difference in kinetics of dye exit between an active vs. inactive cell is unknown. Therefore, although the dyes are non-toxic, they would likely be most effective as an endpoint assay. In experiments performed using the MADM system, heat-killed cells and isopropyl alcohol killed cells demonstrated fluorescence when dyes were added immediately after treatment. A two hour post-heat-kill delay was sufficient to eliminate the possible residual esterase activity observed according to CFDA-SE assays (i.e., no fluorescence was observed with a delayed assay following heat-kill). Shorter delay times have not yet been investigated but may be compatible with avoiding false positive results while providing a shorter assay period.

Membrane Integrity Indicators

YO-PRO-1 (Molecular Probes) is a DNA-intercalcater that penetrates damaged membranes but not intact membranes. Experiments were conducted to verify non-toxicity of the dye to various test microorganisms, including *E. coli*, *S. aureus*, and *H. influenza*. This indicator has been successfully used as an indicator to assay membrane permeability in the aforementioned species, and the use of YO-PRO-1 to evaluate antibiotic susceptibility of individual microorganisms in a collection of large numbers of microorganisms is described in detail in U.S. Pat. No. 7,341,841, the entire contents of which are incorporated by reference herein.

Propidium iodide (PI; Sigma) is another red fluorescent DNA-intercalcater that penetrates damaged membranes but not intact membranes. Initial studies using PI were very promising and appeared comparable to YO-PRO-1. However, fluorescent signal intensity vs. background was not as high as for YO-PRO-1.

Plasmolysis is a method of detecting membrane integrity by exposing cells to a very hypertonic solution, such as may be performed by subjecting a cell to osmotic pressure by manipulating the concentration of a solute, for example, sodium chloride. Active cells will shrink in size in response to the osmotic pressure while inactive cells are unable to respond and will remain the same size. The ability to evaluate plasmolysis to assess cell membrane integrity was tested in *E. coli*, with 77% of cells from overnight refrigerator stock cultures decreasing in size when exposed to 0.9% NaCl, whereas 90% of heat killed cells did not exhibit a response. While certain reports suggest that plasmolysis may be more difficult to detect in gram-negative bacteria than in gram-positive cells, our results in experiments with *E. coli* indicate that plasmolysis may observed in this gram-negative organism using the system of the present disclosure.

Conclusion

Various dyes may be successfully used within and are compatible with the system and methods disclosed herein as indicators of cell viability that may be added at the outset of a growth determination evaluation (i.e., non-toxic cell membrane permeability indicators such as YO-PRO-1), while others may be used as endpoint indicators of cell activity or viability following growth evaluation and the results of such assays may be overlaid or correlated with growth determination conclusions generated using the growth analysis module as described herein.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Any communication, transmission and/or channel discussed herein may include any system or method for delivering content (e.g. signals, images, data, information, metadata, etc.), and/or the content itself. The content may be presented in any form or medium, and in various embodiments, the content may be delivered electronically and/or capable of being presented electronically.

In various embodiments, the methods described herein are implemented using the various particular machines described herein. The methods described herein may be implemented using those particular machines described herein, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., a Windows, UNIX, Linux, Solaris, Mac OS, or other suitable operating system) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more computers and/or one or more processors. The processor is connected to a communication infrastructure (e.g., a communications bus, cross over bar, or network). Various software embodiments are described in terms of this exemplary computer system. A computer system can include a display interface that forwards graphics, text, and other data from the communication infrastructure (or from a frame buffer not shown) for display on a display unit.

A computer system also includes a main memory, such as for example random access memory (RAM), and may also include a secondary memory. The secondary memory may include, for example, a hard disk drive and/or a removable storage drive. The removable storage drive reads from and/or writes to a removable storage unit in any suitable manner. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface.

A computer system may also include a communications interface. A communications interface allows software and data to be transferred between a computer system and external devices. Software and data transferred via the communications interface are in the form of signals which may be electronic, electromagnetic, optical and/or other signals capable of being received by the communications interface. These signals are provided to the communications interface via a communications path (e.g., channel).

The terms "computer program medium" and "computer usable medium" and "computer readable medium" are used to generally refer to media such as removable storage drive and a hard disk installed in hard disk drive. These computer program products provide software to a computer system.

Computer programs (also referred to as computer control logic) are stored in main memory and/or secondary memory. Computer programs may also be received via the communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into a computer system using removable storage drive, hard disk drive or communications interface. The software, when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

A web client includes any device (e.g., personal computer) which communicates via any network, for example such as those discussed herein. Such browser applications comprise Internet browsing software installed within a computing unit or a system to conduct online transactions and/or communications. These computing units or systems may take the form of a computer or set of computers, although other types of computing units or systems may be used, including laptops, notebooks, tablets, hand held computers (e.g., smartphones), set-top boxes, workstations, computer-servers, main frame computers, mini-computers, PC servers, pervasive computers, network sets of computers, personal computers.

In various embodiments, a web client may or may not be in direct contact with an application server. For example, a web client may access the services of an application server through another server and/or hardware component, which may have a direct or indirect connection to an Internet server. For example, a web client may communicate with an application server via a load balancer. In an exemplary embodiment, access is through a network or the Internet through a commercially-available web-browser software package.

In various embodiments, components, modules, and/or engines of system 100 (e.g., Healthcare IS 150) may be implemented as micro-applications or micro-apps. Micro-apps are typically deployed in the context of a mobile operating system. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

As used herein, the term "network" includes any cloud, cloud computing system or electronic communications system or method which incorporates hardware and/or software components. Communication among the parties may be accomplished through any suitable communication channels, such as, for example, a telephone network, data network, Internet, point of interaction device, online communications, satellite communications, off-line communications, wireless communications, transponder communications, local area network (LAN), wide area network (WAN), virtual private network (VPN), networked or linked devices, and/or any suitable communication or data input modality.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Any databases discussed herein may include relational, hierarchical, graphical, or object-oriented structure and/or any other database configurations. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art.

The data set annotation may be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like. Encryption may be performed by way of any of the techniques now available in the art or which may become available.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the Internet server.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

In various embodiments, systems may be described herein in terms of functional block components, screen shots, optional selections and various processing steps.

In various embodiments, systems are described herein with reference to screen shots, block diagrams and flowchart illustrations of methods, apparatus (e.g., systems), and computer program products. These functional blocks may be realized by any number of hardware and/or software components configured to perform the specified functions. These functional blocks flowchart illustrations, and combinations of functional blocks in the block diagrams and flowchart illustrations, respectively, may also be implemented by computer program instructions.

These computer program instructions may be loaded onto a general purpose computer, special purpose computer, or other programmable data processing apparatus to produce a machine, such that the instructions that execute on the computer or other programmable data processing apparatus create a computer system capable of implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of hardware, software, and/or hardware-software systems for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method, comprising:
   detecting, by a computer-based system in communication with a microorganism detection device, a first set of at least one of signals, spots, or singularities in a first image of a sample of an immobilized microorganism in a gel medium;
   determining, by the computer-based system, that a first subset of the first set of the at least one of signals, spots, or singularities are greater than a predetermined threshold by employing a first wavelet transformation for decomposing the first set of the at least one of signals, spots or singularities into wavelet functions, applying the wavelet functions to the first image and generating wavelet coefficients representing the first image of the immobilized microorganism on a plurality of levels of resolution to create a stack of first image planes;
   determining, by the computer-based system a first value associated with an attribute of the immobilized microorganism, based on first information associated with the first subset of the first set of at least one of signals, spots, or singularities that are greater than the predetermined threshold, wherein the attribute comprises at least one of a microorganism size, shape, mass, intrinsic fluorescence, cell surface feature membrane integrity, genomic DNA, ribosomal RNA subunits, or bound marker used in indirect immunofluorescence microscopy;
   detecting, by the computer-based system in communication with the microorganism detection device, a second set of at least one of signals, spots, or singularities in a second image of the sample of an immobilized microorganism, after an occurrence of an event;
   determining, by the computer-based system, that a second subset of the second set of the at least one of signals, spots, or singularities are greater than a predetermined threshold by employing a second wavelet transformation for decomposing the second set of the at least one of signals, spots, or singularities into wavelet functions, applying the wavelet functions to the second image and generating wavelet coefficients representing the second image of the immobilized microorganism on a plurality of levels of resolution to create a stack of second image planes;
   determining, by the computer-based system, a second value associated with the attribute of the immobilized microorganism, based on second information associated with the second set of at least one of signals, spots, or singularities that are greater than the predetermined threshold after the occurrence of the event;
   determining, by the computer-based system, a growth rate of the immobilized microorganism associated with the first value and the second value;
   comparing, by the computer-based system, the growth rate to a control growth rate; determining, by the computer-based system, a clone signal intensity curve shape likelihood and a tracking error likelihood; and
   calculating, by the computer-based system, a growth likelihood value based on the clone signal intensity curve shape likelihood and the tracking error likelihood.

2. The method of claim 1, wherein the immobilized microorganism is subjected to a condition.

3. The method of claim 2, wherein the condition is associated with the event.

4. The method of claim 2, wherein the condition is at least one of a temperature, a growth medium condition, a carbon source, a nitrogen source, an amino acid, a nutrient, a salt, a metal ion, a cofactor, a pH, a trace element, a dissolved gas, an antimicrobial agent, an aerobic condition, and an anaerobic condition.

5. The method of claim 2, wherein the condition is at least one of static and dynamic.

6. The method of claim 1, wherein the control growth rate is at least one of a predetermined growth rate and a dynamically determined growth rate.

7. The method of claim 1, wherein the event is at least one of a predetermined time, a dynamically determined mass, a number of individuated microorganisms, and a number of clones.

8. The method of claim 1, wherein the attribute is a plurality of attributes is evaluated simultaneously.

9. The method of claim 1, further comprising determining, by the computer-based system, microorganism susceptibility based on a comparison of the growth likelihood value to a range.

10. The method of claim 1, wherein the first wavelet transformation further comprises rendering, by the computer-based system, the first set of at least one of signals that are greater than the predetermined threshold and associated with the immobilized microorganism into a plurality of signal approximations.

11. The method of claim 10, wherein the first wavelet transformation further comprises wherein the plurality of signal approximations are planes comprising a plurality of point amplitudes corresponding to microorganism locations.

12. The method of claim 11, wherein the first wavelet transformation further comprises combining, by the computer-based system, the signal approximations to create a microorganism model.

13. The method of claim 11, wherein the first wavelet transformation further comprises analyzing, by the computer-based system, the point amplitudes associated with at least one of background information and noise information.

14. The method of claim 13, wherein the first wavelet transformation further comprises filtering, by the computer-based system, the signal approximations to eliminate the at least one of background information and noise information.

15. The method of claim 14, wherein the first wavelet transformation further comprises registering, by the computer-based system, locations associated with point amplitudes corresponding to the immobilized microorganism.

16. The method of claim 1, wherein the immobilized microorganism is an individuated microorganism.

* * * * *

UNITED STATES PATENT AND TRADEMARK OFFICE
CERTIFICATE OF CORRECTION

PATENT NO. : 11,603,550 B2
APPLICATION NO. : 15/484250
DATED : March 14, 2023
INVENTOR(S) : Alena Shamsheyeva et al.

It is certified that error appears in the above-identified patent and that said Letters Patent is hereby corrected as shown below:

In the Specification

Column 4, Line 10, "indicate" should be --indicating--.

Column 5, Line 4, "affect" should be --effect--.

Column 10, Line 20, "an" should be --and--.

Column 11, Line 28, "is means" should be --means--.

Column 14, Line 60, "For example," should be --One example of this is--.

Column 14, Line 65, "microorganisms." should be --microorganisms).--.

Column 15, Line 53, "(such" should be --[such--.

Column 15, Line 57, "array." should be --array].--.

Column 15, Line 58, "are" should be --is--.

Column 18, Line 36, "associated with growth rate with" should be --associated growth rate with--.

Column 19, Line 45, "to the each" should be --to each--.

Column 21, Line 44, "approximation" should be --approximations--.

Column 23, Line 11, "(i, j)" should be --(i, j).--.

Column 26, Line 1, "as a predecessors" should be --as predecessors--.

Signed and Sealed this
Twenty-first Day of November, 2023

Katherine Kelly Vidal
*Director of the United States Patent and Trademark Office*

CERTIFICATE OF CORRECTION (continued)
U.S. Pat. No. 11,603,550 B2

Column 26, Line 38, "can tagged by" should be --can be tagged by--.

Column 26, Line 47, "in order make" should be --in order to make--.

Column 27, Line 16, "signal being are collected," should be --signal are being collected,--.

Column 27, Line 20, "evaluate" should be --evaluates--.

Column 28, Line 17, "close" should be --clone--.

Column 35, Line 31, "(ceftazidime CAZ)" should be --(ceftazidime (CAZ)--.

Column 35, Line 34, "60-minutes" should be --60-minute--.

Column 37, Line 12, "10-minutes" should be --10-minute--.

Column 40, Line 17, "10-minutes" should be --10-minute--.

Column 40, Line 20, "the system approximately" should be --the system counted approximately--.

Column 40, Line 52, "increase," should be --increase in,--.

Column 40, Line 55, "4-hours" should be --4-hour--.

Column 41, Line 21, "by a broth" should be --by broth--.

Column 42, Line 4, "sample" should be --samples--.

Column 43, Line 6, "non lactose" should be --non-lactose--.

Column 45, Lines 46-47, "is a promising approach" should be --are a promising approach--.

Column 50, Line 40, "FIG. 22C" should be --(FIG. 22C--.

Column 50, Line 41, "stained)" should be --stained.)--.

Column 50, Line 46, "(FIG. 23A-23C" should be --(FIGS. 23A--23C--.

Column 52, Lines 64-66, "MLSB identification using ERY induction and CLI challenge (FIG. 25B; note difference in Y-axis scale compared to FIG. 25A)" should be --MLSB identification using ERY induction and CLI challenge is shown in FIG. 25B (note difference in Y-axis scale compared to FIG. 25A).--.

Column 53, Line 29, "enabled" should be --enables--.

Column 53, Line 30, "has" should be --have--.

CERTIFICATE OF CORRECTION (continued)
U.S. Pat. No. 11,603,550 B2

Column 55, Line 13, "dyes" should be --dye--.

Column 56, Line 13, "may observed" should be --may be observed--.

Column 59, Line 54, "are" should be --is--.

Column 60, Line 32, "blocks" should be --blocks,--.

In the Claims

Column 62, Lines 27-28, Claim 1, "cell surface feature membrane integrity," should be --cell surface feature, membrane integrity,--.

Column 63, Line 18, Claim 8, "plurality of attributes is evaluated simultaneously." should be --plurality of attributes evaluated simultaneously.--.